(12) United States Patent
Jones et al.

(10) Patent No.: US 12,741,047 B2
(45) Date of Patent: Sep. 22, 2026

(54) ENHANCED DISPENSER CONTROL

(71) Applicant: Pura Scents, Inc., Pleasant Grove, UT (US)

(72) Inventors: Brian Aaron Jones, Orem, UT (US); Bruno Miranda Lima, Orem, UT (US); Richard Nathanial Stapler, III, Orem, UT (US); Zachary Dennis Blume, Orem, UT (US)

(73) Assignee: Pura Scents, Inc., Pleasant Grove, UT (US)

( * ) Notice: Subject to any disclaimer, the term of this patent is extended or adjusted under 35 U.S.C. 154(b) by 356 days.

(21) Appl. No.: 18/508,598

(22) Filed: Nov. 14, 2023

(65) Prior Publication Data

US 2024/0075178 A1 Mar. 7, 2024

Related U.S. Application Data

(63) Continuation of application No. 18/310,389, filed on May 1, 2023, which is a continuation of application (Continued)

(51) Int. Cl.

| | |
|---|---|
| ***A61L 9/03*** | (2006.01) |
| ***H05B 1/02*** | (2006.01) |
| ***H05B 3/14*** | (2006.01) |

(52) U.S. Cl.

CPC ............... *A61L 9/037* (2013.01); *A61L 9/035* (2013.01); *H05B 1/0252* (2013.01); *H05B 3/141* (2013.01);

(Continued)

(58) Field of Classification Search

None

See application file for complete search history.

(56) References Cited

U.S. PATENT DOCUMENTS

| | | | |
|---|---|---|---|
| 2,732,148 | A | 1/1956 | Lummis |
| 3,195,581 | A | 7/1965 | Brosseit |

(Continued)

FOREIGN PATENT DOCUMENTS

| | | | |
|---|---|---|---|
| CN | 2289563 | Y | 9/1998 |
| CN | 1313163 | A | 9/2001 |

(Continued)

OTHER PUBLICATIONS

CapSense Design Code, Cypress Perform, www.cypress.com, 2016 (113 pages).

(Continued)

*Primary Examiner* — Thor S Campbell

(74) *Attorney, Agent, or Firm* — VLP Law Group, LLP

(57) ABSTRACT

A scent dispenser may comprise a vial retaining mechanism, a heating element, vial sensor, and a controller. The vial retaining mechanism includes a vial coupling that removeably retains a vial containing a scented solution. The includes a wick extending from a cavity of the vial through an opening of a neck of the vial. The heating element is shaped to receive and heat the wick of the vial. The vial sensor includes an array of sensor pads that are arranged in alignment with the vial retained by the vial coupling. The controller is electrically coupled to the heating element and electrically coupled to the array of sensor pads. The controller regulates a temperature level of the heating element, and receives signals from the array of sensor pads and processing the signals to determine a fluid level of the vial.

20 Claims, 52 Drawing Sheets

Related U.S. Application Data

No. 16/878,463, filed on May 19, 2020, now Pat. No. 11,918,710, which is a continuation of application No. 15/626,007, filed on Jun. 16, 2017, now Pat. No. 10,967,091, which is a continuation of application No. 15/342,065, filed on Nov. 2, 2016, now Pat. No. 9,827,343.

(60) Provisional application No. 62/279,766, filed on Jan. 17, 2016, provisional application No. 62/279,767, filed on Jan. 17, 2016, provisional application No. 62/279,698, filed on Jan. 16, 2016, provisional application No. 62/279,747, filed on Jan. 16, 2016, provisional application No. 62/279,748, filed on Jan. 16, 2016, provisional application No. 62/279,745, filed on Jan. 16, 2016, provisional application No. 62/279,005, filed on Jan. 15, 2016, provisional application No. 62/279,508, filed on Jan. 15, 2016, provisional application No. 62/279,316, filed on Jan. 15, 2016, provisional application No. 62/278,894, filed on Jan. 14, 2016, provisional application No. 62/278,913, filed on Jan. 14, 2016, provisional application No. 62/249,917, filed on Nov. 2, 2015.

(52) U.S. Cl.
CPC ...... *A61L 2209/111* (2013.01); *A61L 2209/12* (2013.01); *A61L 2209/135* (2013.01); *H05B 2203/021* (2013.01)

(56) References Cited

U.S. PATENT DOCUMENTS 3,645,493 A 2/1972 Manoogian et al.
3,786,995 A 1/1974 Manoogian et al.
3,876,498 A 4/1975 Justus
3,923,593 A 12/1975 Verseput
4,043,359 A 8/1977 Christo
4,128,357 A 12/1978 Barth et al.
4,142,415 A * 3/1979 Jung ..................... G01F 23/263 73/304 C
4,218,785 A 8/1980 Crawford et al.
4,331,289 A 5/1982 Killy
4,396,143 A 8/1983 Killy
4,483,769 A 11/1984 Sherman
4,490,075 A 12/1984 Risi et al.
4,523,604 A 6/1985 Hutto
4,530,497 A 7/1985 Moran et al.
4,544,305 A 10/1985 Hair
4,557,720 A 12/1985 Hemphill
4,562,960 A 1/1986 Marty et al.
4,563,937 A 1/1986 White
4,577,653 A 3/1986 Marty
4,583,341 A 4/1986 Barth et al.
4,586,255 A 5/1986 Jacobson
4,593,430 A 6/1986 Spangler et al.
4,601,148 A 7/1986 Risi et al.
4,624,051 A 11/1986 Apprille et al.
4,696,322 A 9/1987 Knapp et al.
4,703,875 A 11/1987 Malek
4,707,592 A 11/1987 Ware
4,722,847 A 2/1988 Heckert
4,765,365 A 8/1988 Roland
4,767,547 A 8/1988 Straathof et al.
4,802,255 A 2/1989 Breuer et al.
4,807,401 A 2/1989 Atwater
4,834,575 A 5/1989 Barth et al.
4,837,613 A 6/1989 Paxton et al.
4,864,898 A 9/1989 Tricinella
4,869,928 A 9/1989 Kurumatani et al.
4,885,155 A 12/1989 Parran et al.
4,905,337 A 3/1990 McKay
4,916,817 A 4/1990 Atwater
4,929,351 A 5/1990 Sanborn
4,949,600 A 8/1990 Tricinella
4,969,996 A 11/1990 Hankammer
4,981,239 A 1/1991 Cappel et al.
4,986,420 A 1/1991 Gunn et al.
5,000,356 A 3/1991 Johnson et al.
5,009,828 A 4/1991 McCree
5,027,465 A 7/1991 McKay
5,050,103 A 9/1991 Schiller et al.
5,059,282 A 10/1991 Ampulski et al.
5,063,062 A 11/1991 Greenspan et al.
5,073,235 A 12/1991 Trokhan
5,094,761 A 3/1992 Trinh et al.
5,111,477 A 5/1992 Muderlak et al.
5,156,834 A 10/1992 Beckmeyer et al.
5,175,791 A 12/1992 Muderlak et al.
5,191,525 A 3/1993 Lebrun et al.
5,237,816 A 8/1993 Duffy et al.
5,259,062 A 11/1993 Pelonis
5,297,725 A 3/1994 Sutherland
5,376,006 A 12/1994 Fischer
5,511,122 A 4/1996 Atkinson
5,535,474 A 7/1996 Salazar
5,541,170 A 7/1996 Rhodes et al.
5,583,122 A 12/1996 Benedict et al.
5,620,965 A 4/1997 Blank
5,652,228 A 7/1997 Bissett
5,687,259 A 11/1997 Linford
5,687,485 A 11/1997 Shurtleff et al.
5,721,005 A 2/1998 Gutwein et al.
5,735,011 A 4/1998 Asher
5,746,598 A 5/1998 Fischer
5,761,814 A 6/1998 Anderson et al.
5,783,544 A 7/1998 Trinh et al.
5,849,728 A 12/1998 Bissett
5,872,112 A 2/1999 Blank
5,891,453 A 4/1999 Sagel et al.
5,894,017 A 4/1999 Sagel et al.
D411,456 S 6/1999 Mast et al.
5,922,307 A 7/1999 Montgomery
5,924,597 A 7/1999 Lynn
5,926,897 A 7/1999 Volpenhein
5,930,474 A 7/1999 Dunworth et al.
5,956,848 A 9/1999 Tseng et al.
5,956,851 A 9/1999 Apprille et al.
5,989,569 A 11/1999 Dirksing et al.
5,997,890 A 12/1999 Sine et al.
6,026,532 A 2/2000 Catanzaro
6,041,926 A 3/2000 Petricca et al.
6,045,811 A 4/2000 Dirksing et al.
6,052,903 A 4/2000 Metcalf et al.
6,067,525 A 5/2000 Johnson et al.
6,077,318 A 6/2000 Trinh et al.
6,096,342 A 8/2000 Dansereau et al.
6,118,248 A 9/2000 Gartstein et al.
6,126,980 A 10/2000 Smith et al.
6,165,513 A 12/2000 Dansereau et al.
6,185,822 B1 2/2001 Tseng et al.
6,202,150 B1 3/2001 Young et al.
6,212,777 B1 4/2001 Gilder et al.
6,232,523 B1 5/2001 Tan et al.
6,235,968 B1 5/2001 Tan et al.
6,248,135 B1 6/2001 Trinh et al.
6,248,390 B1 6/2001 Stillman
6,251,384 B1 6/2001 Tan et al.
6,254,065 B1 7/2001 Ehrensperger et al.
6,265,008 B1 7/2001 Smith et al.
6,266,674 B1 7/2001 Hejna, Jr.
6,278,455 B1 8/2001 Baker
6,284,007 B1 9/2001 Tao
6,308,359 B2 10/2001 Fritsch et al.
6,326,040 B1 12/2001 Kearney et al.
6,331,292 B1 12/2001 Montgomery
6,367,108 B1 4/2002 Fritsch et al.
6,457,969 B1 10/2002 Khosla
6,487,367 B2 * 11/2002 Vieira ..................... A61L 9/037 392/395
6,490,920 B1 * 12/2002 Netzer .................. G01F 23/268 73/304 C

(56) References Cited

U.S. PATENT DOCUMENTS 6,497,735 B2 12/2002 Tao
6,522,834 B1 2/2003 Herrick et al.
6,536,746 B2 3/2003 Watkins et al.
6,579,516 B1 6/2003 Mansouri
6,581,915 B2 6/2003 Bartsch et al.
D487,660 S 3/2004 Sayers et al.
6,712,287 B1 * 3/2004 Le Pesant .............. A61L 9/125 239/69
6,779,905 B1 8/2004 Mazursky et al.
6,783,117 B2 8/2004 Wohrle
6,859,615 B2 2/2005 Yip et al.
6,950,607 B2 * 9/2005 Yip ........................ A61L 9/037 392/390
6,963,271 B1 11/2005 Fyffe
7,047,983 B2 5/2006 Manougian et al.
7,131,603 B2 11/2006 Sakaida et al.
7,152,758 B2 12/2006 Fazzio et al.
7,152,809 B2 12/2006 Ketcha et al.
7,164,849 B1 1/2007 Bankers et al.
7,188,100 B2 3/2007 De et al.
7,223,166 B1 5/2007 Wiseman et al.
7,389,943 B2 * 6/2008 Jaworski ............. B05B 17/0646 239/326
RE40,464 E * 8/2008 Vieira .................... A61L 9/037 219/486
7,469,844 B2 * 12/2008 Conway .................. A61L 9/127 239/326
D584,809 S * 1/2009 Porchia ........................ D23/366
7,493,028 B2 * 2/2009 DeWitt .................... F24F 6/10 392/386
7,574,432 B1 8/2009 De Bellis
7,610,118 B2 * 10/2009 Schramm ............ A01M 1/2038 239/69
7,622,073 B2 * 11/2009 Schramm ................ A61L 9/037 422/123
7,625,187 B2 * 12/2009 Collins ............... F04D 15/0218 417/44.1
D615,415 S 5/2010 Holmes et al.
7,712,683 B2 5/2010 Robert et al.
7,734,159 B2 * 6/2010 Beland .................... A61L 9/127 392/390
D623,532 S 9/2010 Kuzma et al.
7,930,068 B2 4/2011 Robert et al.
D639,923 S * 6/2011 Belongia ...................... D23/366
8,027,575 B2 * 9/2011 Hasik ........................ A61L 9/03 392/394
8,135,265 B2 * 3/2012 Tollens ............... B05B 17/0684 392/395
8,170,405 B2 * 5/2012 Harris ................... A01M 1/205 392/386
8,346,894 B2 1/2013 Arunachalam
8,385,730 B2 2/2013 Bushman et al.
8,429,005 B2 4/2013 Mannik et al.
8,472,976 B1 6/2013 Ledet
8,615,825 B2 * 12/2013 Bovill ....................... E03C 1/12 4/679
8,633,623 B2 * 1/2014 Bingler ................... F04B 17/03 310/43
8,721,962 B2 * 5/2014 Woo ..................... B60H 3/0007 422/123
8,881,945 B2 11/2014 Gasper et al.
8,892,129 B1 11/2014 Ledet
8,910,640 B2 * 12/2014 Sears ........................ F22B 1/28 131/194
8,983,278 B2 * 3/2015 Ruiz Ballesteros .... A61L 9/037 392/394
8,983,279 B2 * 3/2015 Adair ................... H05B 1/0225 392/395
9,427,485 B2 * 8/2016 Tremblay .................. A61L 2/20
9,462,414 B1 10/2016 Ledet
9,669,125 B2 6/2017 Gasper
9,717,813 B2 8/2017 Deflorian et al.
10,179,184 B2 1/2019 Belz et al.
10,561,804 B1 2/2020 Culligan
10,750,265 B1 8/2020 Liao et al.
10,799,839 B1 10/2020 Brookins
10,834,968 B2 11/2020 John et al.
10,932,065 B2 2/2021 Ayache et al.
10,987,446 B2 4/2021 King
11,209,887 B1 12/2021 Jung
11,213,601 B2 1/2022 Jones et al.
11,253,624 B2 2/2022 Jones et al.
11,400,823 B1 8/2022 Sampath et al.
11,896,743 B2 2/2024 Turner et al.
2003/0138241 A1 7/2003 Pedrotti et al.
2003/0175148 A1 9/2003 Kvietok et al.
2003/0230091 A1 12/2003 Dillenback
2004/0005240 A1 1/2004 Adiga et al.
2004/0033171 A1 2/2004 Kvietok et al.
2004/0050951 A1 3/2004 Almero
2004/0204043 A1 10/2004 Wang et al.
2004/0247300 A1 12/2004 He et al.
2004/0247301 A1 12/2004 Yip et al.
2005/0167860 A1 8/2005 Brooks
2005/0185398 A1 8/2005 Scannell, Jr.
2005/0205916 A1 9/2005 Conway et al.
2005/0226788 A1 10/2005 Hrybyk et al.
2005/0278224 A1 12/2005 Bannai et al.
2006/0001714 A1 * 1/2006 Usui .................... B41J 2/17513 347/86
2006/0153744 A1 7/2006 Thompson et al.
2006/0193611 A1 8/2006 Ruiz et al.
2006/0219962 A1 * 10/2006 Dancs .................. G01F 23/265 250/577
2007/0014549 A1 1/2007 Demarest et al.
2007/0036673 A1 2/2007 Selander
2007/0058955 A1 * 3/2007 Bankers, PHD ........ G01F 23/22 392/386
2007/0235555 A1 10/2007 Helf et al.
2008/0013932 A1 1/2008 He et al.
2008/0050102 A1 * 2/2008 Lamers ..................... A61L 9/03 392/386
2008/0056691 A1 * 3/2008 Wingo .................... A61L 9/122 222/23
2008/0085103 A1 4/2008 Beland et al.
2009/0149334 A1 * 6/2009 Waterbury ........... G01N 27/226 506/7
2010/0018732 A1 1/2010 Daniel et al.
2010/0094468 A1 * 4/2010 Sahu ..................... H01M 8/188 73/304 R
2010/0143186 A1 6/2010 Belmonte et al.
2010/0178042 A1 7/2010 Neumann et al.
2010/0187327 A1 7/2010 Irvin
2010/0210313 A1 8/2010 Huang et al.
2010/0226617 A1 9/2010 Piccionelli
2010/0243754 A1 9/2010 Harris
2011/0220636 A1 9/2011 Hendricks et al.
2012/0018528 A1 1/2012 Samain
2012/0080537 A1 4/2012 Walter
2012/0240932 A1 9/2012 Gusky et al.
2012/0262133 A1 10/2012 Martinelli
2013/0081541 A1 4/2013 Hasenoehrl et al.
2013/0093108 A1 4/2013 Scolari
2013/0276532 A1 * 10/2013 Kato ..................... G01F 23/268 73/304 C
2013/0306752 A1 11/2013 Ruiz et al.
2014/0014685 A1 1/2014 Luc et al.
2014/0152323 A1 6/2014 Kumar et al.
2015/0133209 A1 5/2015 Patterson et al.
2015/0235546 A1 8/2015 Stapleford
2015/0267123 A1 * 9/2015 Ito .......................... C10G 2/344 518/712
2015/0297776 A1 10/2015 Conroy et al.
2015/0320116 A1 11/2015 Bleloch et al.
2015/0352544 A1 * 12/2015 Buermann ........ B01L 3/502715 435/6.12
2015/0359263 A1 12/2015 Bellinger
2016/0081393 A1 3/2016 Black
2016/0097668 A1 * 4/2016 Vilag .................... G01F 23/265 73/304 C
2016/0157524 A1 6/2016 Bowen et al.

(56) References Cited

U.S. PATENT DOCUMENTS

| | | | | |
|---|---|---|---|---|
| 2016/0330999 | A1 | 11/2016 | Cameron | |
| 2016/0361452 | A1 | 12/2016 | Blackley | |
| 2017/0046738 | A1 | 2/2017 | Cameron | |
| 2017/0055740 | A1* | 3/2017 | Sindi | H04R 1/028 |
| 2017/0119058 | A1 | 5/2017 | Cameron | |
| 2017/0135411 | A1 | 5/2017 | Cameron | |
| 2017/0173203 | A1 | 6/2017 | Becker et al. | |
| 2017/0303591 | A1 | 10/2017 | Cameron et al. | |
| 2018/0020727 | A1 | 1/2018 | Hoffman et al. | |
| 2018/0036448 | A1 | 2/2018 | Becker et al. | |
| 2018/0153208 | A1 | 6/2018 | Schaller et al. | |
| 2018/0286207 | A1 | 10/2018 | Baker et al. | |
| 2019/0117820 | A1 | 4/2019 | Dam | |
| 2019/0158938 | A1 | 5/2019 | Bowen et al. | |
| 2019/0365941 | A1 | 12/2019 | Elrod | |
| 2019/0369576 | A1 | 12/2019 | Elrod | |
| 2020/0179544 | A1 | 6/2020 | Ufkes | |
| 2020/0276350 | A1 | 9/2020 | Jones et al. | |
| 2020/0352249 | A1 | 11/2020 | Achtien et al. | |
| 2021/0145068 | A1 | 5/2021 | Bessant et al. | |
| 2022/0269763 | A1 | 8/2022 | Lett et al. | |
| 2023/0028709 | A1 | 1/2023 | Fuchs et al. | |
| 2023/0218795 | A1 | 7/2023 | Kumpf | |
| 2023/0285623 | A1 | 9/2023 | Jones et al. | |
| 2024/0075178 | A1* | 3/2024 | Jones | A61L 9/037 |
| 2024/0350692 | A1 | 10/2024 | Jones et al. | |
| 2025/0082811 | A1 | 3/2025 | Jones et al. | |
| 2025/0090710 | A1 | 3/2025 | Jones et al. | |

FOREIGN PATENT DOCUMENTS

| | | | |
|---|---|---|---|
| CN | 1642583 | A | 7/2005 |
| CN | 1696930 | A | 11/2005 |
| CN | 1832780 | A | 9/2006 |
| CN | 1878574 | A | 12/2006 |
| CN | 101068466 | A | 11/2007 |
| CN | 101141983 | A | 3/2008 |
| CN | 101528274 | A | 9/2009 |
| CN | 102271718 | A | 12/2011 |
| CN | 102526789 | A | 7/2012 |
| CN | 103096941 | A | 5/2013 |
| EP | 0345149 | A2 | 12/1989 |
| TW | M498019 | U | 4/2015 |
| WO | 90/12600 | A1 | 11/1990 |
| WO | 96/23530 | A1 | 8/1996 |
| WO | 2004/080604 | A2 | 9/2004 |

OTHER PUBLICATIONS

CapSense.sub.--CSD.sub.--P4 Slider Design example project 1.20, Cypress Perform, 2014 (7 pages).

CapSense_CSD_P4 Slider Design example project 1.20, Cypress Perform, 2014 (7 pages).

Extended European Search Report of Application No. EP16862913.7 dated Jun. 26, 2019, p. 1-13.

International Preliminary Report on Patentability received for PCT Patent Application No. PCT/US16/60184, mailed on May 17, 2018, 9 pages.

International Search Report and Written Opinion received for PCT Patent Application No. PCT/US16/60184, mailed on Mar. 10, 2017, 11 pages.

International Search Report and Written Opinion, PCT/US2016/060184, dated Mar. 10, 2017 (16 pages).

Invitation to Pay Additional Fees received for PCT Patent Application No. PCT/US16/60184, mailed on Dec. 29, 2016, 2 pages.

Office Action of Application No. CN201680077088.4, dated Apr. 9, 2020, p. 1-2.

Office Action received for Canadian Patent Application No. 3133710, mailed on Dec. 7, 2022, 4 pages.

Office Action received for Chinese Patent Application No. 202111083845.8, mailed on Jan. 12, 2023, 12 pages.

Office Action received for Chinese Patent Application No. 202111083845.8, mailed on Jul. 19, 2023, 10 pages.

Office Action received for European U.S. Appl. No. 16/862,913, mailed on Sep. 13, 2021, 5 pages.

Partial European Search Report and Search Opinion Received for EP Application No. 16862913, mailed on Mar. 27, 2019, 10 pages.

Programmable System-on-Chip (PSoC), Cypress Embedded in Tomorrow, Jun. 28, 2016 (44 pages).

Wikipedia, "Geo-fence," download from https://en.wikipedia.org/wiki/Geo-fence Oct. 30, 2016 (2 pages).

Office Action received for Chinese Patent Application No. 202111083845.8, mailed on Dec. 12, 2023, 11 pages of Original Document Only.

Office Action received for European Patent Application No. 16862913, mailed on Sep. 3, 2024, 4 pages.

Office Action received for Chinese Patent Application No. 202111083845.8, mailed on Mar. 14, 2024, 21 pages (13 pages of English Translation and 8 pages of Original Document).

International Search Report and Written Opinion received for Intl. Application No. PCT/US2016/60184, mailed Mar. 10, 2017 (16 pages).

* cited by examiner

Monitor motion using motion sensor of scent dispenser
1206

Determine room vacant based on monitored motion
1208

Suspend dispensing of scent based on determined room vacancy
1210

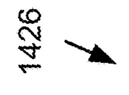
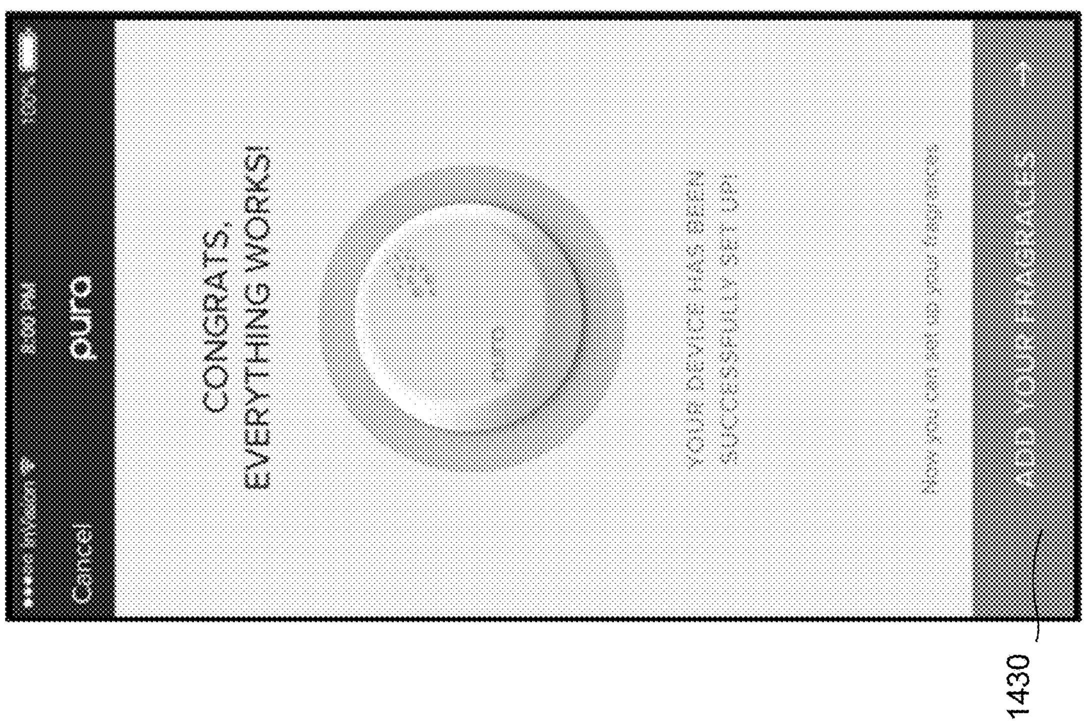
Figure 14G
Figure 14H

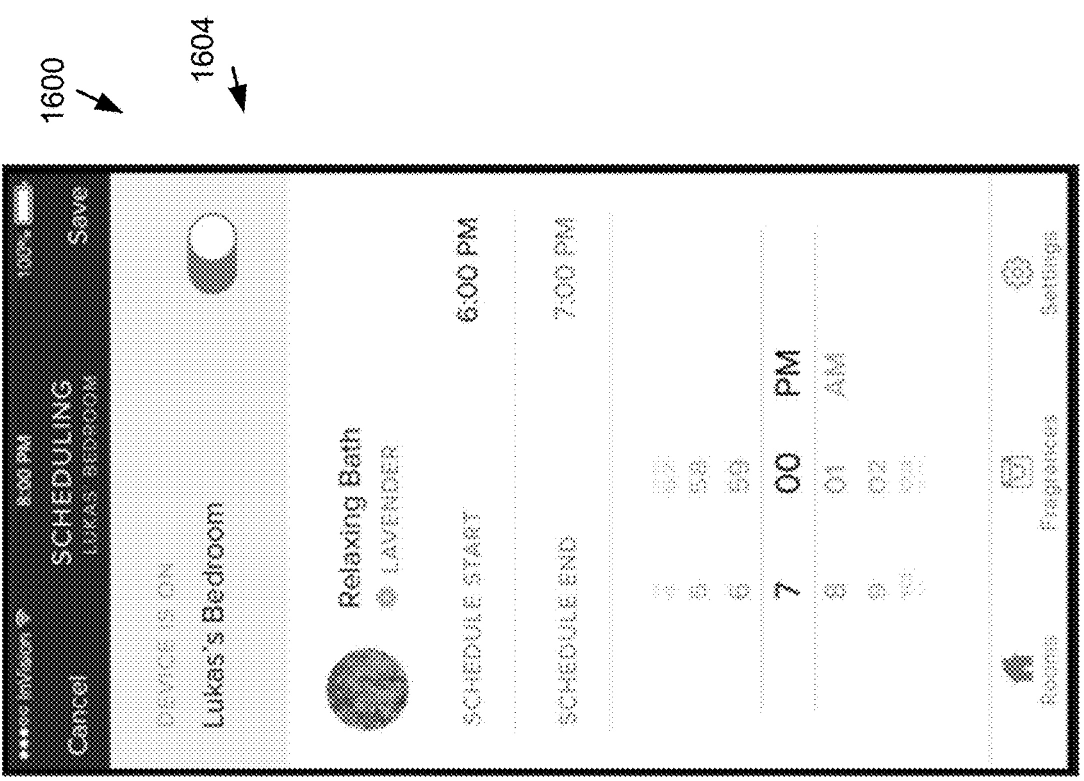
Figure 16B
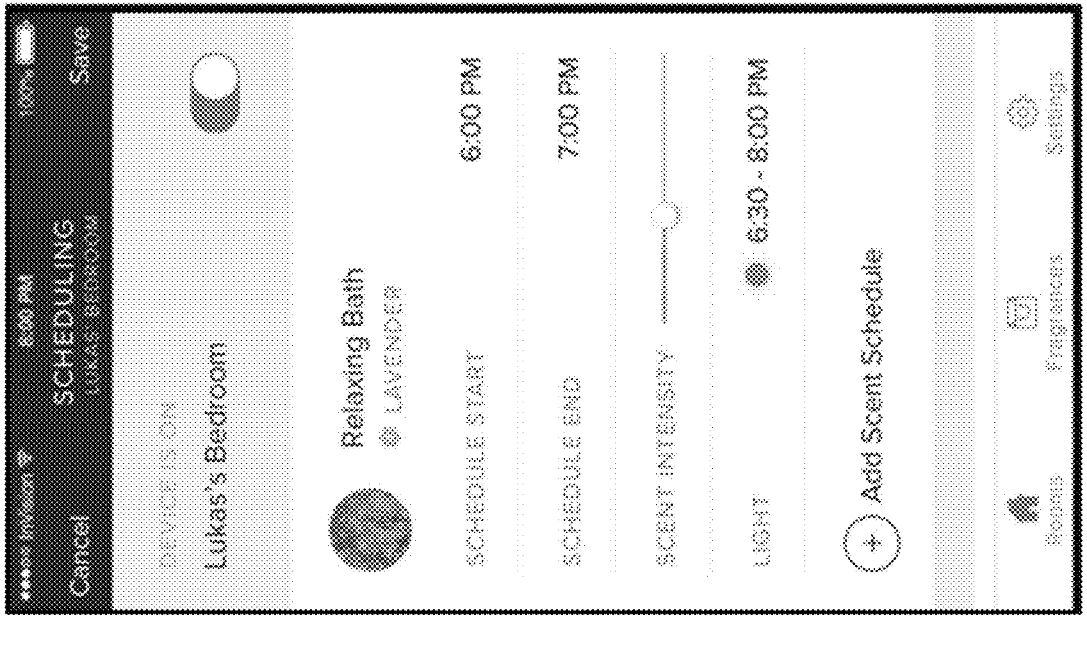
Figure 16A

1834

1834

1836

1838

1918
1920

1912
1914
1916

ENHANCED DISPENSER CONTROL

BACKGROUND

The present disclosure relates to scent dispensation.

Existing solutions for dispensing scents within a location, such as a home, include conventional scented candles, incense stocks, hanging air fresheners, and electric fragrance diffusers, such as those that plug into an outlet socket and include a heating element to heat a fragrant substance. In some cases, a porous substrate is saturated with the fragrant substance and then placed adjacent to a heat source, which heats up the fragrant substance to diffuse it within a predetermined space.

While functional, these solutions are limited. For example, it is often difficult to tell when a fragrance dispenser has run out of fragrance, as the dispenser typically lacks any sort of indicator and one is left to smell the dispenser manually to determine how much fragrance is actually left, which is ineffective as the dispenser itself may still smell like the diffuse fragrance up close that may have little effect in the area that is to be perfumed. In addition, if the users wishes to change a fragrance, the user has to manually open the dispenser to replace the cartridge in the dispenser, or in the case of hanging dispensers, replace it with a fresh version.

Existing scent dispensers also provide little control to users to configure how much scent is actually being diffused. Some existing electronic scent dispensers include a hardware selector to switch the device between off, low, and high operating states. However, these electronic scent dispensers are not self-aware, and therefore output the same amount of scent over time. Therefore, even at a low setting, the scent dispenser can eventually over-perfume a room, and only change state when manually switched off or set to another level by the user using the switch. This results in the unpleasant experience of the room becoming too perfumed and, in some cases, causes people to leave the room.

SUMMARY

According to one innovative aspect of the subject matter being described in this disclosure, an example system includes a first vial including a first side, one or more sidewalls, and a second side. The one or more sidewalls connect the first side to the second side. The first side, the one or more sidewalls, and the second side collectively form an inner cavity. The first side includes an opening through which a solution containable in the inner cavity is dispensed from the first vial. The system includes a vial sensor including a first array of sensor pads electrically coupled to a controller, a sidewall from the one or more sidewalls of the first vial being situated adjacent to the first array of sensor pads within a first array of electric fields. The first array of sensor pads are electrically charged to produce the first array of electric fields. The controller detects changes in one or more of the electric fields of the first array as the solution is dispensed from the first vial.

In general, the system may optionally include one or more of the following features: a second vial including a first side, one or more sidewalls, a second side; that the one or more sidewalls of the second vial connect the first side of the second vial to the second side of the second vial; that the first side of the second vial, the one or more sidewalls of the second vial, and the second side of the second vial collectively form an inner cavity of the second vial; that the first side of the second vial includes an opening through which a second solution containable in the inner cavity is dispensed from the second vial; that the first array of sensor pads are situated along a first side of the vial sensor; that the vial sensor includes a second array of sensor pads electrically coupled to the controller and situated along a second side of the vial sensor situated located adjacent to the first side of the vial sensor; that a sidewall from the one or more sidewalls of the second vial is situated adjacent to the second array of sensor pads with a second array of electric fields; that the second array of sensor pads is electrically charged to produce the second array of electric fields; that the controller detects changes in the one or more of the electric fields of the second array as the second solution is dispensed from the second vial; a vial retaining mechanism including a first vial coupling and a second vial coupling; that the first vial coupling receives and detachably retains the first side of the first vial, and the second vial coupling receives and detachably retains the first side of the second vial; that the first side of the first vial includes a neck through which the opening of the first side of the first vial extends; that the first side of the second vial includes a neck through which the opening of the first side of the second vial extends; that the first vial coupling includes one or more surfaces shaped to engage with and secure the neck of the first side of the first vial; that the second vial coupling includes one or more surfaces shaped to engage with and secure the neck of the first side of the second vial; that the vial retaining mechanism includes a first wick receiver and a second wick receiver; that the first wick receiver includes a stopping member having a wick hole extending through the stopping member of the first wick receiver; that the second wick receiver includes a stopping member having a wick hole extending through the stopping member of the second wick receiver; that the wick hole of the first wick receiver receives a wick extending outwardly from the opening of the first side of the first vial; that the wick hole of the second wick receiver receives a wick extending outwardly from the opening of the first side of the second vial; a first heating element situated on a side of the stopping member opposing the first vial; a second heating element situated on the side of the stopping member opposing the second vial; that the first heating element heats an end of the wick extending through the wick hole of the first wick receiver, and the second heating element heats an end of the wick extending through the wick hole of the second wick receiver; that the first heating element includes a ring that receives the end of the wick extending through the wick hole of the first wick receiver; that the second heating element includes a ring that receives the end of the wick extending through the wick hole of the second wick receiver; that the first heating element and the second heating element are formed at least in part of a ceramic material; a first vial coupling that receives and detachably retains the first vial; a heating element that heats the solution receivable from the first vial; a housing that houses the first vial coupling, the heating element, and the vial sensor; that a front side of the housing includes an opening providing access to the first vial; a removable cover that, when attached to the front side of the housing, covers the opening providing access to the first vial; that the removable cover includes one or more first magnetic fasteners; and that the front side of the housing includes one or more second magnetic fasteners that are compatible with the one or more first magnetic fasteners and that magnetically engage with the one or more first magnetic fasteners when the removable cover is situated abuttingly with the front side of the housing.

In general, according to a further innovative aspect, an example system includes a vial retaining system, a heating element, a vial sensor, and a controller. The vial retaining mechanism includes a vial coupling that removeably retains a vial containing a scented solution. The vial includes a neck forming an opening, a hollow body forming a cavity containing the scented solution, and a wick extending from the cavity through the opening of the neck. The heating element is shaped to receive and heat the wick of the vial. The vial sensor includes an array of sensor pads that are arranged in alignment with the vial retained by the vial coupling. The controller is electrically coupled to the heating element and electrically coupled to the array of sensor pads. The controller regulates a temperature level of the heating element. The controller receives signals from the array of sensor pads and processing the signals to determine a fluid level of the vial.

In general, the system may optionally include one or more of the following features: that the wick passes the scented solution to the heating element; that the heating element diffuses the scented solution by heating the scented solution to the temperature level regulated by the controller; that the controller electrically charges the sensor pads of the array; and that the controller detects a change in the signals received from the array of sensor pads charged by the controller and determines a corresponding change in the fluid level of the scented solution of the vial; the change in the signals is a change in capacitance of at least one of the sensor pads; that the signals from a first subset of the sensor pads reflect a maximum capacitance level; that the signals from a second subset of the sensor pads of the array reflect a minimum capacitance level; and that the controller determines the fluid level of the vial based on the signals from the first subset and the signals from the second subset; that the sensor pads comprise copper pads; that the vial coupling includes one or more fasteners formed to detachably engage with the neck of the vial; that the one or more fasteners include one or more clips;

In general, according to a further innovative aspect, an example system includes a vial retaining system, two or more heating elements, a vial sensor, and a controller. The vial retaining mechanism includes two or more vial couplings that removeably retain two or more vials. The two or more vials each include a neck forming an opening, a hollow body forming a cavity, and a wick extending from the cavity through the opening of the neck. Each of the two or more heating elements are shaped to receive and heat the wick of a corresponding vial of the two or more vials. The vial sensor includes two or more arrays of sensor pads that are respectively arranged in alignment with the two or more vials retained by the two or more vial couplings. The controller is electrically coupled to the two or more heating elements and electrically coupled to each of the two or more arrays of sensor pads. The controller regulates a temperature level of each of the two or more heating elements, and the controller receives signals from the arrays of sensor pads and processes the signals to determine a fill level of each of the two or more vials.

Further innovative aspects include corresponding systems, methods, apparatus, and computer program products. These systems, methods, apparatus, computer program products, and other aspects, are particularly advantageous in a number of respects. For example, the technology enables users to remotely control scent dispensers, switch between scents remotely, and receive notifications when a scent solution is running/has run out, automatically switches the scent solution(s) to diffuse based on user location, allows users to schedule scent diffusion for different locations, etc. In addition, the technology can collect data about scent solution usage and user habits when using scent dispensers, and then analyze that data to produce analytics to inform producers about characteristics of the users, the scents being consumed, etc. Numerous additional features are also possible and contemplated, many of which are discussed herein.

However, this list of features and advantages is not all-inclusive and many additional features and advantages are within the scope of the present disclosure. Moreover, it should be noted that the language used in the present disclosure has been principally selected for readability and instructional purposes, and not to limit the scope of the subject matter disclosed herein.

BRIEF DESCRIPTION OF THE DRAWINGS

FIG. 2A is a front perspective view of an example scent dispenser.

FIG. 2B is a rear perspective view of the example scent dispenser.

FIGS. 14A-14H are graphical representations of user interfaces for setting up a scent dispenser.

FIGS. 16A-16E are graphical representations of user interfaces for scheduling scent dispensation for one or more rooms.

DETAILED DESCRIPTION

The technology described in this disclosure relates to dispensing scent within the premises using remotely controllable scent dispensers. As an example, the technology allows the user to remotely control the operation of scent dispensers installed in his or her home using a mobile application executed on a mobile device. Using the mobile application, the user may turn a scent dispenser on or off, change the scent that is being dispensed by the dispenser, change the intensity level of the scent dispensation, set a schedule for the scent dispensation, control the operation of the scent device based on the location of his/her mobile device, receive status notifications from about the operation of the scent dispenser, such as when a particular scent solution may be running out, etc.

Figure 1A:
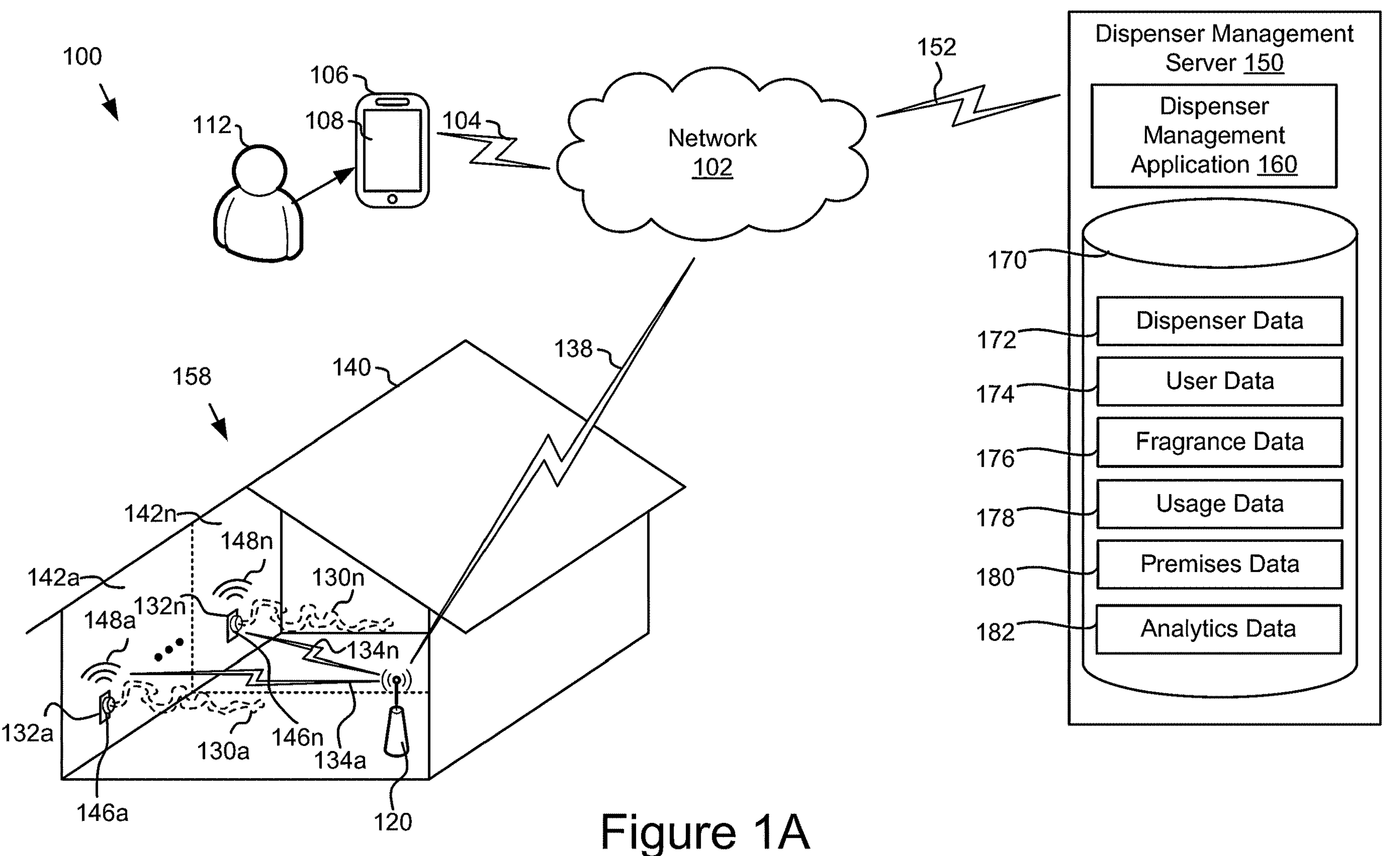
FIG. 1A is a block diagram illustrating an example system for scent dispensation.

FIG. 1A is a block diagram illustrating an example system 100 for scent dispensation. The system 100 may include one or more scent dispenser installations 158. In a typical implementation, a multiplicity of users 112 may install scent dispenser on their respective premises 140 in which they wish to dispense various scents. A scent dispenser installation 158 may include any number of scent dispensers 132*a* . . . 132*n*. In the depicted implementation, scent dispensers 132*a* and 132*n* (individually or collectively also referred to as simply 132) are plugged into electrical sockets 146*a* and 146*n*. The scent dispensers 132 may be located in the same room or in different rooms (e.g., 142*a* and 142*n*).

As shown, the illustrated system 100 further includes client device(s) 106 and a server 150, which are electronically communicatively coupled via a network 102 for interaction with one another, access point(s) 120, and the scent dispenser(s) 132, etc., using standard networking protocols, as reflected by signal lines 104, 138, and 152. In a typical installation, the scent dispenser(s) 132 are coupled for electronic communication with the access point(s) 120 (e.g., a modem, router, etc., coupled to the network 102) as reflected by signal lines 134*a* and 134*n*. In further embodiments, the scent dispenser(s) 132 may be coupled directly to the network 102 as reflected by the signal line 138, such as via a wireless wide area network (e.g., WWAN) or other suitable network. For clarity, reference to the term network 102 includes the local networks of the installations (e.g., provided by access point(s) 120, etc.), unless otherwise specified.

The scent dispenser 132 includes a communication-enabled diffusion device that diffuses scent solution(s) from scent vial(s) installed in the scent dispenser 132. The scent dispenser 132 may include wireless transceivers configured to communicate with other devices within range, such as other scent dispenser(s) 132 and/or access point(s) 120. In some embodiments, the diffusion device nebulizes the scent solution into the air of the surrounding environment to diffuse the scent. The structure, acts, and/or functionality of the scent dispenser 132 is discussed further below.

The access point 120 connects to the set of scent dispensers 132 installed on the premises 140, as shown by the signal lines 134*a* . . . 134*n*, and exchanges data sent between the scent dispensers 132 and the mobile device(s) 106 and/or the dispenser management server 150 (e.g., via the signal line 138).

The dispenser management application 160 operable by the dispenser management server 150 can receive operational data from the scent dispensers 132 in association with the premises 140, room 142, user(s) 112, and/or scent vials (e.g., see FIG. 2C) with which they are associated. The dispenser management application can receive management requests and geolocation data from mobile devices of the user(s) 112 in association with the scent dispenser(s) 132 that are registered to the user(s) in the system 100. The management requests may include registration data requesting to register a scent dispenser 132 with a user's 112 account, a particular premises, and/or a room within the premises; scheduling data requesting to schedule dispensation of scent(s), from scent dispenser 132 or a set of two or more scent dispenser(s) 132, for particular timeframe(s) within a particular room of a premises; operational data instructing to activate or deactivate a scent dispenser 132 and/or specifying which scent solution to activate and/or deactivate; geolocation data indicating a current location of a user, etc. The scheduling data may include a reoccurring schedule that repeats on certain days and/or times of day, and may specify which scent solution(s) should be dispensed at which times.

In some embodiments, the dispenser management application 160 may maintain the device states, scent allocations, users, and schedules of the scent dispensers 132. The dispenser management application 160 may make device function calls to command/control the scent dispensers 132 (e.g., by sending state settings), and may receive and log published events (heartbeat, alerts, data, etc.) received from the scent dispensers 132 in the data store 170. Example events may include, but are not limited to:

| Description | Event Name (string) | Event Data (string) |
|---|---|---|
| Device online | "spark/status" | online |
| Device flash started | "spark/flash/status" | started |
| Device flash successful | "spark/flash/status" | success |
| Heartbeat every ## minutes | "msg" | See below table. |
| Bay 1 Empty | "msg" | bay1_empty |
| Bay 2 Empty | "msg" | bay2_empty |

Further, an example heartbeat event be associated with a timestamp and may include a delimited string reflecting various operation aspects of a scent dispenser 132. One such non-limiting example string may be "1,2,99999999,200,200,100,100,100,255:255:255,100,100,200,200", where the delimited values may have the following meaning:

| Description | Short Description | Type (int, double, string) | Range/unit | Example max char |
|---|---|---|---|---|
| Package Version # | version | integer | 1-9 | 1, |
| Heating element state | heaterState | integer | 0-2 (0 = none enabled, 1 = heater 1 enabled, 2 = heater 2 enabled) | 2, |
| Heating element duration (time heater has been active) (ms) | heaterDuration | integer | 1-99999999 (ms) | 99999999, |
| Slot/Bay 1 temperature | bayTemp1 | double | −50-200 | 200, |
| Slot/Bay 2 temperature | bayTemp2 | double | −50-200 | 200, |
| Slot/Bay 1 volume | bayVol1 | integer | 0-100 | 100, |
| Slot/Bay 2 volume | bayVol2 | integer | 0-100 | 100, |
| Ambient light | ambientLight | integer | 0-100 | 100, |
| Mood light state (rgb) | mLState | string | 255:255:255 | 255:255:255, |
| Slot/Bay 1 fragrance identifier | bayFID1 | integer | 0-999 | 999, |
| Slot/Bay 2 fragrance identifier | bayFID2 | integer | 0-999 | 999, |
| Slot/Bay 1 fragrance target temperature | bayTempTar1 | integer | 0-100 | 200 |
| Slot/Bay 2 fragrance target temperature | bayTempTar2 | integer | 0-100 | 200, |

In the above table, temperature is in Celsius, length is in millimeters (mm), duration is in milliseconds (ms), and time zone is any particular time zone (e.g., Mountain Time Zone (UTC-07:00)). Further, a fragrance identifier is a unique ID that corresponds to a specific type of scent solution, and a fragrance temperature is a temperature or range that a specific scent solution is heated to. Additionally, the scent dispenser 132 may be placed in various different operation states, such as but not limited to listening mode—for onboarding new credentials, safe mode—for development, DFU mode—for development, and connected—for normal operation.

In some embodiments, the scent dispenser 132 may support various functions, calls for which may originate from other devices of the system 100, such as the dispenser management application 160. Two non-limiting example functions may include command and tune:

int command(String operation); and int tune(String operation), where the tune function may use the format "TunableParameter,[value]" for the operation parameter. In this example, [value] is a positive integer. The scent dispenser 132 may respond with a ReturnCode if the request was received, such as:

```
enum ReturnCode {
    PURA_FAILURE = 0,
```

-continued

```
    PURA_SUCCESS = 1
};
```

Non-limiting example acts that may be performed using the above functions may include:

| Description | Function | String operation |
|---|---|---|
| Enables bay 1 heater | command | enableHeaterBay1 |
| Enables bay 2 heater | command | enableHeaterBay2 |
| Disables bay 1 heater | command | disableHeaterBay1 |
| Disables bay 1 heater | command | disableHeaterBay2 |
| Sets mood light RGB | tune | mLRGB, [value]:[value]:[value] |
| Sets mood light activation threshold | tune | mLThreshold, [value] |
| Sets bay fragrance identifier and temperature (*C.) | Tune | baySet, [value1], [value2], [value3]<br>Value 1: bay # (1 or 2)<br>Value 2: fragrance identifier<br>Value 3: fragrance target temperature |

Users may register with the scent service embodied by the dispenser management application 160, which enables them to remotely configure and interact with their respective scent dispensation installations 158, and to receive notifications automatically as state changes are detected by their scent dispensation installations 158.

The dispenser management server 150 includes a data store 170 storing various types of data used by the dispenser management application 160. Example data types include dispenser data 172, user data 174, fragrance data 176, usage data 178, premises data 180, and analytics data 182. The dispenser data 172 may include entries for the scent dispensers 132 in the system 100. A given entry may include a unique identifier for the corresponding scent dispenser, a firmware version, an operational status indicator (e.g., on, off, etc.), a schedule including which day(s) of the week and/or times of day the scent dispenser should be operating, which scent solution(s) should be dispensed during the scheduled timeframe(s), whether/which color light should be illuminated, the user identifier(s) with which the scent dispenser is registered, etc.

The user data 174 may include entries for the users 112 of the system 100. A given entry may include a unique identifier for the user, contact information for the user (e.g., address, phone number, electronic address (e.g., email)), payment information, scent subscription information specifying which reoccurring scent vials should be shipped to the user, historical scent vial purchase information, etc.

The fragrance data 176 may include entries for the different scent solutions that are supported by the system 100. An example entry may include a unique identifier for a given scent, a scent name, a scent description, a list of ingredients that comprise the scent's composition, an indication of the strength of a scent, room types for which to suggest the scent, etc.

The usage data 178 may include logged usage statistics received from the scent dispensers 132 deployed in the system 100. Example usage statistics may include hours of operation, which scent solutions where dispensed during those hours of operation, thus reflecting the time of day scent solutions were utilized, the amount of scent solutions that were dispensed as measured by vial sensors included in the scent dispensers 132, the rate at which the scent solutions were dispensed, etc. The usage statistics for a given scent dispenser 132 may be specifically associated with the user associated with the usage and/or a room of a premises in which the scent dispenser 132 is installed.

Further, the fragrance data 176 may include vial data including unique identifiers for each scent vial produced and registered for use in the system 100. The vial data may reflect the installation status of a vial, the unique identifier of the scent solution contained by the vial, and the fill level of the vial, an eligibility status, etc. For instance, the vial data for a particular vial may indicate whether the vial is new and has not yet been installed, that the vial is currently installed but has not yet been depleted of its solution, and that the vial was depleted of its solution and is no longer eligible for use.

The premises data 180 may include entries for different premises 140 in which scents dispensers 132 are installed. The premises data 180 may include different rooms 142 for the premises 140, and may indicate in which specific rooms 140 the scent dispensers 132 are installed. Example premises data may include unique identifiers for each of the premises, room names for each of the rooms of a given premises (e.g., which may be customized by the user), the dimensions of the rooms of the premises, an indication of which scent dispensers 132 are installed in which rooms of a given premises, for example, using the unique identifiers of the scent dispensers 132, etc., an indication of which unique user identifiers are associated with which unique premises identifiers, etc.

The analytics data 182 may include data produced by the dispenser management application 160 the data stored in the data store 170. For instance, data from the scent dispensers belonging to users 112 may be aggregated by the server in the data store 170 and then analyzed to generate analytics. These analytics can be used by the manufacturer to improve the product, the user to evaluate his/her usage, and the scent solution producers to learn more about their users, the users' habits and preferences, their products, etc.

Example analytics data may reflect scent preferences, such as which scents consumers use most often (e.g., based on the usage data 178 determined by a vial sensor), scent preferences by room type of the premises (e.g. floral for bathrooms, edible scents for kitchens, etc.) (e.g., based on the correlation between the fragrance data 176 and the premises data 180), which scents consumers are repurchasing the most (based on user data 174), whether or not consumers are mixing scents in specific rooms (e.g., based on the correlation between the fragrance data 176, the usage data 178, and the premises data 180), scent preferences by season (based on time/data coded usage data 178), preferences for strength of a scent (light vs. strong fragrance) and does that differ by room (e.g., based on the correlation between the fragrance data 176, the usage data 178, and the premises data 180), whether consumer scent preferences evolve over time (e.g., based on the usage data 178), preference for classic vs. novelty scents (e.g., based on the usage data 178 and the fragrance data 176 that tags each scent as classic or novelty), etc.

Example analytics data may reflect scent dispensation behaviors, such as how often users use their scent dispensers 132 (e.g., based on the usage data 178), is the use continuous or as needed (e.g., based on the usage data 178), how long is the continuous use (e.g., several hours, e.g., several days, etc., based on the usage data 178), how long does it take for consumers to change out a cartridge/refill (e.g., usage data reflects an empty vial stayed in the scent diffuser 132 for a certain timeframe, which can be averaged over many, or all users (e.g., generally, for that fragrance type, etc.)), how often are consumers purchasing refills (e.g., based on the user data 174 reflecting purchase history), preferred rooms for using scent dispenser 132 (e.g., based on the correlation between the usage data 178 and the premises data 180), use of scent dispensers 132 when users 112 are in vs. out of the premises 140 (e.g., based on the correlation between the users' 112 user data 174 and the usage data 178), etc.

Example demographics data may reflect behaviors and preferences by different demographic groups. User data may reflect a user's gender, age, income, race/ethnicity, number of children in the home, number of pets in the home, region, settlement-type (urban, rural, suburban, etc.), premises type (single family home, apartment, condo, townhouse, small business, large business, hotel, bed and breakfast, warehouse, restaurant, etc.), personal or business, etc. Using the user data, any of the other data or combinations thereof may be segmented to determine which groups may be more or less predisposed to scent dispensation, and how different factors affect the level of scent dispensation by a particular group.

Figure 26:
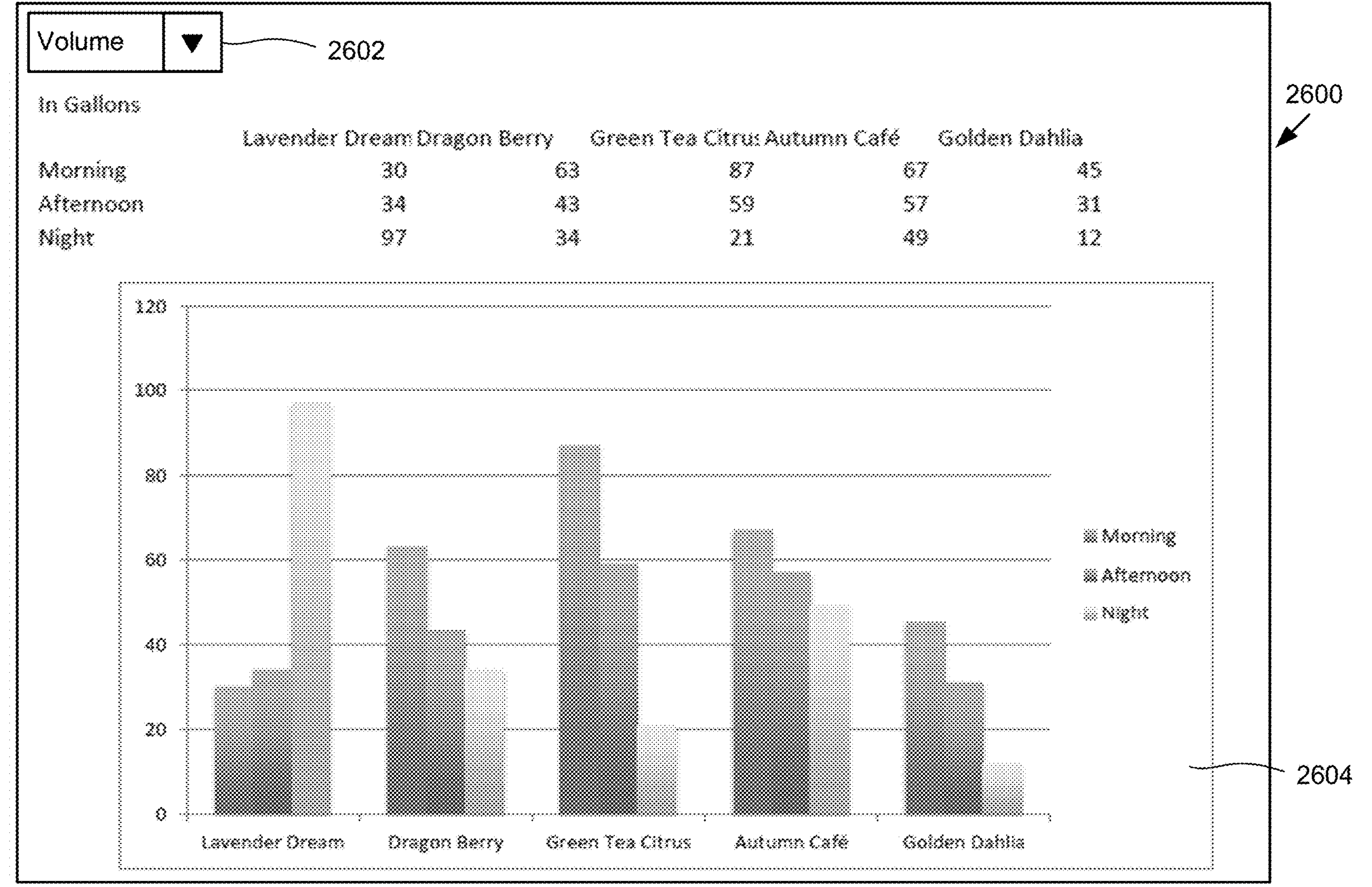
FIGS. 26-27B are graphical representations of example user interfaces for display and receiving user interaction with scent analytics.

The data stored by the data store 170 may be correlated using various common keys, such as unique identifiers (e.g., user identifiers, room identifiers, fragrance identifiers, scent dispenser identifiers, vial identifiers, room identifiers, premises identifiers, etc.), which allow the dispenser management application 160 to generate and provide rich analytics. Example graphical representations that may be rendered for display on a computing device 106 of a user 112 are depicted in FIGS. 26-27B. In particular, FIG. 26 illustrates an example graphical user interface 2600 including a digital data visualization 2604 showing usage statistics for different scent solutions (e.g., lavender dream, dragon berry, green tea citrus, autumn café, golden dahlia).

In some embodiments, the statistical data used to generate the digital data visualization 2604 is received from a multiplicity of scent dispensers 132 installed in different premises in the system. The vial sensors of the scent dispensers 132 detect the changes in the fluid levels of the vials as the solutions from the vials are diffused into the air of the respective premises 140. The controllers of the scent dispensers 132 receive the data reflecting the changing fluid levels and transmit that data to the dispenser management server 150, which in turn stores the data as usage data 178 in the data store 170 in association with the scent/fragrance ID to which the data corresponds. As a result, the usage data 178 reflects the amount of each scent solution that is consumed over time for each scent dispenser 132 relative to the user ID, the premises ID, the room ID, scent dispenser 132 ID, the vial ID associated with that particular scent solution (e.g. which is identifiable as discussed elsewhere herein).

Figure 27A:
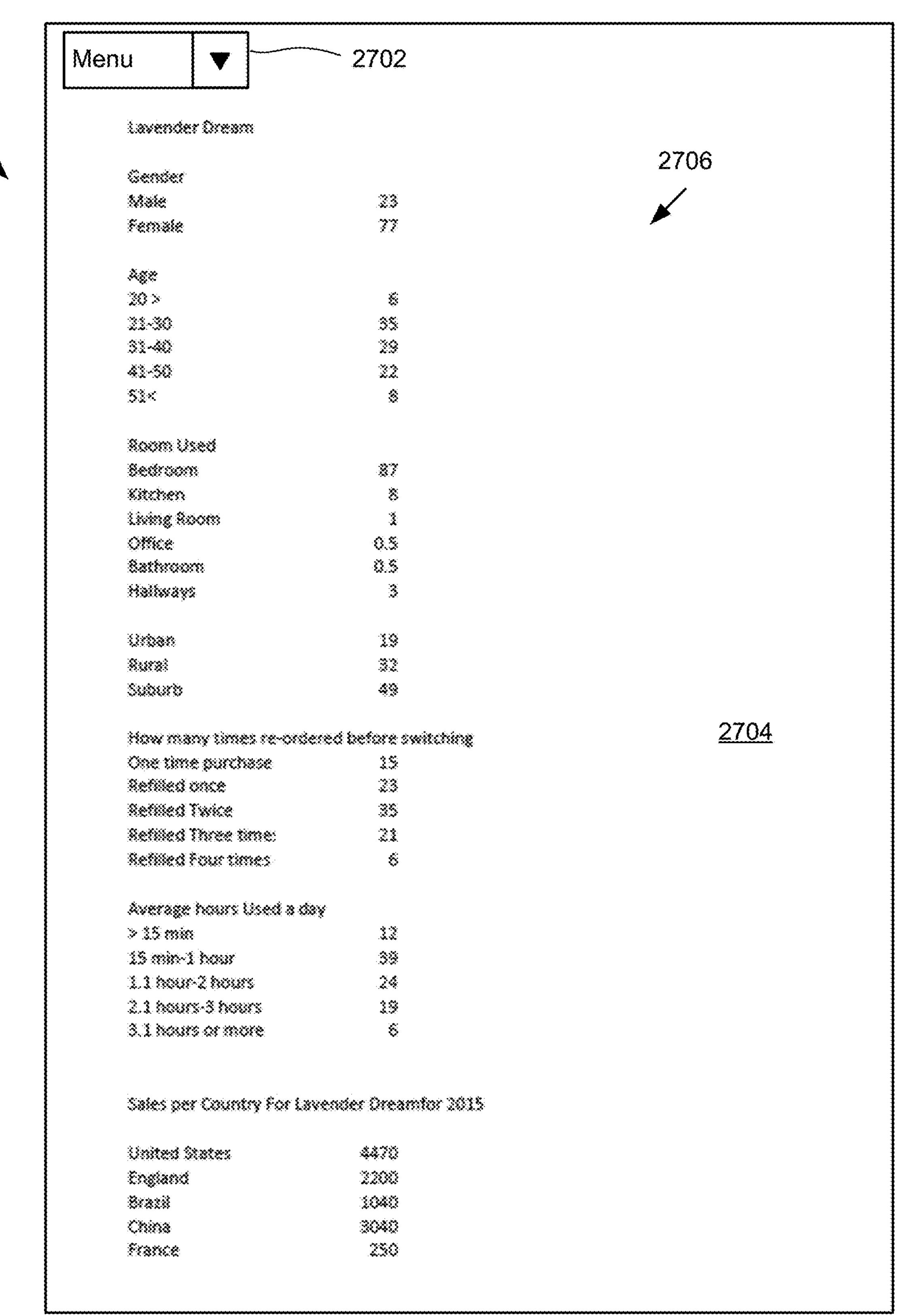
Figure 27B:
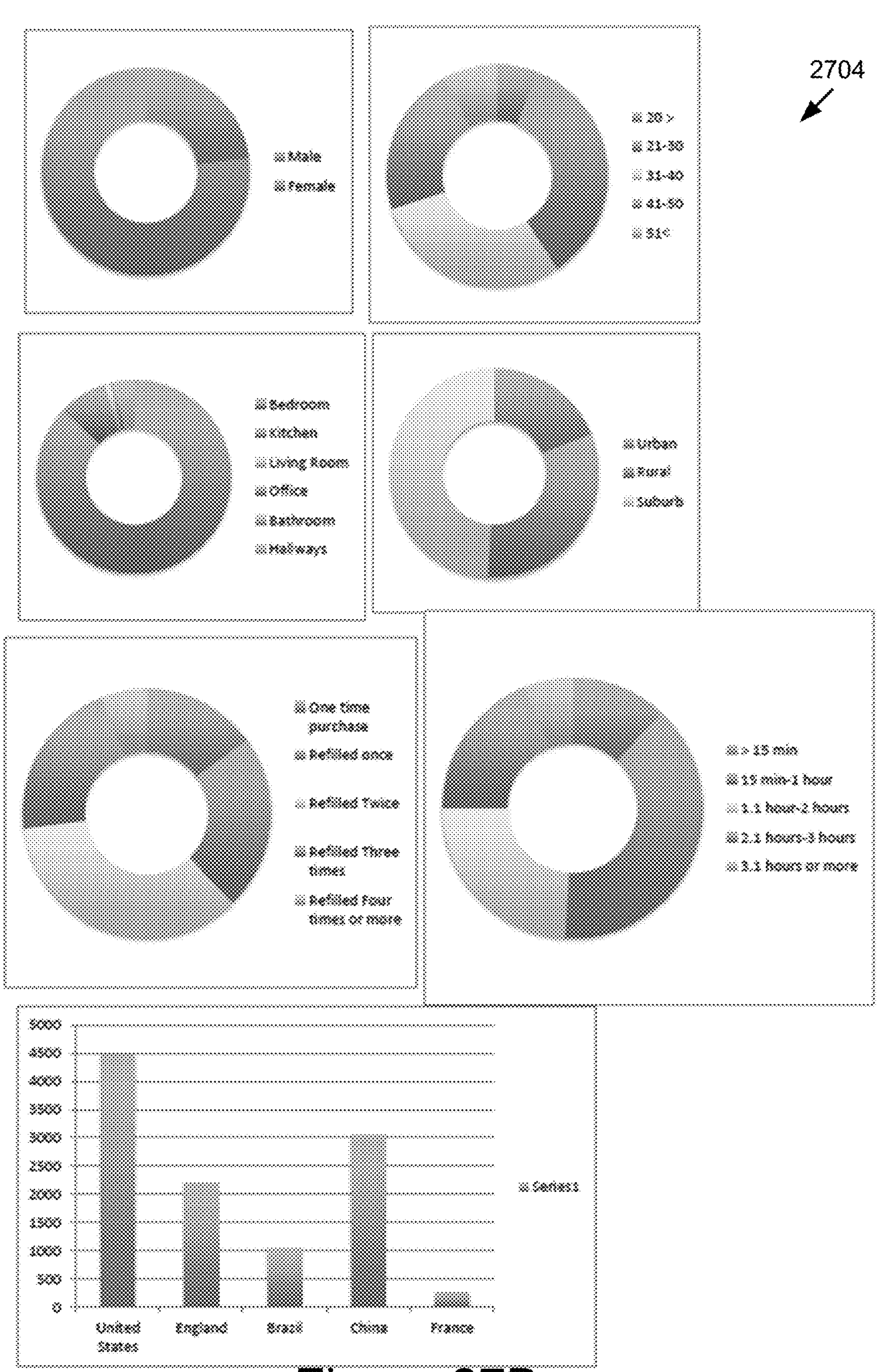

FIGS. 27A and 27B are graphical representations of further graphical user interface 2700 for displaying and providing user interaction with scent analytics. As shown, the graphical user interface 2700 includes usage statistics 2706 for a particular scent solution (e.g., lavender dream), including segmentation by gender, age, room type, settlement-type. The statistics 2706 include information on how many times that particular scent solution was reordered before switching to another scent solution (e.g., refilled in this case means the vial was switched out for a new vial in the users' 112 scent dispensers 132), as well as the average hours the scent solution was used each day by the users 112 who have the scent solution installed in their scent dispensers 132. The graphical user interface 2700 includes a corresponding set of digital data visualizations 2704 that correspond to the usage statistics, as shown in FIG. 27B.

Figure 1B:
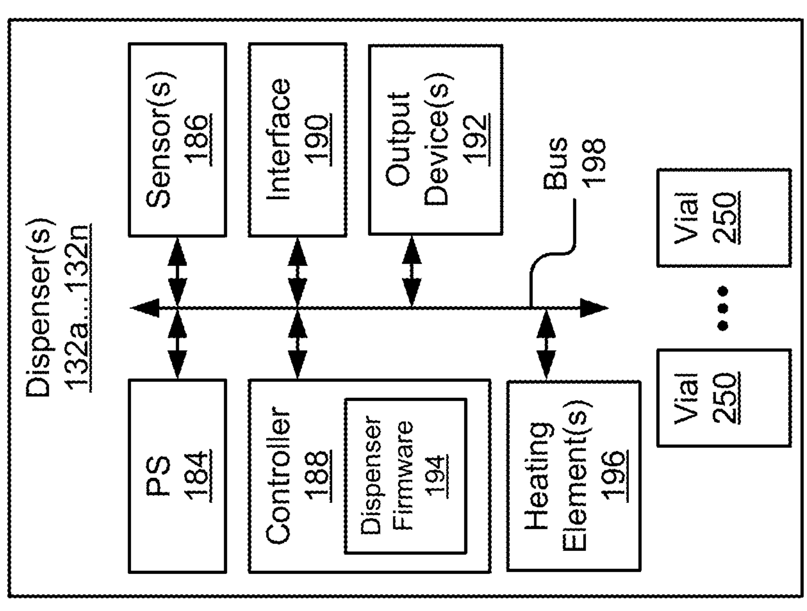
FIG. 1B is a block diagram illustrating an example scent dispenser.

FIG. 1B is a block diagram illustrating an example scent dispenser, which is depicted as including a power supply (PS) 184, a set of sensors 186, a controller 188, an interface 190, output device(s) 192, dispenser firmware 194, heating element(s) 196, and any number of vials 205*a* . . . 205*n* (individually or collectively also referred to as simply 205). The components 184, 186, 188, 190, 192, and 196 are communicatively coupled via a communications bus 198. The controller 188 may include a non-transitory memory device, or may be coupled to a non-transitory memory device also coupled for communication via the bus 198. The non-transitory memory device may store software that specially configures the controller, such as the dispenser firmware 194. The PS 184 may be any AC and/or DC power supply for powering the scent dispenser 132. The controller 188 is a microchip that controls the constituent electronics (e.g., sensor(s) 186, output device(s) 192, interface 190, heating element(s) 196, etc.) of the scent dispenser. A non-limiting example of the controller 188 may include an ARM-based microcontroller, such as one manufactured by Mouser Electronics under PN P1REEL, although it should be understood that other chip architectures are also applicable, that the controller 328 may be combined with other processors, and/or that numerous other variations are possible, contemplated, and applicable.

The set of sensor(s) 186 may include a vial sensor for sensing the fill level of the vial(s) 250 installed in the scent dispenser 132, optical sensor(s) for detecting an identity of vial(s) installed in the scent dispenser 132, temperature sensors (e.g., thermocouples, etc.) for sensing the temperature of the heating element(s) 196, ambient light sensor to detect a light level in a surrounding environment (e.g., room), and/or a motion sensor to detect motion in the surrounding environment, etc.

In some embodiments, the sensors 186 may include a temperature bay sensor for each heating element 196 (e.g., that may measure temperatures ranging from (−50 to 200 degrees Celsius), the vial sensor 300 (e.g., see FIG. 3A), an ambient light sensor, etc.). The heating element 196 may be configured to heat to any suitable temperature sufficient to diffuse a scent solution contained in a corresponding vial 250, a non-limiting example of which may be 65 degrees Celsius, and the temperature bay sensor 186 may be mounted on or adjacent to, or embedded in, the heating element 196 to measure the temperature of the heating element 196 and provide feedback to the controller 188, which may cyclically heat the heating element 196 based on the feedback to maintain a constant or substantially constant temperature during diffusion (as set in the state settings).

The sensors 186 include a transceiver having a wireless interface configured to communicate with the devices coupled to the network 102, such as the access point 120, the dispenser management server 150, and/or other components of the network 102 using standard communication protocols, such as Internet protocols. Further, the transceiver may be configured to wirelessly transmit data via a meshwork network made up of a plurality of scent dispensers 132 and/or other devices, such as the access point 120 or a mobile device 106. By way of further example, the transceiver may transmit data to the access point 120 to which it is linked using a protocol compliant with IEEE 802.15, such as Zigbee®, Z-Wave®, Bluetooth®, or another suitable standard. Additionally or alternatively, one or more of the scent dispenser(s) 132 and/or the access point 120 of an installation 158 may be wired for direct communication and the wired components may exchange data using wired data communication protocols. Further embodiments are also possible and contemplated. In some embodiments, the transceiver may be embedded in the controller 188 or may be a component distinct from the controller and coupled to the controller 188 via the bus 198.

The output device(s) 192 may include light sources and/or audio reproduction devices, although further suitable output devices are also contemplated and applicable. The light sources and/or audio reproduction devices may be controlled to produce output consistent with a scent being emitted by the scent dispenser (e.g., a low, soothing light and music may be output in conjunction with a relaxing scent being emitted).

Returning to FIG. 1A, the client device(s) 106 (also referred to individually and collectively as 106) are computing devices having data processing and communication capabilities. In some embodiments, a client device 106 may include a processor (e.g., virtual, physical, etc.), a memory, a power source, a network interface, and/or other software and/or hardware components, such as a display, graphics processor, wireless transceivers, keyboard, camera, sensors, firmware, operating systems, drivers, various physical connection interfaces (e.g., USB, HDMI, etc.).

The client devices 106 may couple to and communicate with one another and the other entities of the system 100 via the network 102 using a wireless and/or wired connection. Examples of client devices 106 may include, but are not limited to, mobile phones (e.g., feature phones, smart phones, etc.), tablets, smartwatches or other smart wearables, laptops, desktops, netbooks, server appliances, servers, virtual machines, TVs, set-top boxes, media streaming devices, portable media players, navigation devices, personal digital assistants, etc. In addition, while a single client device 106 is depicted in FIG. 1, it should be understood that any number of client devices 106 may be included.

As shown, the client device 106 may include a scent application 108, which allows the user to set scent dispenser 132 settings, turn scent dispensers 132 on and off, purchase vials for the scent dispenser 132, set up a scent dispenser 132, register an account, set up a premises and the rooms of the premises, associate a scent dispenser 132 with a particular room of the premises, view analytics reflecting the user's historical use of his/her scent dispenser(s) 132, enable user profiles to use and setup scent profiles for the scent dispenser(s) installed in the premises, set a profile hierarchy (e.g., set which user profile(s) is/are the dominant user profile), etc.

The client device 106 may store the scent application 108 in non-transitory memory, retrieve the scent application 108 from memory, and execute instructions comprising the scent application 108. The scent application 108, when executed by a processor of the client device 106, configures the processor of the client device 106 to carry out the acts and functionality described herein. In some embodiments, the scent application 108 may render and display various interfaces for carrying out the functionality described herein, such as but not limited to those depicted in FIGS. 14A-20B.

Figure 14B:
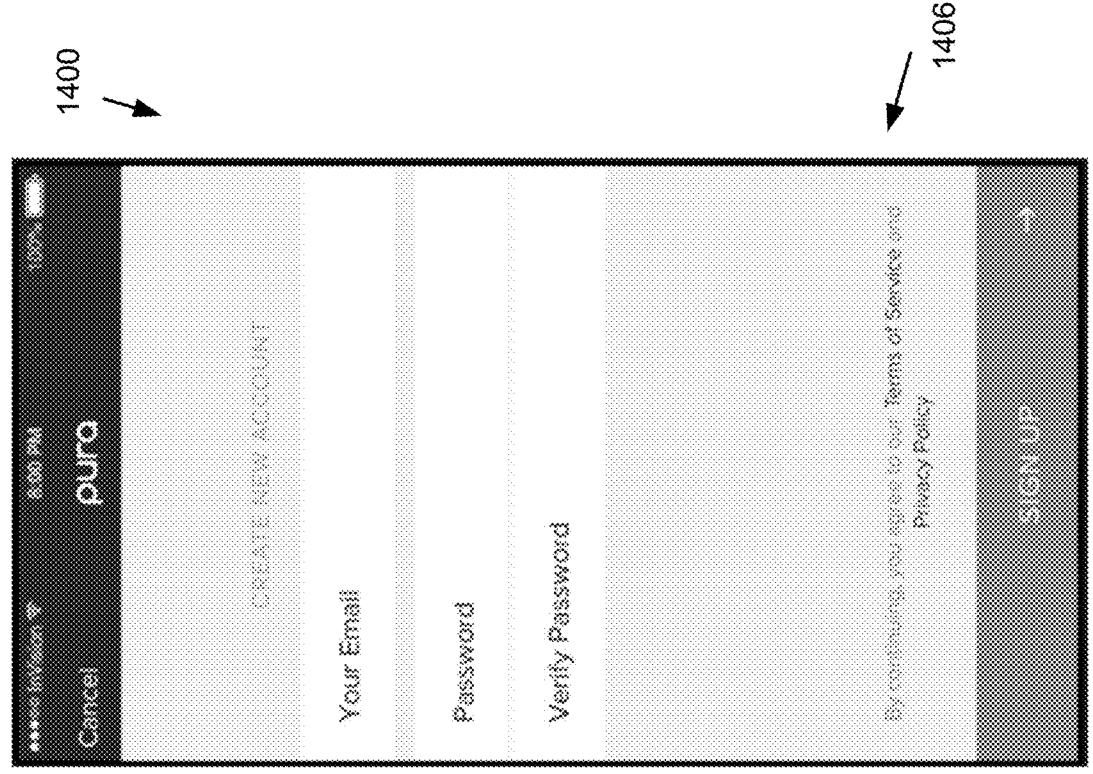
Figure 14A:

In particular, FIGS. 14A-14H are graphical representations of user interfaces for setting up a scent dispenser 132. For instance, FIGS. 14A and 14B depict the user interface 1400 for logging into and/or registering an account with the scent service. The user may enter his/her credentials (e.g., email and password) in the fields 1402 or 1406, may select corresponding interface elements (e.g., sign in or sign up) to submit the credentials depending on whether the user is logging into an existing account or creating a new account. Upon submission of the form fields, the scent application 108 may transmit the credentials to the dispenser management application 160 and authenticate instance of the scent application 108.

Figure 14D:
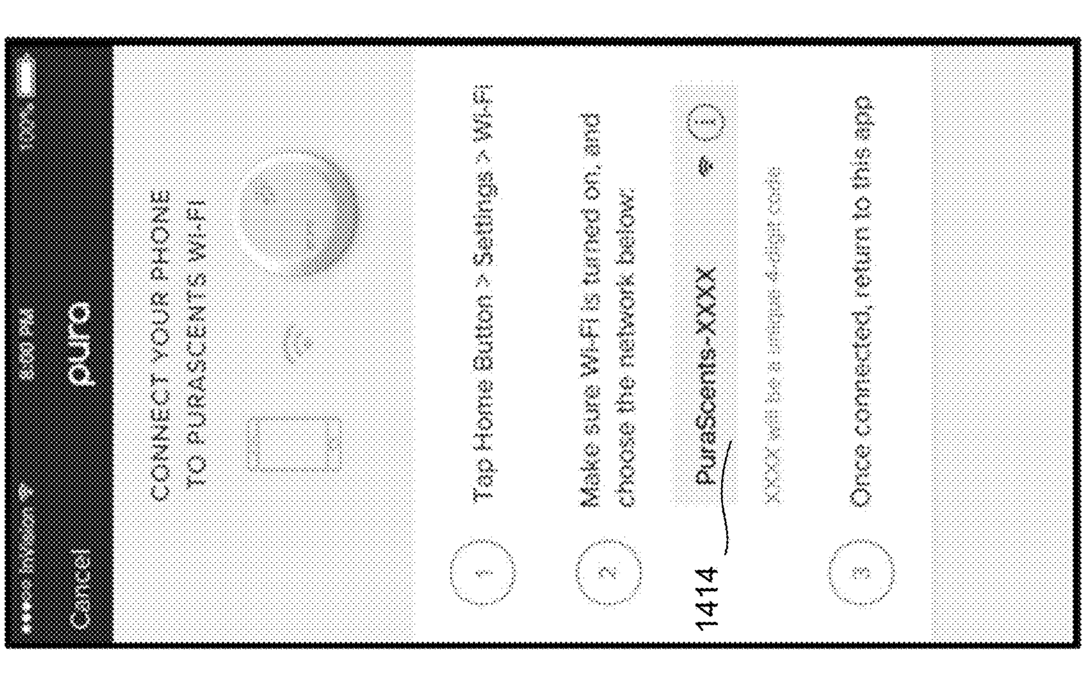
Figure 14C:
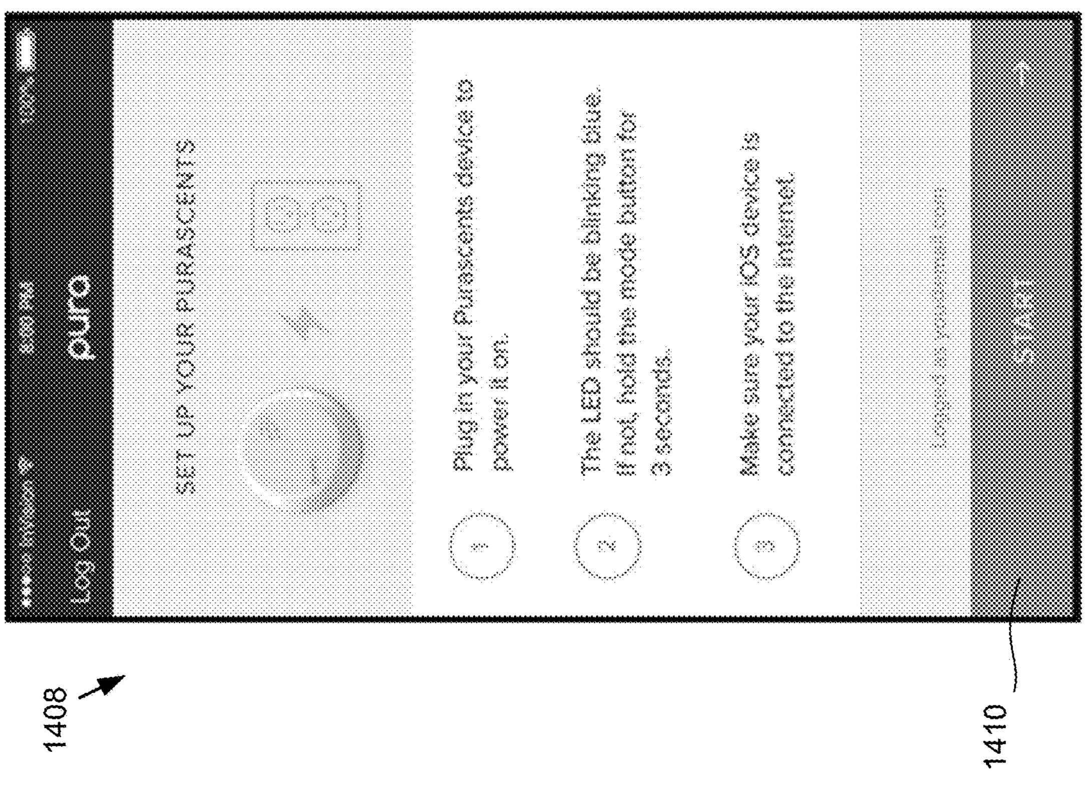
Figure 14F:
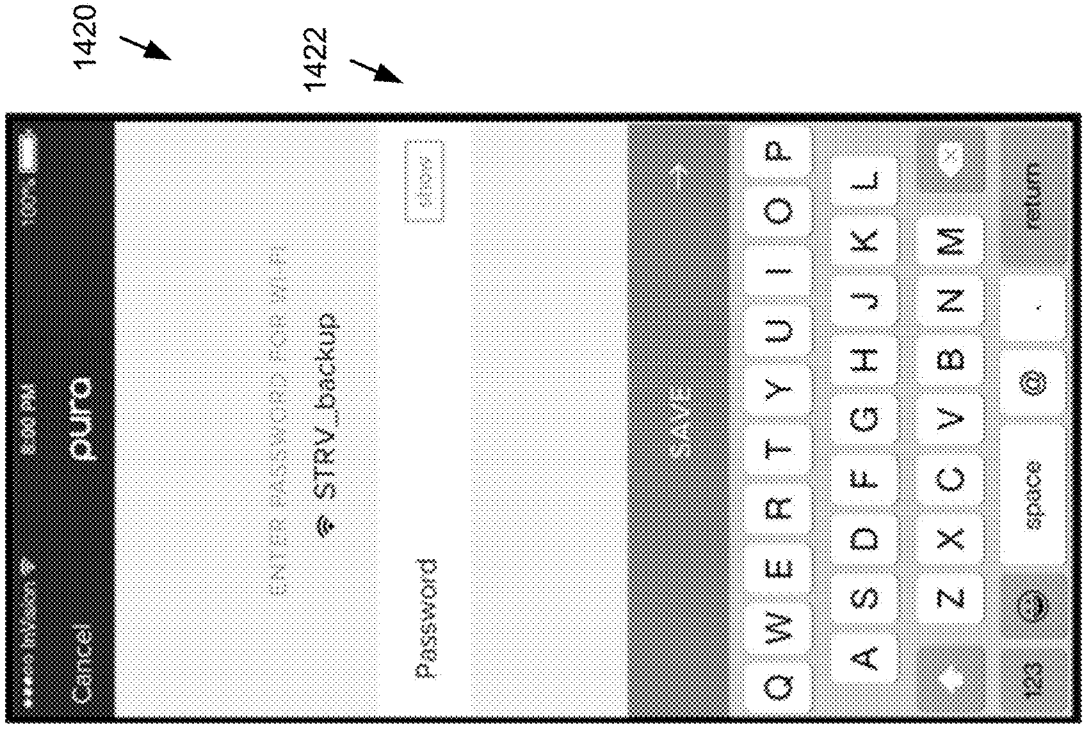

Upon receiving a response from the dispenser management application 160 that the authentication is successful, the scent application 108 may proceed to display the user interface 1408 depicted in FIG. 14C, which includes a summary of the steps for setting up a scent dispenser 132 and a user interface element 1410 for beginning the setup process, which is selectable by the user. Upon following the instructions (e.g., plugging in the scent dispenser 132), and selecting the element 1410, the scent application 108 displays user interface 1412, which includes instructions prompting the user to connect his/her user device 106 (e.g., mobile phone) to a wireless network broadcasted by the scent dispenser 132. An unregistered scent dispenser 132, when first plugged into an electrical socket, proceeds through a boot sequence of the default firmware stored in the memory of the scent dispenser 132. As part of the boot sequence, the firmware determines that the scent dispenser has not yet been initialized and proceeds to broadcast a wireless network via which the user connects his/her user device and the user can configure the scent dispenser 132.

In some embodiments, when a scent dispenser 132 is booted, it registers its functions with the dispenser management application 160, and may resume the device's last previously known state. If the state is unknown the heating elements 196 may be are disabled. In some embodiments, if the state is different from what the controller 188 may programmed to expect (e.g., a scent volume has changed significantly), an alert may be published and the heating elements 196 may be disabled. In some embodiments, when the scent solution of a vial is depleted (e.g., drained to the lowest detectable level) the heating element 196 may be disabled and an event may be published to the dispenser management application 160, which may in turn, send a notification to the client device 106 of that user (which may be registered in the usage data for the user of that scent dispenser 132) to notify the user that the scent has run out and is no longer being diffused, as well as provide an option for repurchase.

Figure 14E:
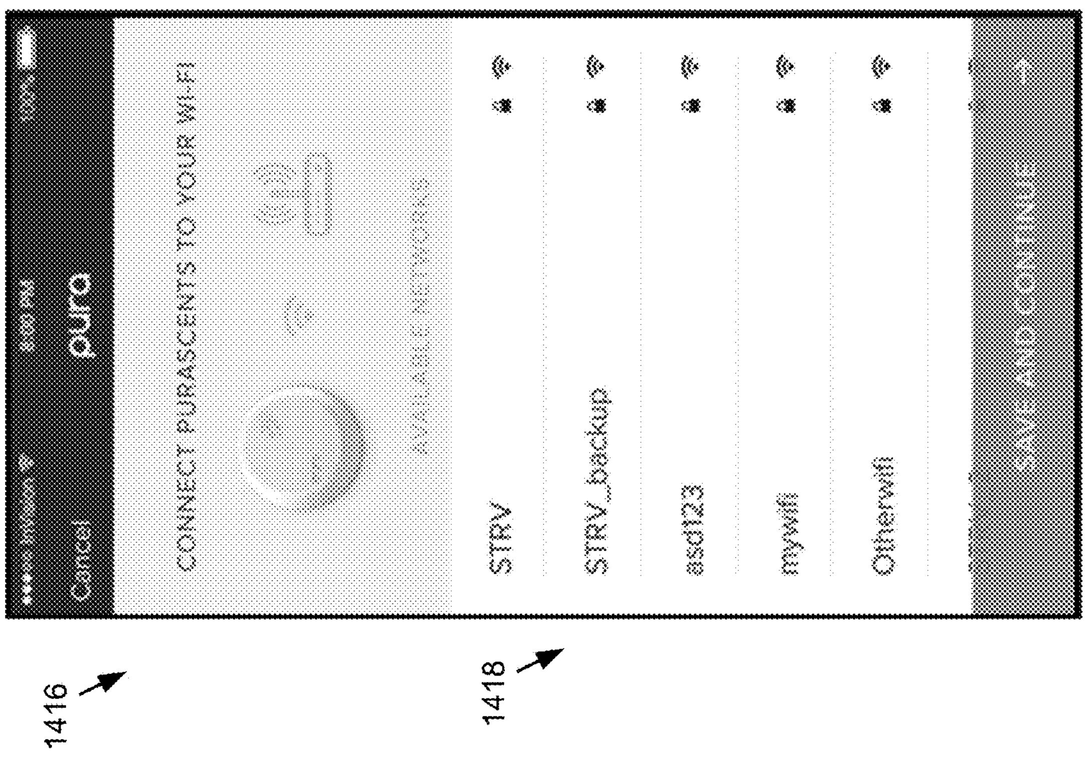

As shown in FIG. 14D, the user may select the network broadcasted by the scent dispenser 132 using user selectable element 1414 of the user interface 1412, and upon successfully connecting to the network, may proceed to configure the scent dispenser 132. In FIG. 14E, the user interface 1416 includes a list of user selectable networks accessible in the location which the user stands and is presumably associated with the premises in which the scent dispenser 132 is installed. Upon selecting one of the networks from the list 1418, the scent application 108 displays user interface 1420, which includes a set of user interactable elements such as a password entry field and a save button. Upon entering the password and selecting save, the scent application 108 transmits data describing the selected wireless network and password to the scent dispenser 132 via the wireless network broadcasted by the scent dispenser 132, and the firmware stores the data for that wireless network in the memory of the scent dispenser 132, the proceeds to connect the scent dispenser 132 to that selected wireless network. Upon successfully connecting to the network, the firmware may run other checks such as verifying that the scent dispenser 132 can connect to the dispenser management server 150 via the network, and can register that dispenser 132 to the user. The dispenser management application 160 may receive the configuration information entered via the interfaces depicted in FIGS. 14A-14E and may store that information as user data 174 in the data store 170. The user interface 1424 depicted in FIG. 14G includes graphical user interface elements showing the completed and yet to be completed steps involved in the configuration. The user interface 1426 depicted in FIG. 14H includes information confirming successful registration of the scent dispenser 132, and includes a user selectable interface element 1430 for installing one or more scent vials in the scent dispenser 132.

Figure 15B:
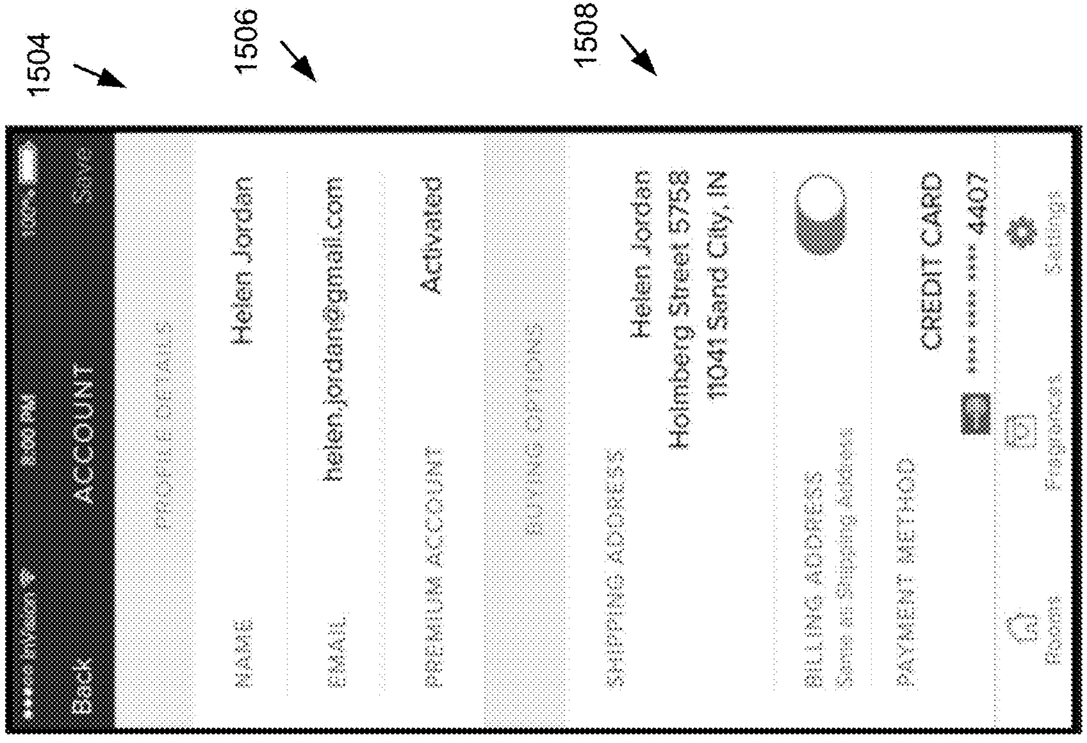
FIGS. 15A-15H are graphical representations of user interfaces for configuring vial settings of a scent dispenser.
Figure 15A:
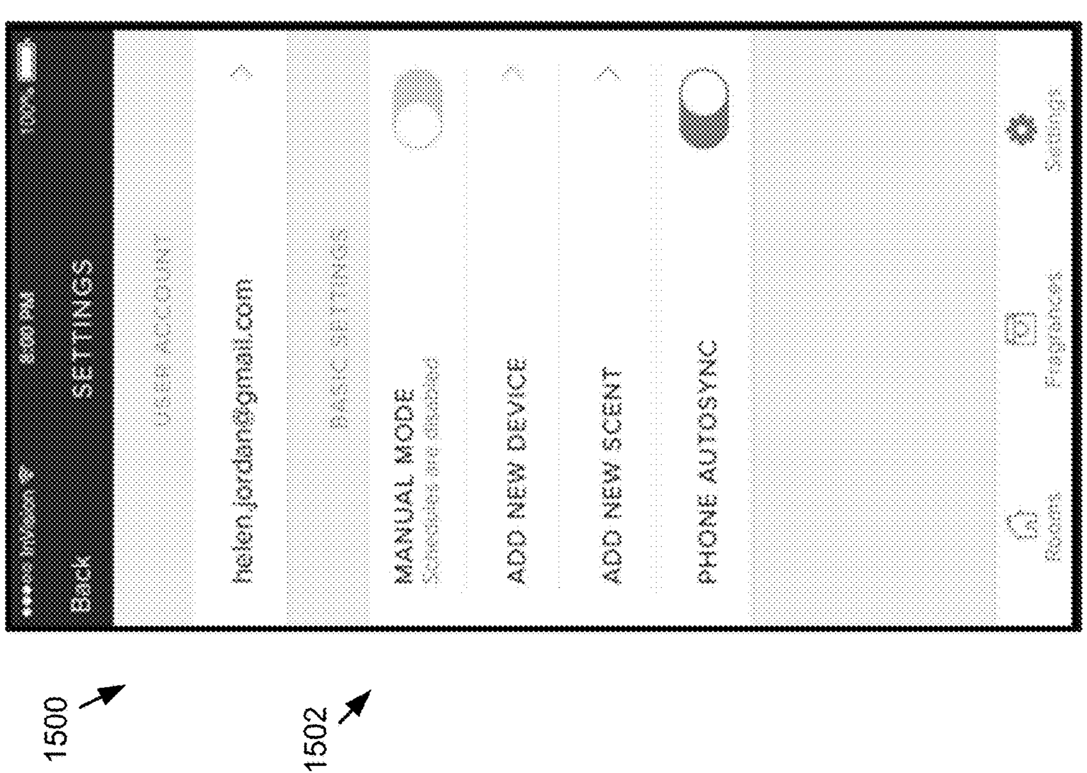

FIGS. 15A-15H are graphical representations of user interfaces for configuring vial settings of a scent dispenser. For example, FIG. 15A depicts a user interface 1500 including a set of user selectable interface elements for user account settings. For example, a user may select to disable all schedules and manually turn on and off the scent dispensers 132 registered with the user's account using the scent application 108. Alternatively, the user may select to enable the schedules (which may be configured using other interfaces, such as those described elsewhere herein). The user may also select to add a new scent dispenser 132, add a vial 250 to a scent dispenser 132, replace a vial 250 with another vial 250 in the scent dispenser 132, and enable a geofencing option as described elsewhere herein. Upon changing the user account settings, the scent application 108 may transmit user data reflecting the changes to the dispenser management server 150, and upon receipt thereof, the dispenser management application 160 may update the user data associated with the user to reflect the revised settings. The settings associated with the user and his/her scent dispenser(s) 132 may also be referred to herein as a user profile, and may be stored as user data 174. The scent vial configuration (e.g., which fragrance types and/or specific vials are installed in a given scent dispenser 132 or set of scent dispenser(s) 132) may also be referred to herein as a scent profile of that/those scent dispenser(s) 132, and may be stored as dispenser data 172.

FIG. 15B depicts a user interface 1504 displayed by the scent application 108 that includes user configurable interface elements 1506 for revising the user's personal information and/or account type, and user configurable interface elements 1508 for inputting address and payment information.

Figure 15D:
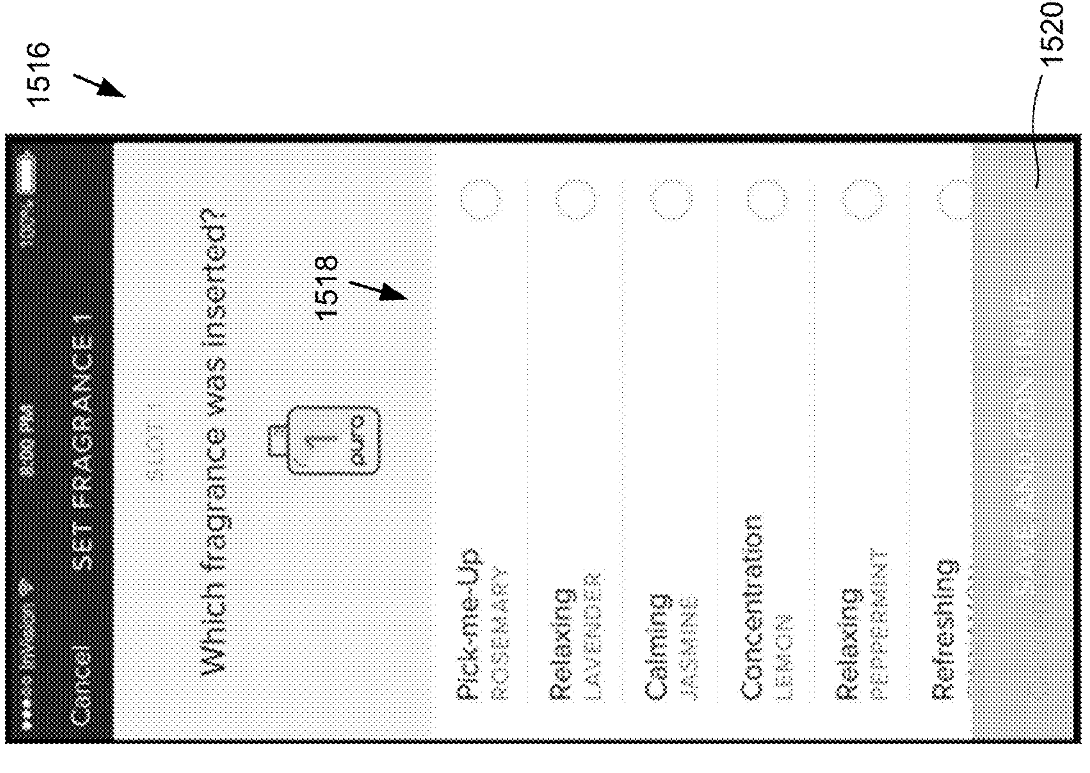
Figure 15C:
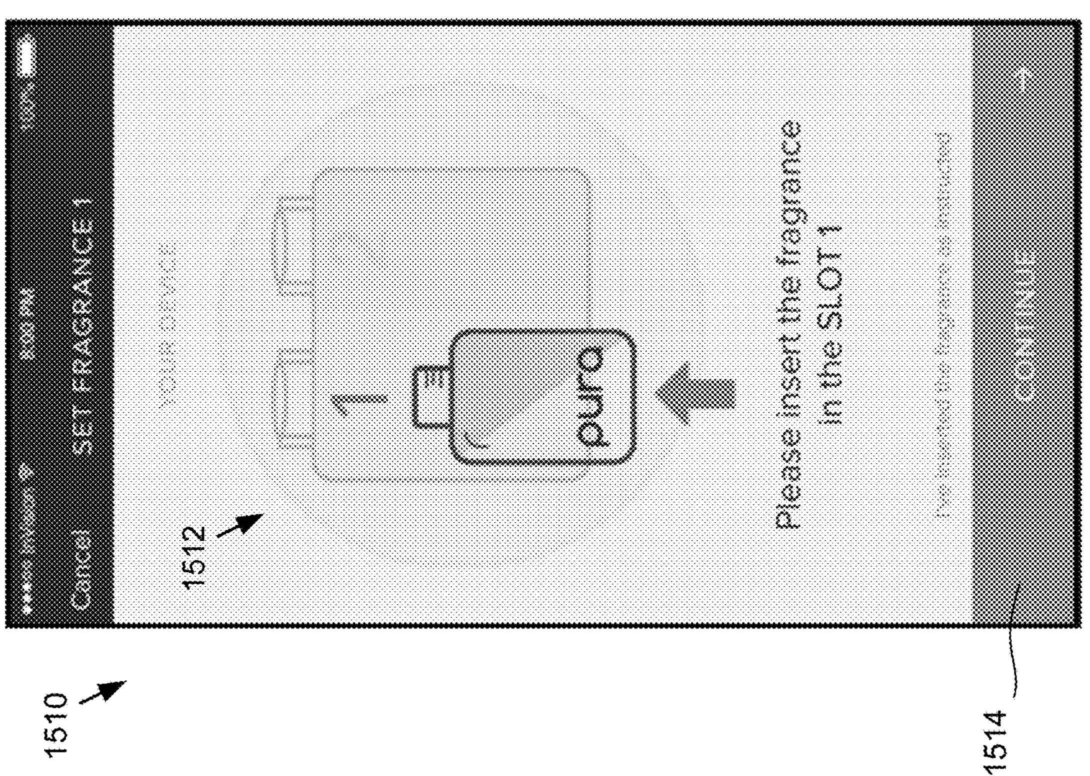

FIG. 15C depicts a user interface 1510 displayed by the scent application 108 for installing a scent vial 250 into a first slot of a selected scent dispenser 132 registered to the user. The user interface 1510 instructs the user to insert the scent vial 250 into the first slot (e.g., slot labeled 1, slot on left, etc.), and upon doing so, select the user selectable interface element 1514 to continue the installation process. Next, the scent application 108 displays user interface 1516, as depicted in FIG. 15D, which includes a user selectable list 1518 of available scents and requests the user to select which scent the user installed into the first slot. Upon confirmation of the type of scent the user selected by selecting the user interface element 1520 configured for confirming the selection (e.g., save and continue), the scent application 108 transmits the installation information to the dispenser management application 160, which then stores the scent dispenser 132 information in the data store 170 (e.g., as dispenser data 172, and user data 174, etc.) in association with the user's user ID and the scent dispenser's 132 device ID.

Figure 15F:
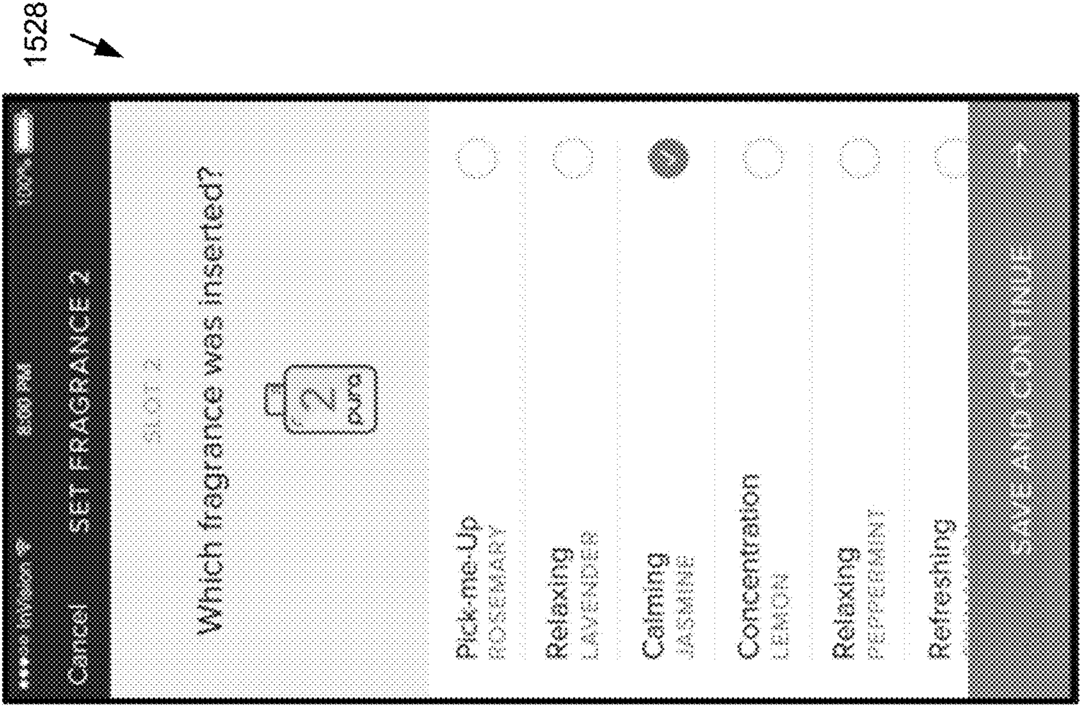
Figure 15E:
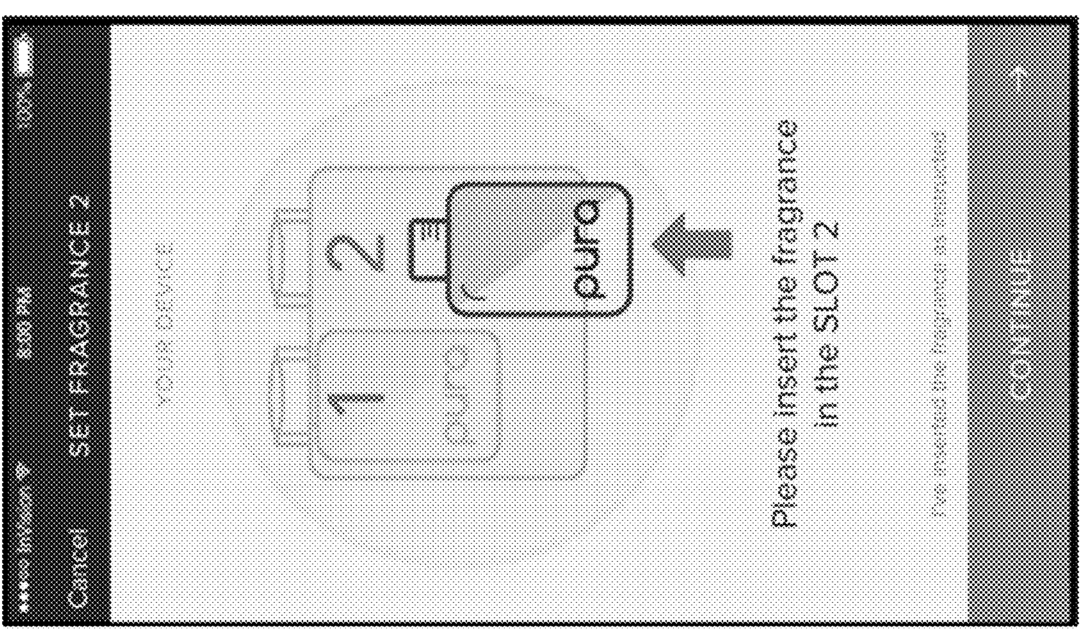
Figure 15E:

FIGS. 15E and 15F depict user interfaces 1522 and 1528 for installing additional vial(s) in the scent dispenser 132 (e.g., in the second slot). The content and the functionality of the interfaces 1522 and 1528 are substantially similar to those described with respect to FIGS. 15C and 15D and will not be repeated here. It is noted that, once installation is complete and the second vial type is saved, the scent application 108 may transmit the installation information to the dispenser management application 160 for storage in a manner substantially similar to that described with respect to FIGS. 15C and 15D.

Figure 15H:
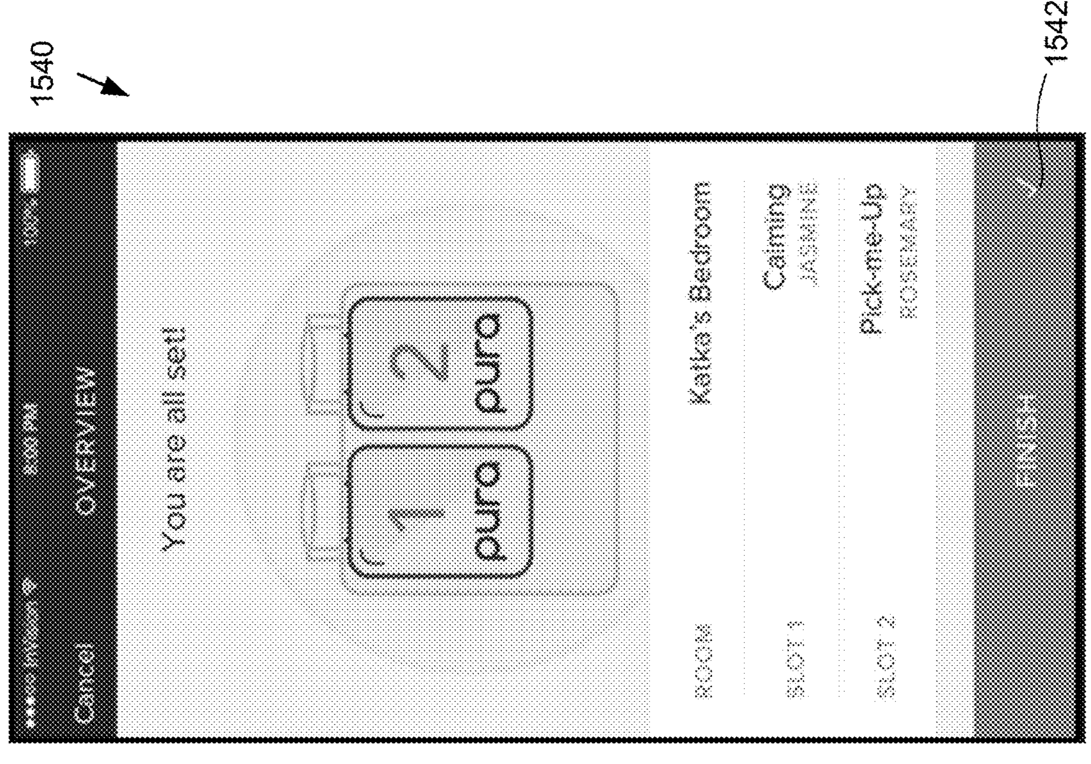
Figure 15G:
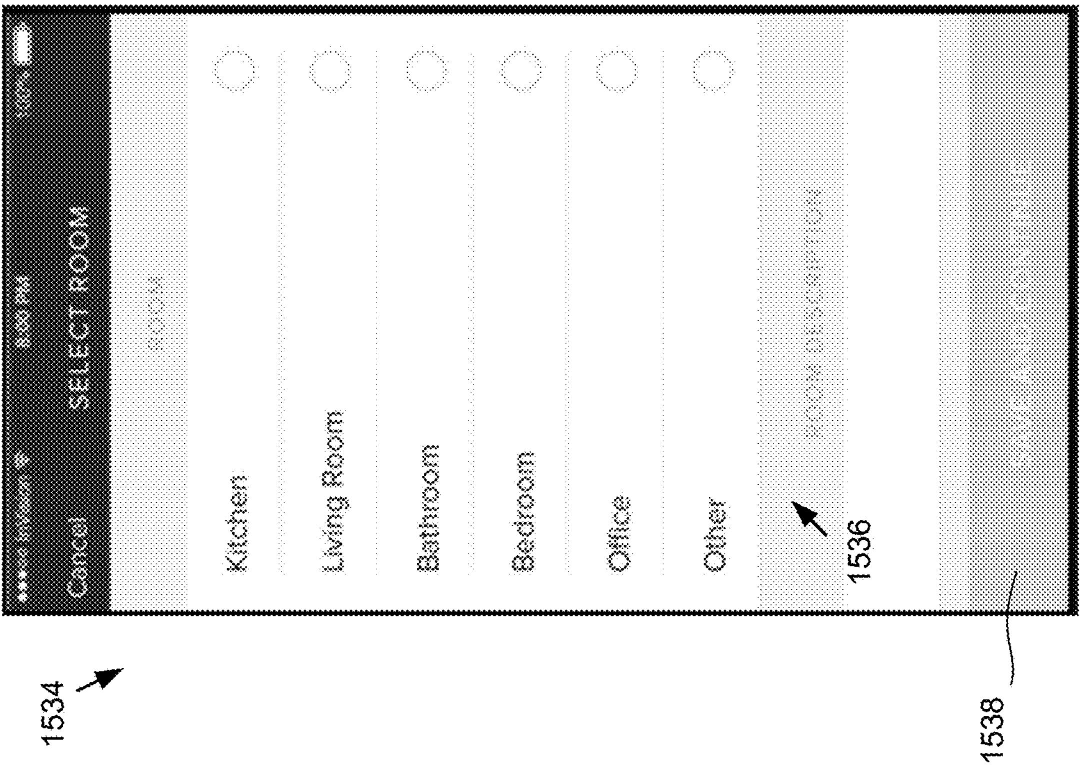

FIG. 15G depicts a user interface 1534 for associating the scent dispenser 132, and thus the scent types installed in the scent dispenser 132, and in some cases, the specific identities of the first vial 250 and/or second vial 250, with a particular room of the premises. The interface 1534 may include a user selectable list 1536 of rooms as well as a field for entering a custom room description for the room that the user selected from the list 1536. Upon selecting interface element 1538 (e.g., save and continue), the scent application 108 may transmit installation data reflecting the room of the premises in which the scent dispenser 132 is installed. The dispenser management application 160 may receive and store this data in the data store 170 (e.g., as premises data 180, etc.) in association with the scent dispenser ID, the premises ID, and/or the room ID, etc.

FIG. 15H depicts a user interface 1540 to confirm that the installation process for installing the vial(s) in the scent dispenser 132 is complete, which includes a list of information about the installation, such as the room in which the scent dispenser 132 is installed, and identify information about the scent installed in the scent dispenser 132. The user may exit the installation process by selecting the user interface element 1542.

Figure 16D:
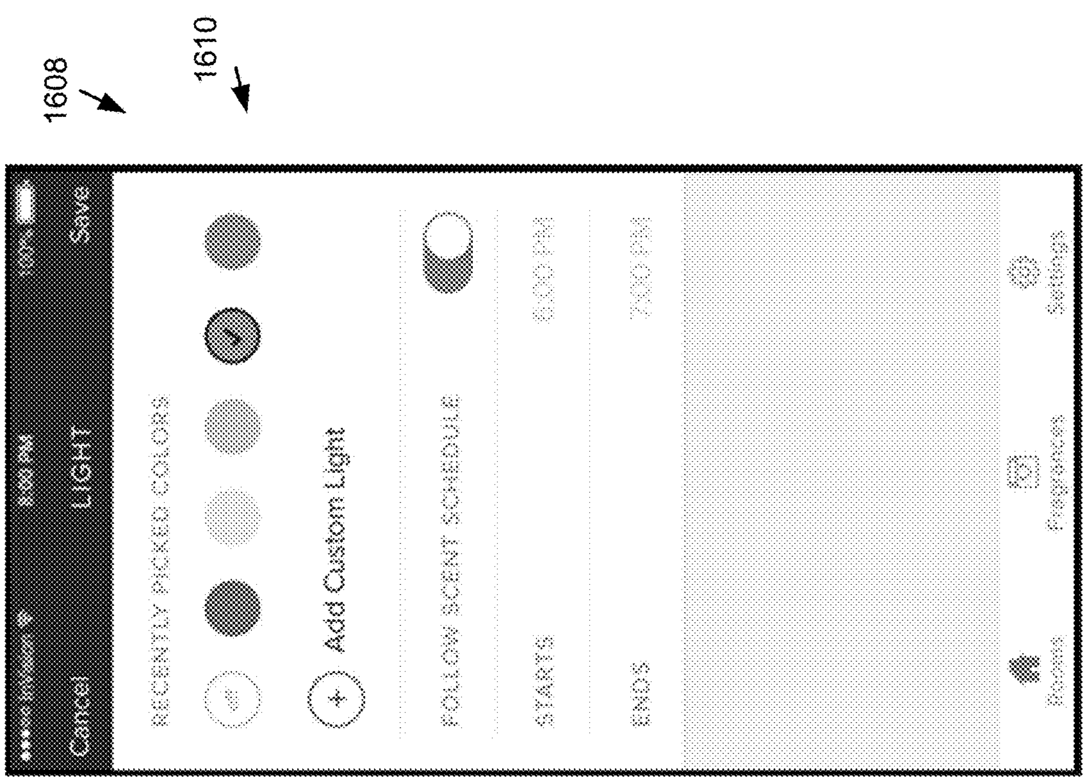
Figure 16C:
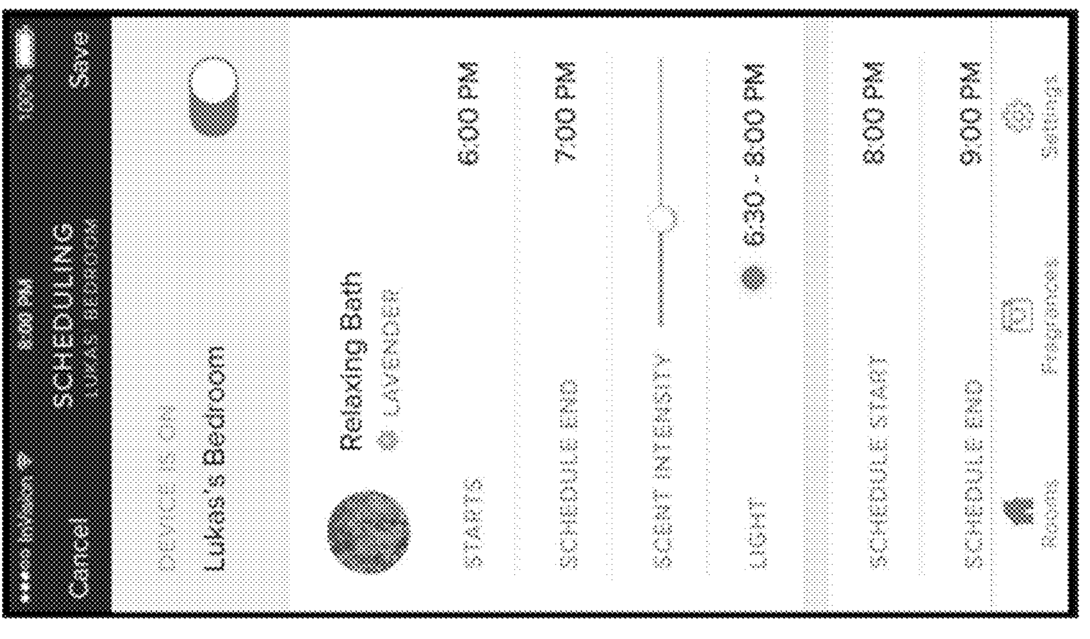

FIGS. 16A-16E are graphical representations of user interfaces for scheduling scent dispensation for one or more rooms. FIGS. 16A-16C depict the user interface 1600, which includes a set of user interface elements 1602 and 1604 that are user configurable to set a schedule for a scent dispenser 132. In particular, using the set of user interface elements 1602 and 1604, the user may activate the device, and select a start and end time for scent dispensation. Further, the user may adjust the scent intensity and select whether to illuminate the light of the sensor during scent dispensation, and select to add additional scent schedules to the device, such as a schedule of different time and/or day for an alternative scent, etc. While not depicted, the set of user interface elements 1602 may also include a day calendar from which the user may select particular days of the month in which to schedule the scent dispensation. The user may select a one-time schedule or reoccurring schedule using the interface elements 1602 and 1604.

Figure 16E:
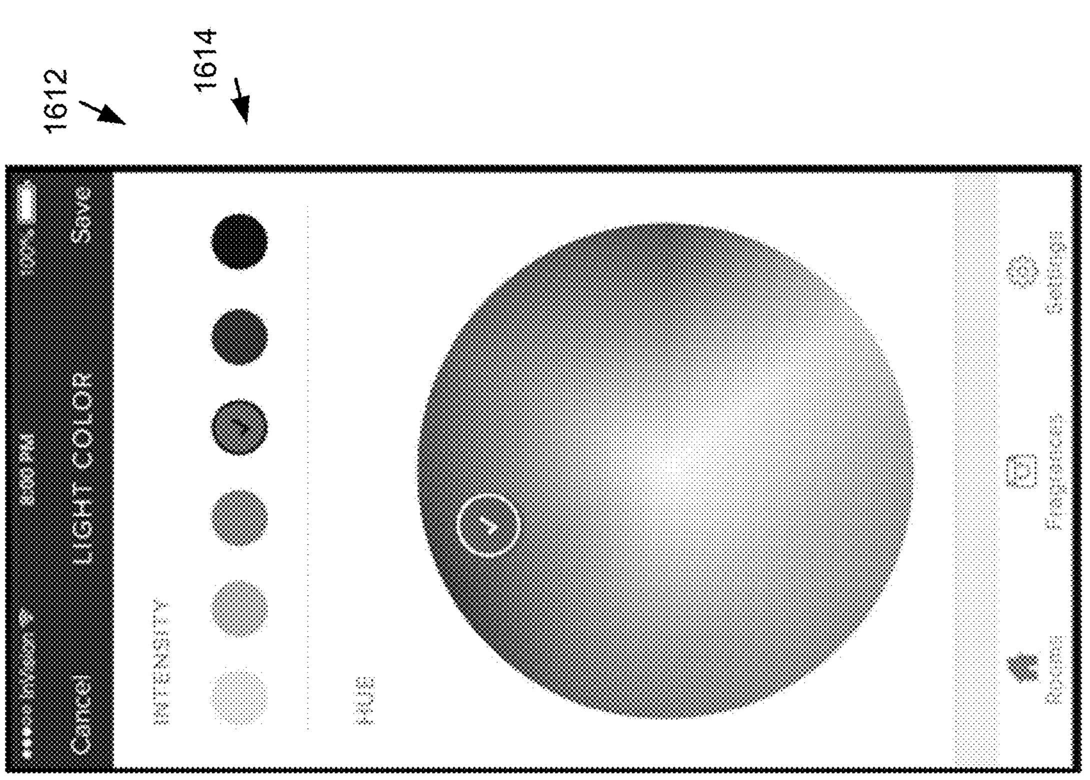

FIG. 16D depicts a user interface 1608 that includes a set of user interface elements 1610 in which the user may customize the color of the light that may be output by the scent dispenser 132 during scent dispensation. In some embodiments, the user interface 1608 may include an automatically selected color that is determined to correspond with the scent scheduled to be dispensed (e.g., relaxing bath). In some embodiments, the user may manually select and/or customize which color should be illuminated, or select from a list of previously selected colors that the scent application 108 stored or retained in memory. FIG. 16E depicts a user interface 1612 for selecting a custom color for the light using user interface elements 1614 (e.g., intensity selector, hue selector, etc.). Upon configuring the schedule and light settings, the scent application 108 may transmit the schedule data reflecting the settings to the dispenser management application 160, which may store the settings in the data store 170 (e.g., as user data, dispenser data, etc.) in association with the user's user ID, the scent dispenser 132 ID, etc.

Figure 17:
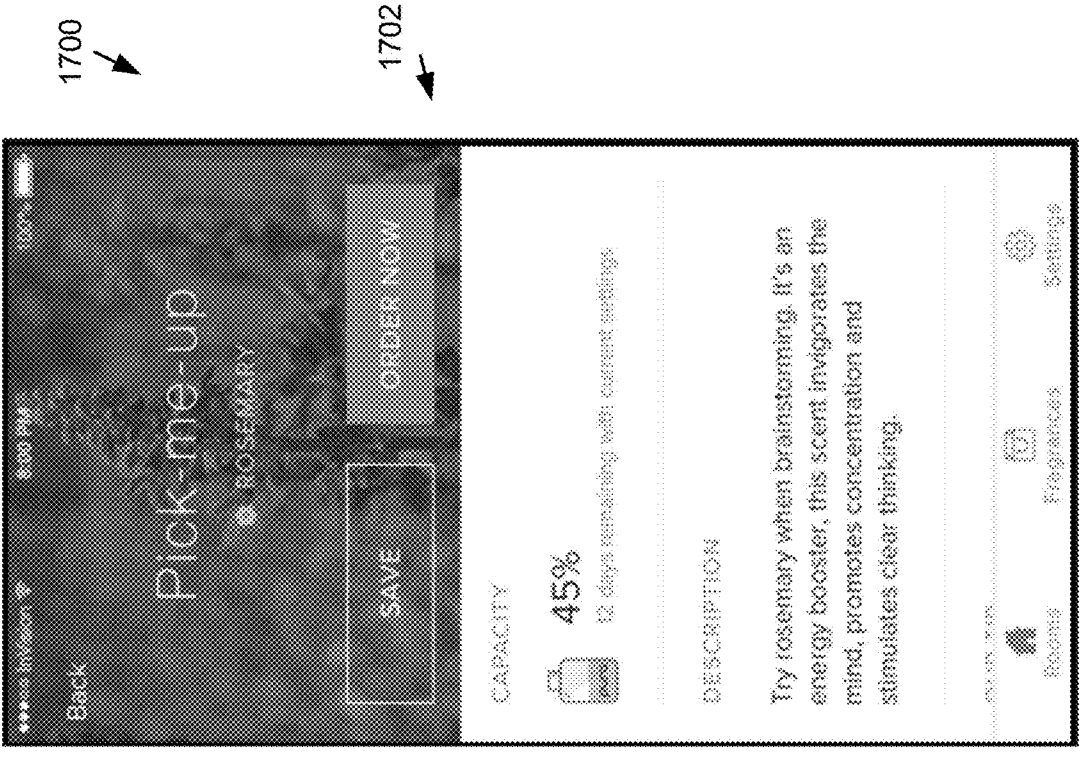
FIG. 17 is a graphical representation of a user interface for viewing vial properties of an installed vial.

FIG. 17 is a graphical representation of a user interface 1700 for viewing vial properties of an installed vial. As shown, the vial depicted in the interface 1700 has a 45% capacity. This fill level may be determined by the vial sensor of the scent dispenser 132 configured to detect fill level of the vial. The controller of the scent dispenser 132 may transmit the fill level data received from the vial sensor to the dispenser management application 160 for processing and/or storage in the data store 170 as usage data 178 in association with the scent dispenser 132 ID, the user ID associated with the scent dispenser 132, etc. The user interface 1700 includes user selectable options 1702 for saving that scent type to the user's account (e.g., as reflected by the user data 174 associated with the user ID of that user) and/or ordering replacement/refill vial 250 from an online marketplace hosted by the dispenser management application 160 and/or another e-commerce server or service coupled to the network 102.

FIGS. 18A-18M are graphical representations of user interfaces of electronic marketplace for (re)ordering vials. FIG. 18A depicts a user interface 1800 including interface elements 1802 selectable for viewing information about scents currently installed in the scent dispenser(s) 132 of the user, viewing all available scent types, and viewing scent types by various categories such as room type.

Figure 18B:
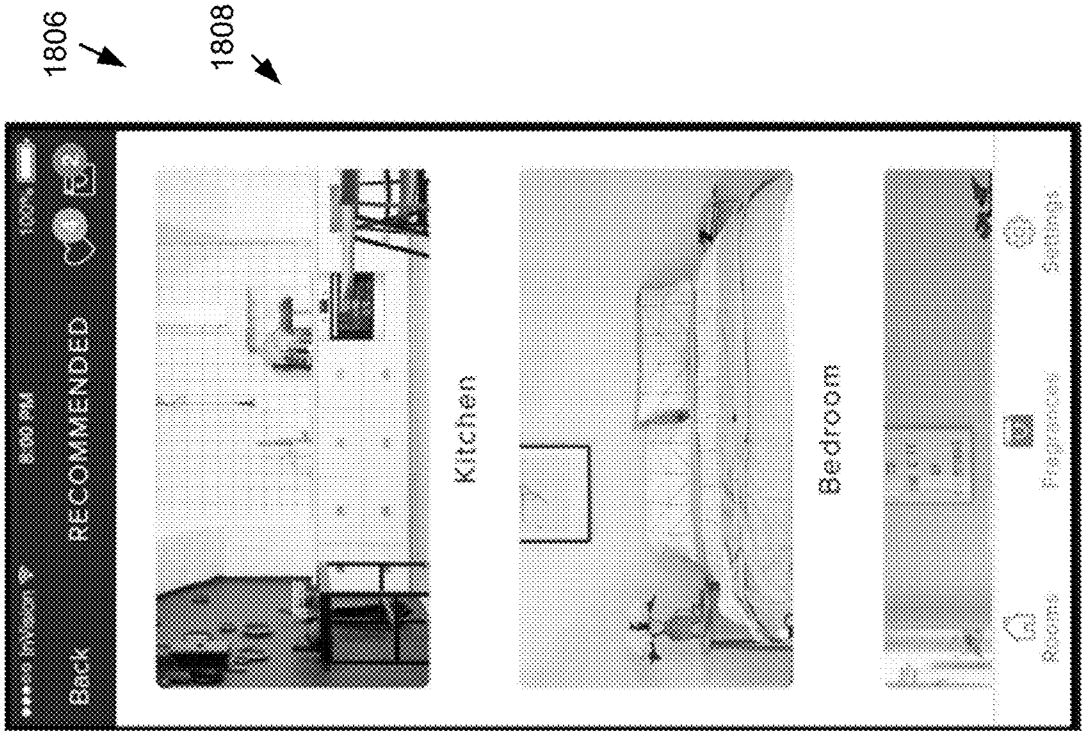
FIGS. 18A-18M are graphical representations of user interfaces of electronic marketplace for (re)ordering vials.
Figure 18A:
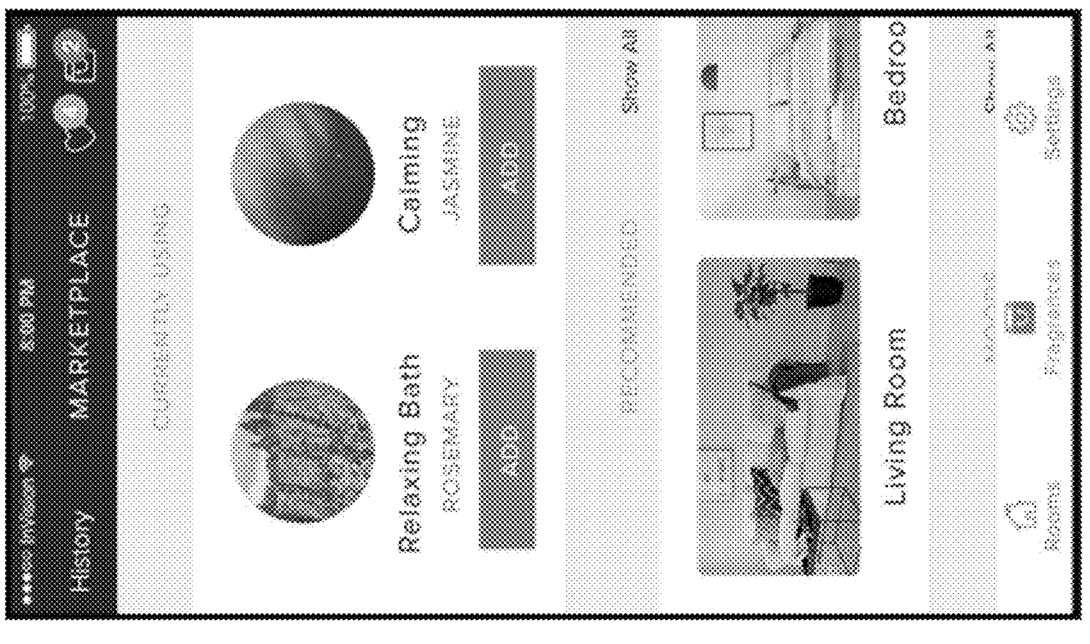

FIG. 18B depicts a user interface 1806 including user interface elements 1808 selectable for viewing scent types by room type. For instance, upon selecting a bedroom room type, the scent application 108 may display the user interface 1810 depicted in FIG. 18C, which includes a list 1812 with which the user may interact to view information about different scent types that are recommended for use in the bedroom.

Figure 18D:
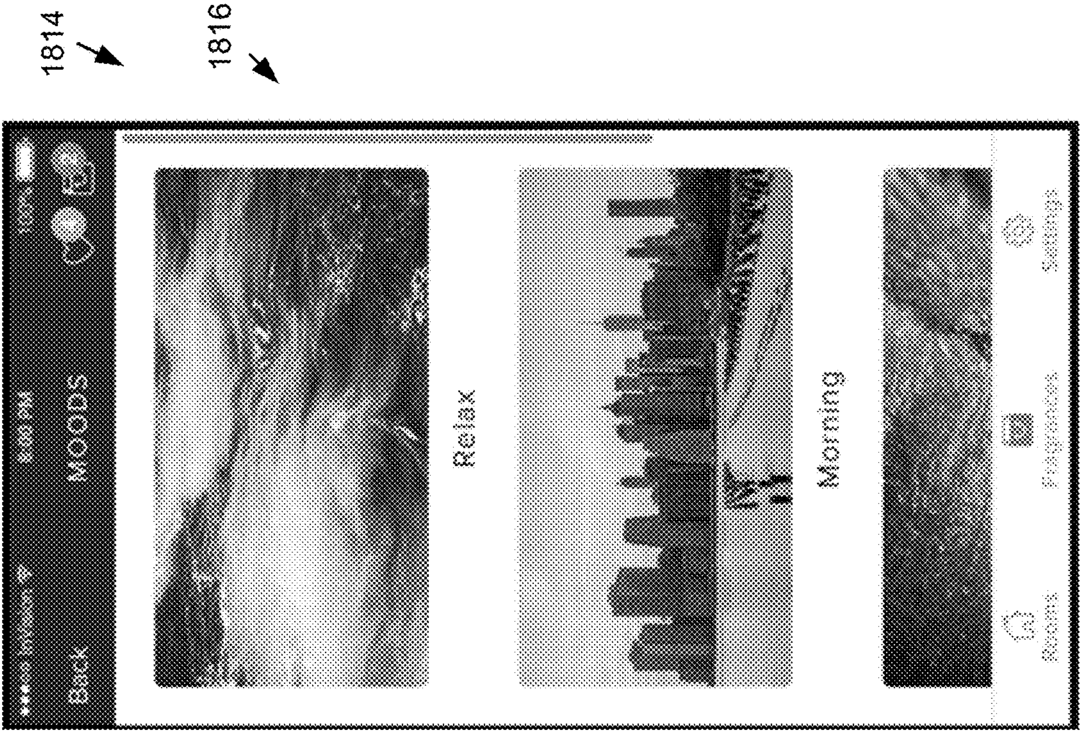
Figure 18C:
Figure 18F:
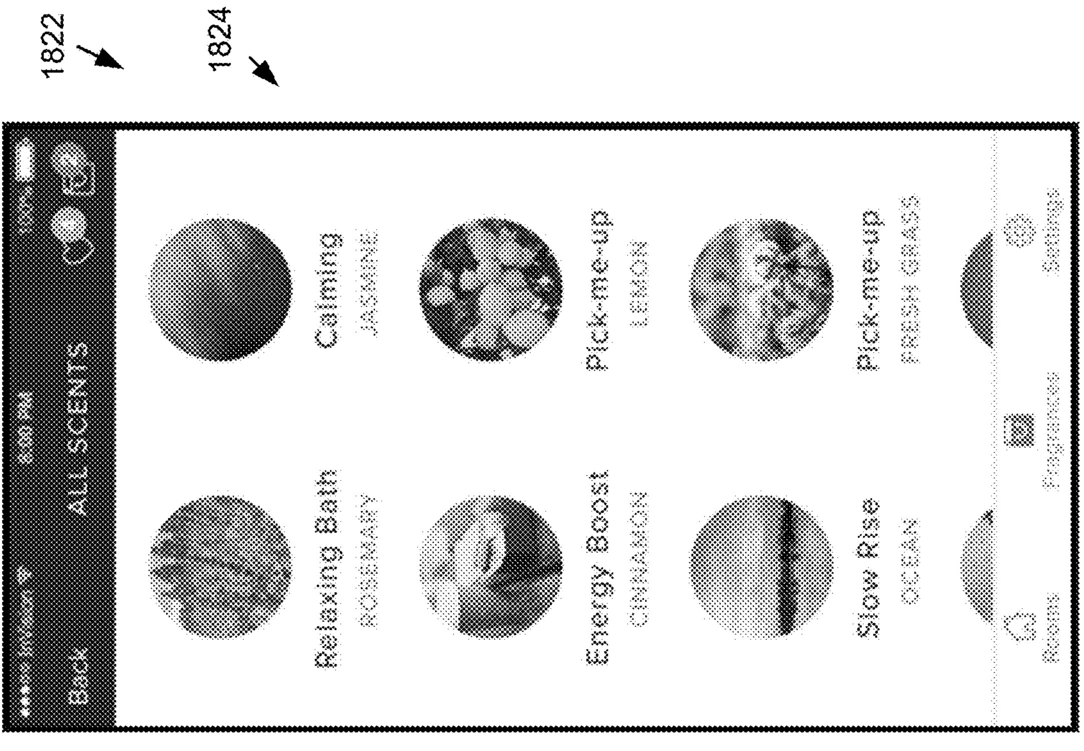
Figure 18E:
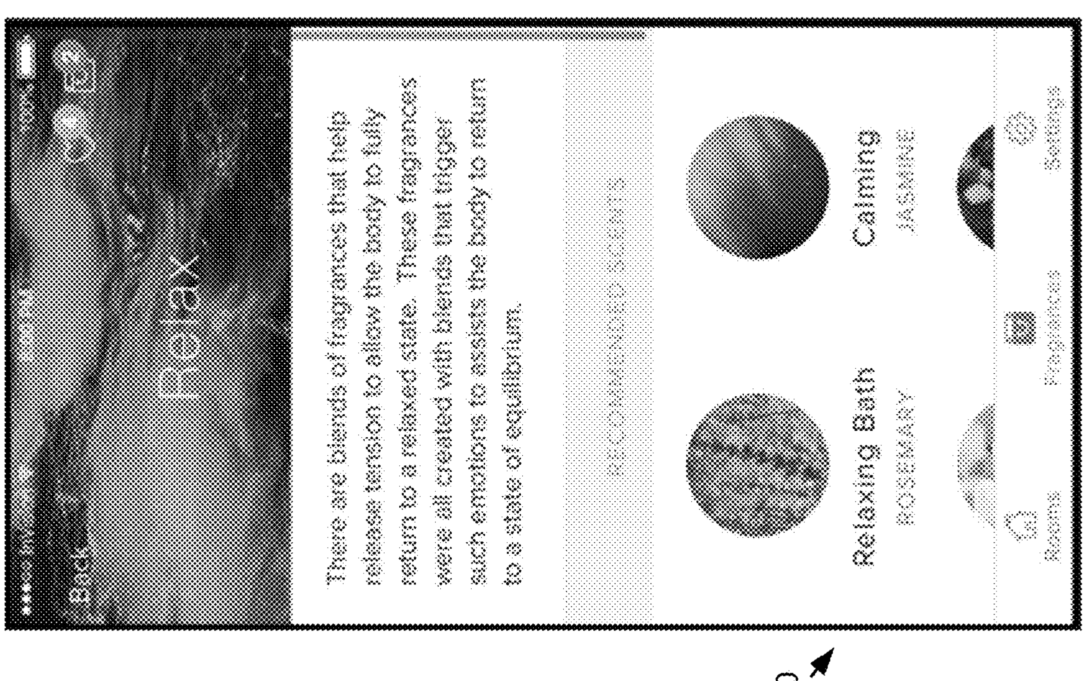

FIG. 18D depicts a user interface 1814 including user selectable interface elements 1816 for viewing scent types by category or theme. For instance, the user may select to view different scents recommended for relaxation, such as those depicted in FIG. 18E, which displays the user interface 1818 including a user-selectable list 1820 of scents. FIG. 18F depicts a user interface 1822 that includes a user selectable list 1824 of all available scent types. The user may select a scent from the various lists depicted in the forgoing figures to view additional information about that scent. An example interface 1826 displaying detailed information about a scent is depicted in FIG. 18G. As shown, the user may review information about the scent and use the user selectable interface elements 1828 to either save the scent to the user's 112 account for later purchase, or to purchase immediately.

In some embodiments, the scent service embodied by the dispenser management application 160 may provide a subscription service to the user in which a certain number of scent vials are automatically shipped to the user (e.g., monthly). The user, using the interfaces depicted in FIGS. 18A-18M, browses and selects the scent vials 250 to add to an upcoming shipment and/or future shipments. When the time comes, a fulfillment center associated with the scent service automatically fulfills the items selected by the user for purchase. For instance, as depicted in FIG. 18G, the interface 1826 includes a user-selectable option for the user to add the scent vial 250 to the next shipment (e.g., add to box.). Upon selection of the interface element, the scent application 108 may transmit order data reflecting the addition of the scent vial 250 to the next shipment, and the dispenser management application 160 may store the order information as user data 174 in association with the user, which may be transmitted to a fulfillment center system to facilitate fulfillment of the order.

Figure 18H:
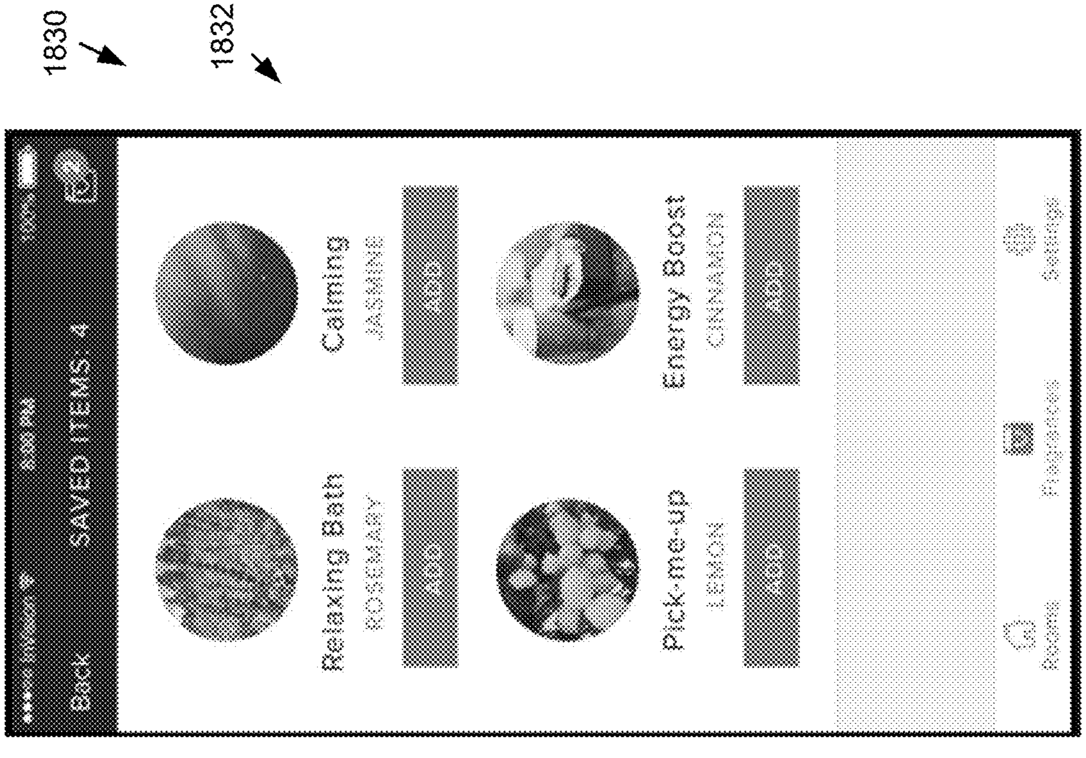
Figure 18G:
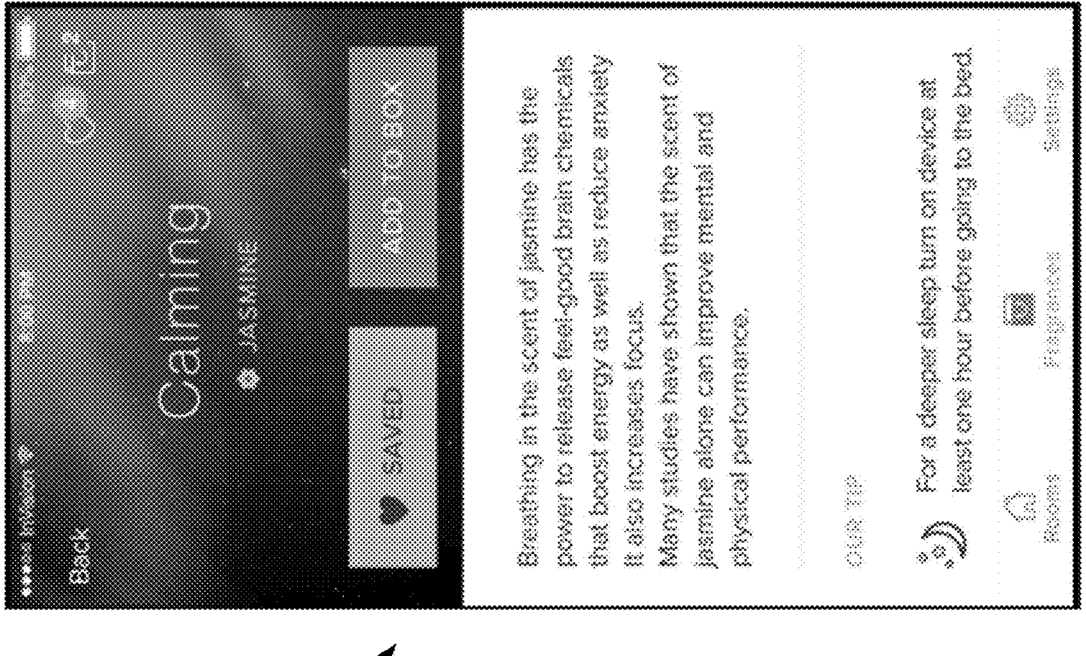

FIG. 18H depicts a user interface 1830 reflecting scent vials that the user has saved to his/her profile for later ordering. Upon selection of one or more of the user selectable interface elements 1832 (e.g., add buttons), corresponding scent vials may be selected for purchase/shipment.

Figure 18J:
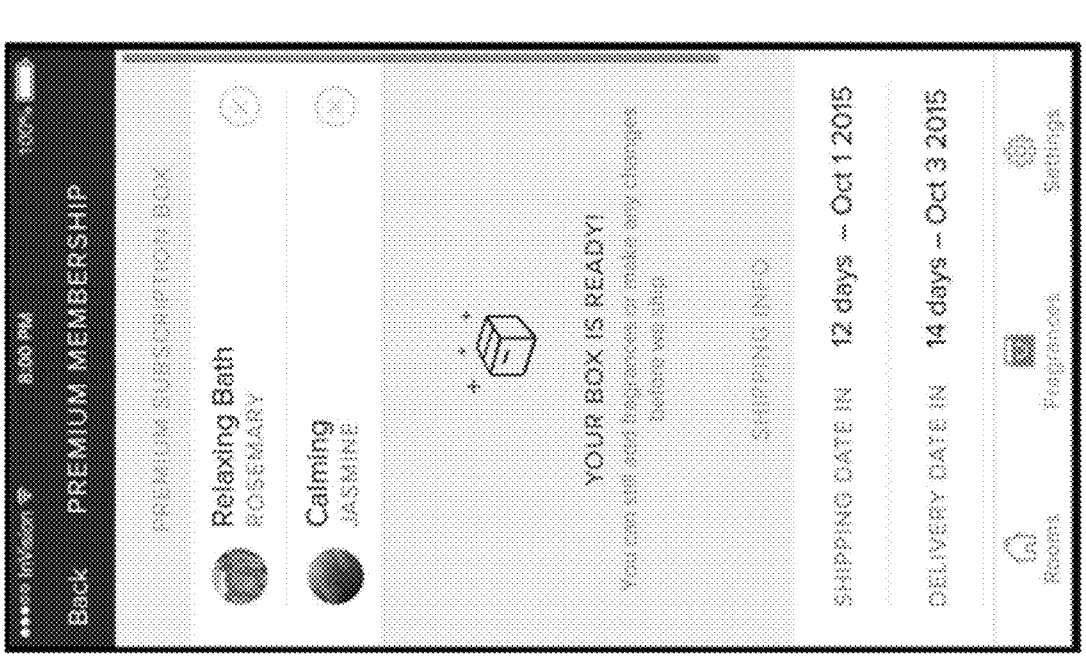
Figure 18I:
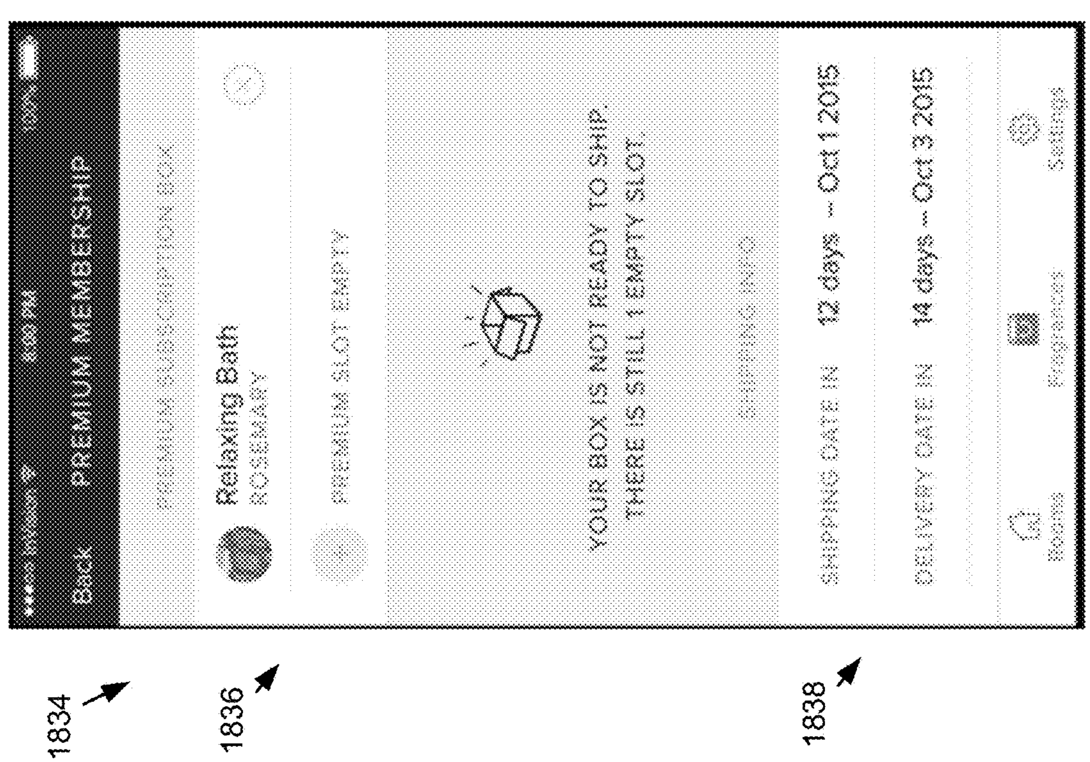

FIGS. 18I and 18J depict a user interface 1834, which includes user interface elements 1836 reflecting the items selected to be included in the user's next shipment, as well as interface elements 1838 including information reflecting when the shipment will occur.

Figure 18L:
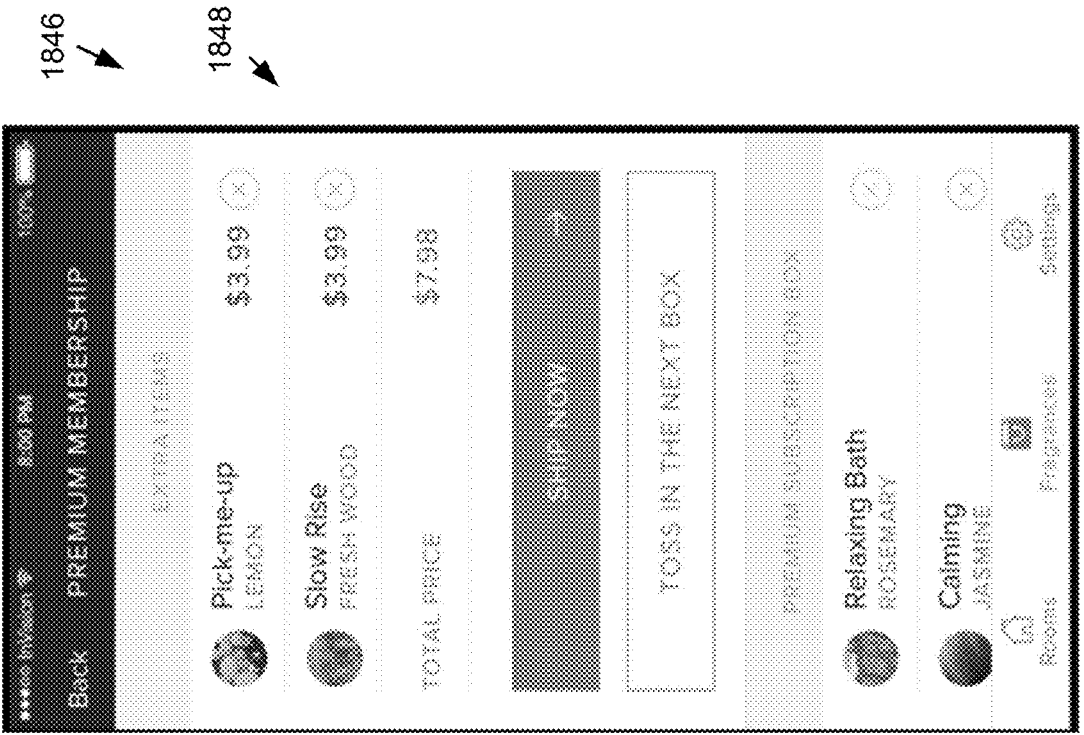
Figure 18K:
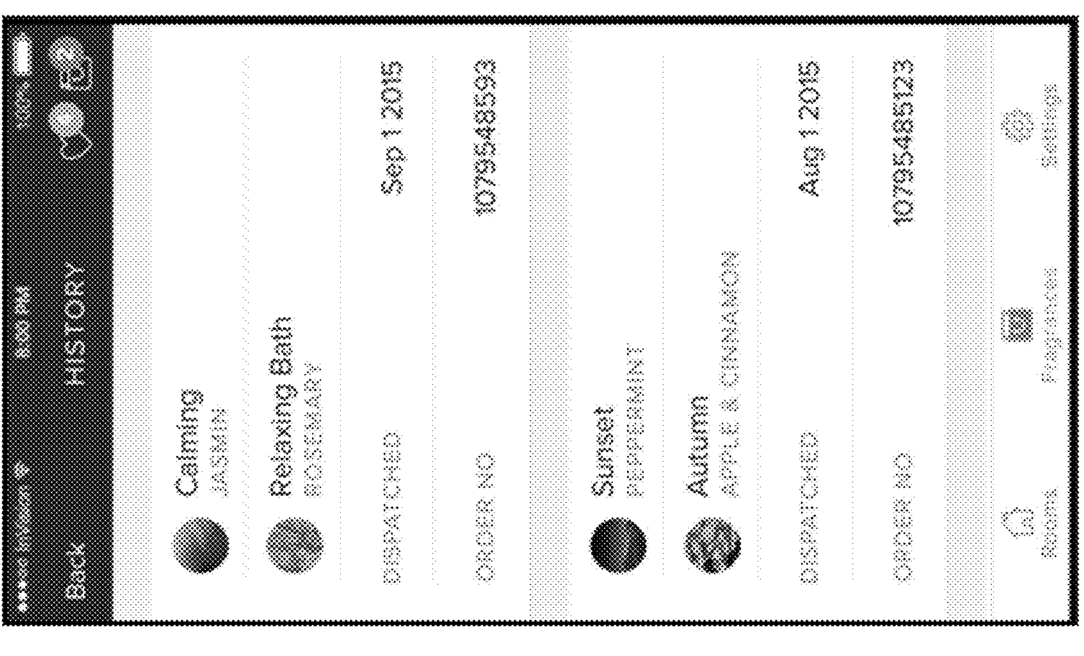
Figure 18M:
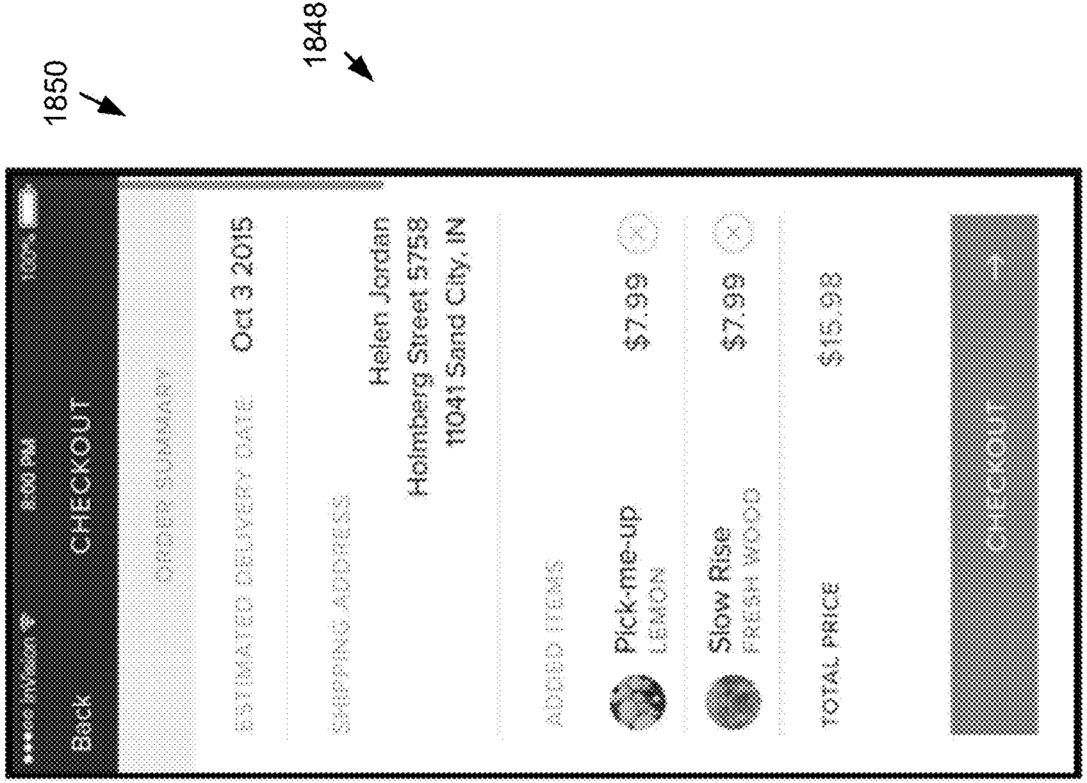

FIG. 18K depicts a user interface 1842 including user interface elements 1844 reflecting the current shipment confirmation and previous shipment confirmations. FIG. 18L depicts a user interface 1846 including user interface elements 1848 providing the user the option to add additional items to a pending shipment, a new shipment, or a subsequent subscription service shipment. FIG. 18M depicts a user interface 1850 including user interface elements 1848 completing a purchase transaction for purchasing scent vials.

Figure 19B:
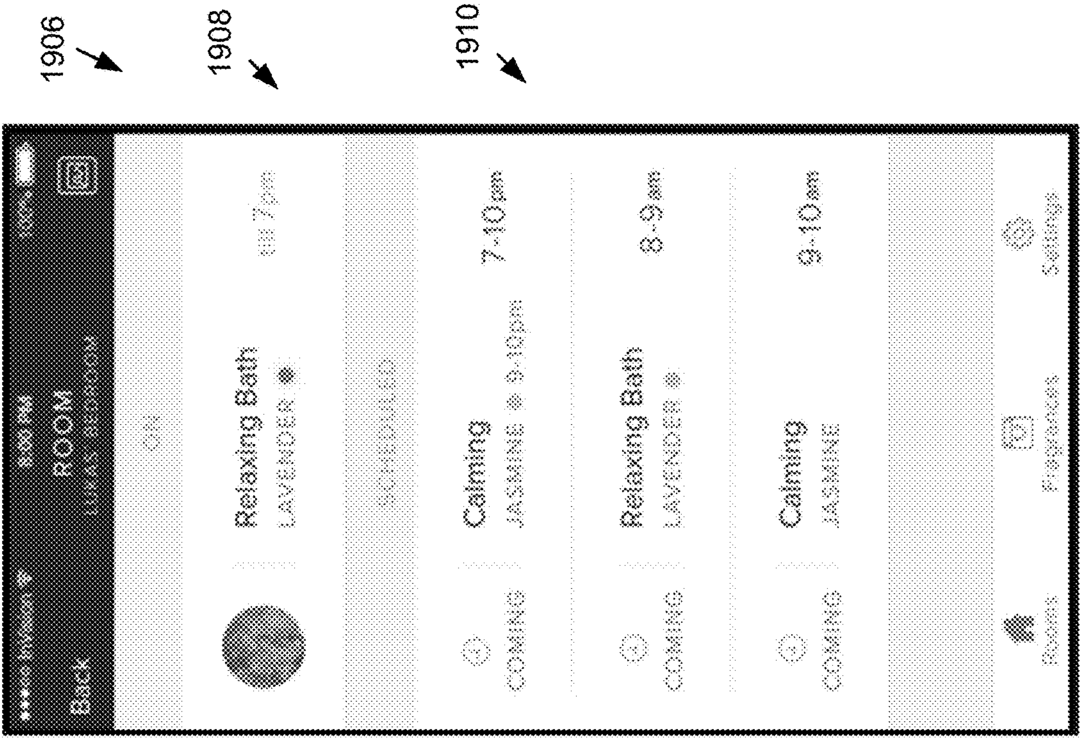
FIGS. 19A-19F are graphical representations of user interfaces for viewing and configuring room, schedule, and dispenser settings.
Figure 19A:
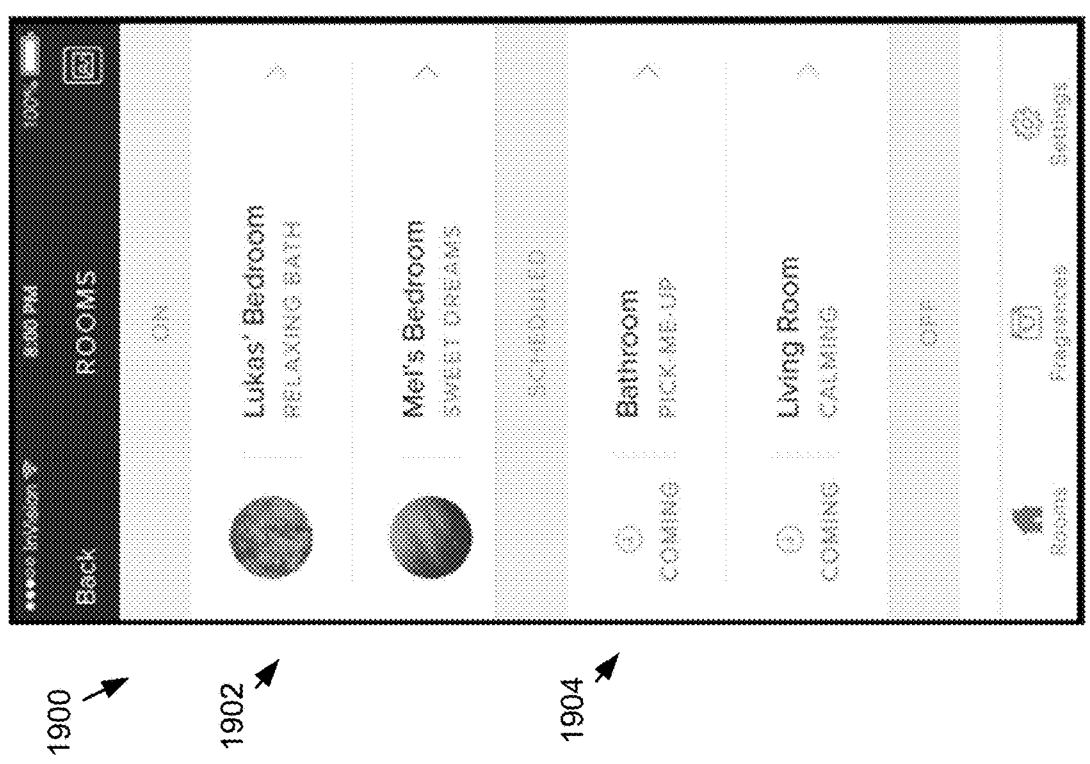

FIGS. 19A-19F are graphical representations of user interfaces for viewing and configuring room, schedule, and dispenser settings. FIG. 19A includes information about which scent dispensers 132 are currently on and which scent dispensers 132 are scheduled to turn on. The information also reflects the scent being dispensed or scheduled to be dispensed by the corresponding scent dispensers 132. The user interface 1900 includes user-selectable interface elements 1902 for modifying the settings of the currently active scent dispensers 132, as well as user-selectable interface elements 1904 for modifying the settings of the currently dormant scent dispensers 132 and the scent dispensers 132 which are turned off. As the state of the scent dispensers 132 change over time, the dispenser management application 160 may send refreshed operational data for the scent dispensers to the scent application 108, and the scent application 108 may refresh interfaces described herein to reflect the current operational state and/or configurations of the scent dispensers 132. Information about each of the scent dispensers 132 registered to the user, including which scents are installed in the scent dispensers 132 and the rooms that the scent dispensers 32 are installed in, can be retrieved by the scent application 108 from the dispenser management application 160. Correspondingly, the dispenser management application 160 may retrieve this information from the data store 170, as described elsewhere herein.

FIG. 19B depicts a user interface 1906 for viewing the details of a particular room (e.g., Lukas' bedroom). The scent application 108 may display the interface 1906 responsive to the selection of a room/scent dispenser 132 in the interface 1900 depicted in FIG. 19A. The user interface 1906 may include the current 1908 and upcoming schedules 1910 for the scent dispenser(s) 132 installed in Lukas' bedroom. For example, currently a scent dispenser 132 in Luka's bedroom is actively dispensing relaxing bath (until 7 PM), and is scheduled to dispense a calming scent (between 7 PM and 10 PM). A user may select any of the listed schedules, and modify that schedule and/or turn off the scent dispenser 132 using a corresponding interface, as discussed elsewhere herein.

Figure 19D:
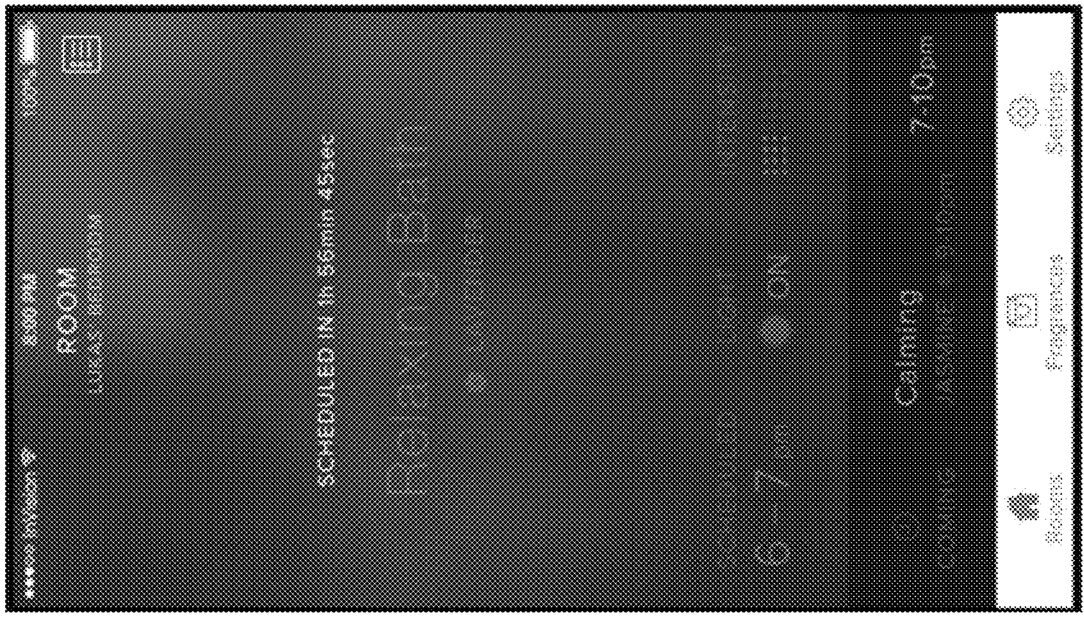
Figure 19C:
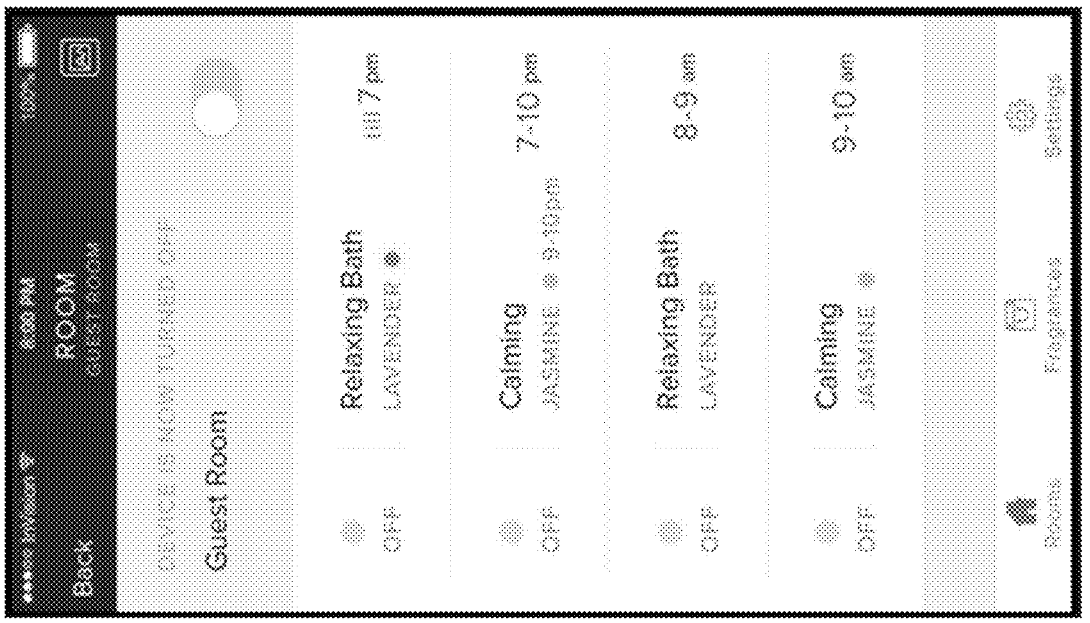

FIG. 19C depicts a user interface 1912 including a user selectable interface toggle 1914 for toggling the scent dispenser 132 in a particular room (e.g., guestroom) on and off. In this case, turning the scent dispenser 132 off/inactive overrides the schedules defined for that scent dispenser 132. Using the user selectable interface elements 1916, the user may select any of the scheduled times for modification, and responsive thereto, the scent application 108 may display a schedule editing interface, as discussed elsewhere herein.

FIG. 19D depicts a user interface 1918 including user-selectable interface elements 1920 for editing different aspects of the scent schedule, such as the time the scent dispensation is scheduled to occur, whether or not to illuminate a light, and the intensity of the scent dispensation, as discussed elsewhere herein.

Figure 19F:
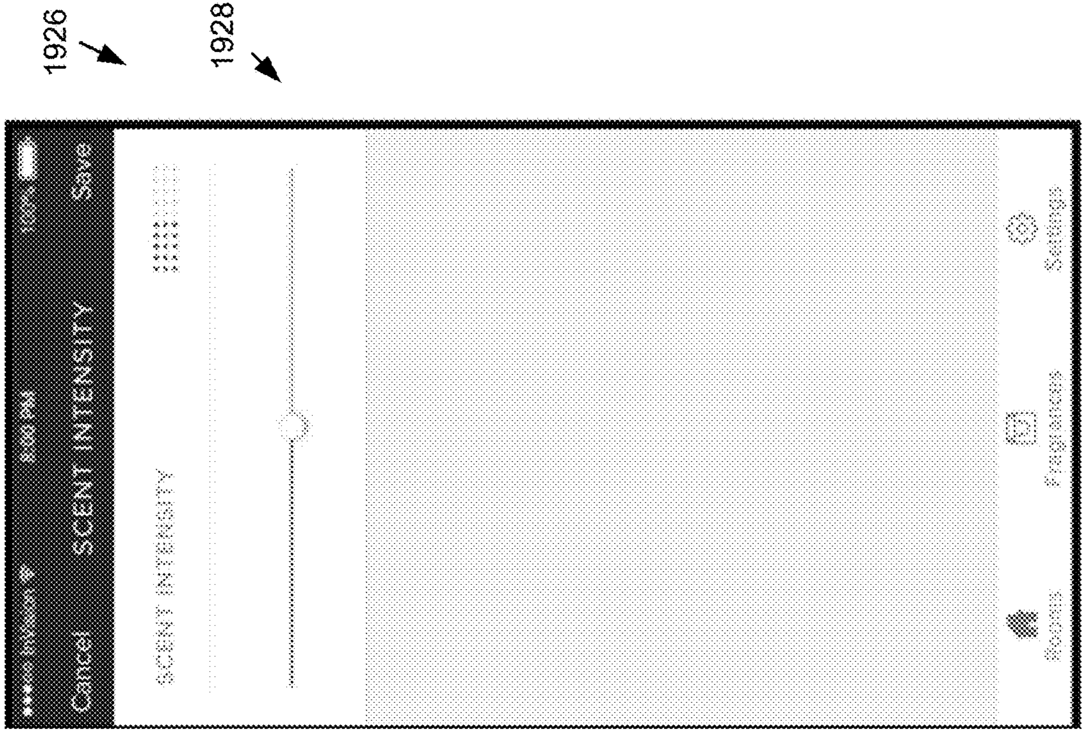
Figure 19E:
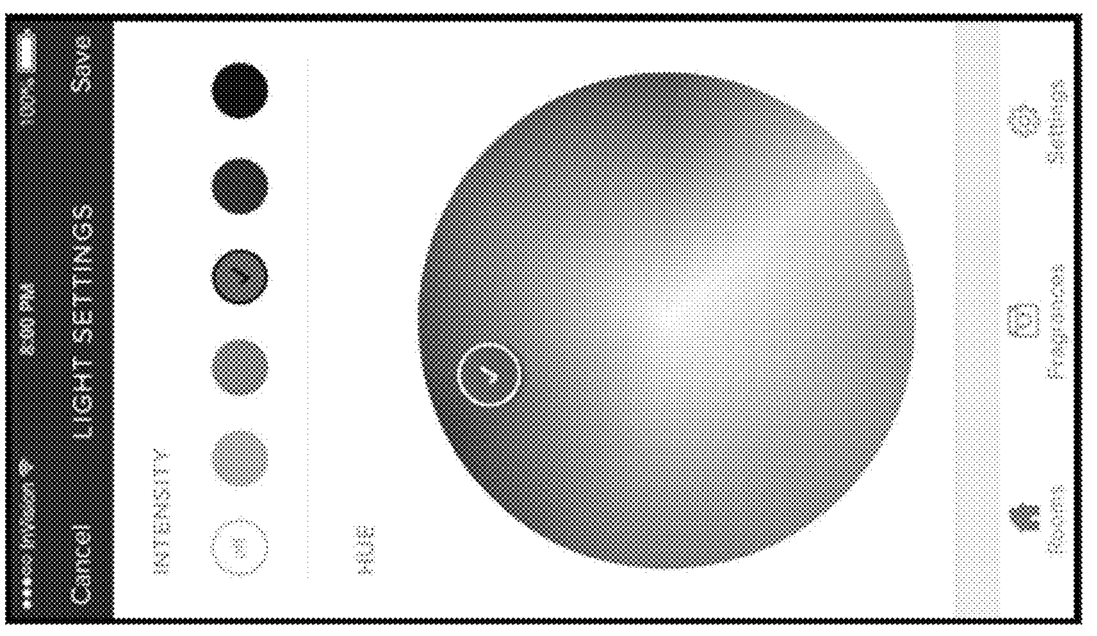

The user interface 1922 in FIG. 19E, which may be displayed responsive to the selection by the user to edit the light settings in the user interface 1918, provides the user options 1924 for configuring the intensity and hue of the light to be illuminated during the scheduled time.

FIG. 19F depicts a user interface 1926 including a user configurable interface element 1928 for adjusting scent dispensation intensity during the scheduled time. For example, the user may use the slider to adjust the intensity up and down. The intensity setting, as with any other of the settings described with reference to the interfaces, may be transmitted to the dispenser management application 160 and stored in the data store 170 and/or transmitted to the scent dispenser 132 as operational settings.

Figure 20B:
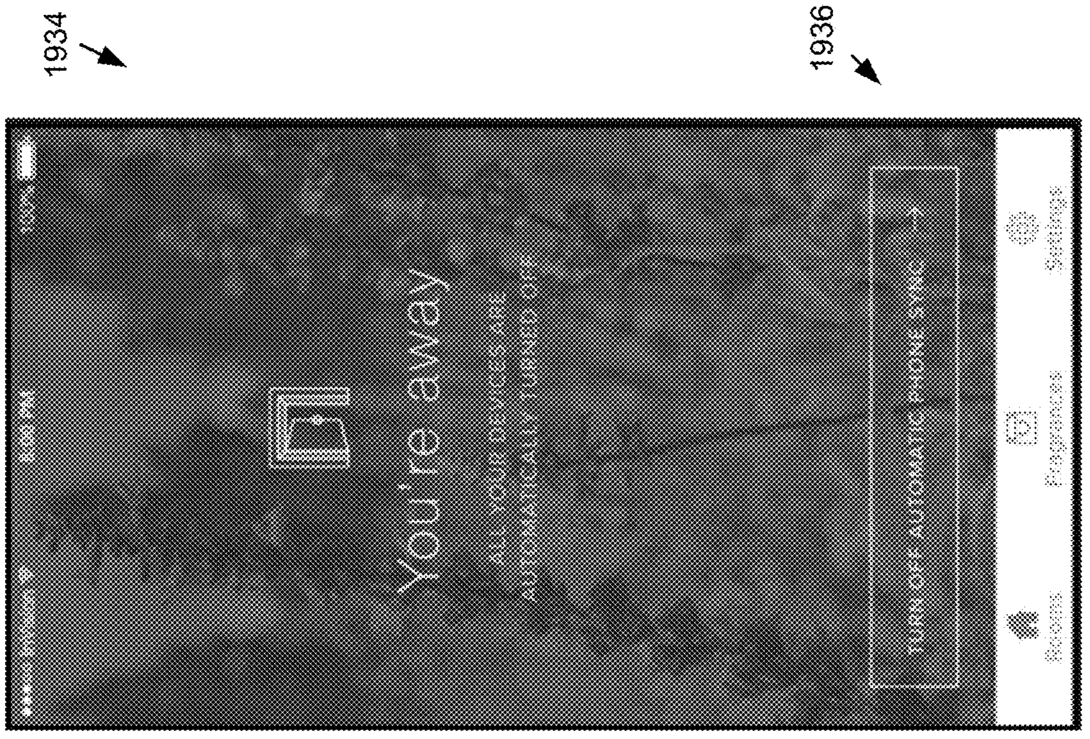
FIG. 20B is a graphical representation of a user interface for disabling geolocation-based control of scent dispensation.
Figure 20A:
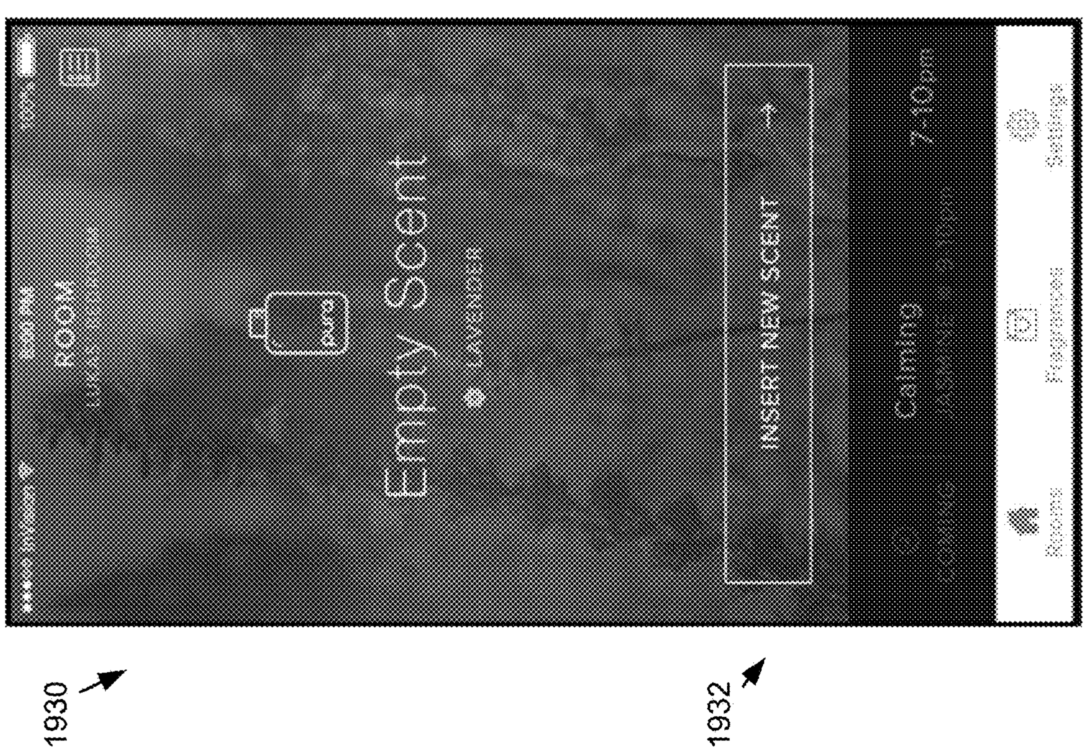
FIG. 20A is a graphical representation of a user interface for installing a new or replacement vial.

FIG. 20A is a graphical representation of a user interface 1930 including a notification prompting the user to install a new or replacement vial. The notification may include a user selectable interface element 1932 for installing a new scent vial. Responsive to the selection of the element 1932, the scent application 108 may provide the user with instructions on how to swap out the old/empty vial with a new vial 250 and/or provide the user with options to purchase additional scent vials 250.

FIG. 20B is a graphical representation of a user interface 1934 for disabling geolocation-based control of scent dispensation. In some embodiments, responsive to the user, and the user's mobile device 106, leaving the premises that is registered to the user (e.g., as reflected by geofence settings stored as user data 174 in the data store 170 and/or the memory of the mobile device 106), the scent application 108 may display the user interface 1934 notifying the user that all of the scent dispensers 132 on the premises were automatically turned off/made inactive because the user was not present at the premises. The user interface 1934 further provides the user selectable interface element 1936 for disabling the automatic turning off of the scent dispensers 132 upon leaving the premises. Upon selecting the user interface element 1936, the scent application 108 transmits updated setting to the dispenser management application 160 instructing the sensor management application 160 to update the user's account to reflect not inactivating the scent dispensers 132 when the user leaves the premises.

Returning to FIG. 1, the dispenser management server 150 may include one or more computing devices having data processing, storing, and communication capabilities. For example, the server 150 may include one or more hardware servers, virtual servers, server arrays, storage devices and/or systems, etc., and/or may be centralized or distributed/cloud-based. In some embodiments, the server 150 may include one or more virtual servers, which operate in a host server environment and access the physical hardware of the host server including, for example, a processor, memory, storage, network interfaces, etc., via an abstraction layer (e.g., a virtual machine manager).

While not depicted, the server 150 may include a (physical, virtual, etc.) processor, a non-transitory memory, a network interface, and a data store 170, which may be communicatively coupled by a communications bus. Similarly, the client device 106 may include a physical processor, a non-transitory memory, a network interface, a display, an input device, a sensor, and a capture device. It should be understood that the server and the client device may take other forms and include additional or fewer components without departing from the scope of the present disclosure.

Software operating on the server 150 (e.g., the dispenser management application 160, an operating system, device drivers, etc.) may cooperate and communicate via a software communication mechanism implemented in association with a server bus. The software communication mechanism can include and/or facilitate, for example, inter-process communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

As shown, the server 150 may include a dispenser management application 160 embodying a remotely accessible scent service. The dispenser management application 160 may send data to and receive data from the other entities of the system including the controllers 188 and/or 328, the mobile device(s) 106, etc. The dispenser management application 160 may be configured to store and retrieve data from one or more information sources, such as the data store 170. In addition, while a single server 150 is depicted in FIG. 1, it should be understood that one or more servers 150 may be included.

In some embodiments, the dispenser firmware 194, the scent application 108, the dispenser management application 160, etc., may require users to be registered to access the acts and/or functionality provided by them. For example, to access various acts and/or functionality provided by the scent application 108, dispenser management application 160, and/or scent dispensers 132, these components may require a user to authenticate his/her identity (e.g., by confirming a valid electronic address). In some instances, these entities 108, 132, 150, etc., may interact with a federated identity server (not shown) to register/authenticate users. Once registered, these entities 108, 132, 150, etc., may require a user seeking access to authenticate by inputting credentials in an associated user interface.

FIGS. 2A-2G are various views of an example scent dispenser 132. As shown, the scent dispenser 132 includes a housing 200 that houses the components of the scent dispenser (e.g., vial coupling(s), heating element(s), vial sensor, etc.).

The housing 200 includes a body 202 and a detachable lid 204. The backside 212 of the housing includes a plug 206 that can be plugged into a conventional outlet (e.g., 146) to power the device. The scent dispenser 132 also includes one or more electronic interfaces, such as USB port 208, which the user can utilize to charge other devices, plug the scent dispenser into a computer to update firmware, set settings, etc. The housing 200 may also include one or more output devices 210, such as LED(s), which are discussed further below.

Figures 2A, 2B:
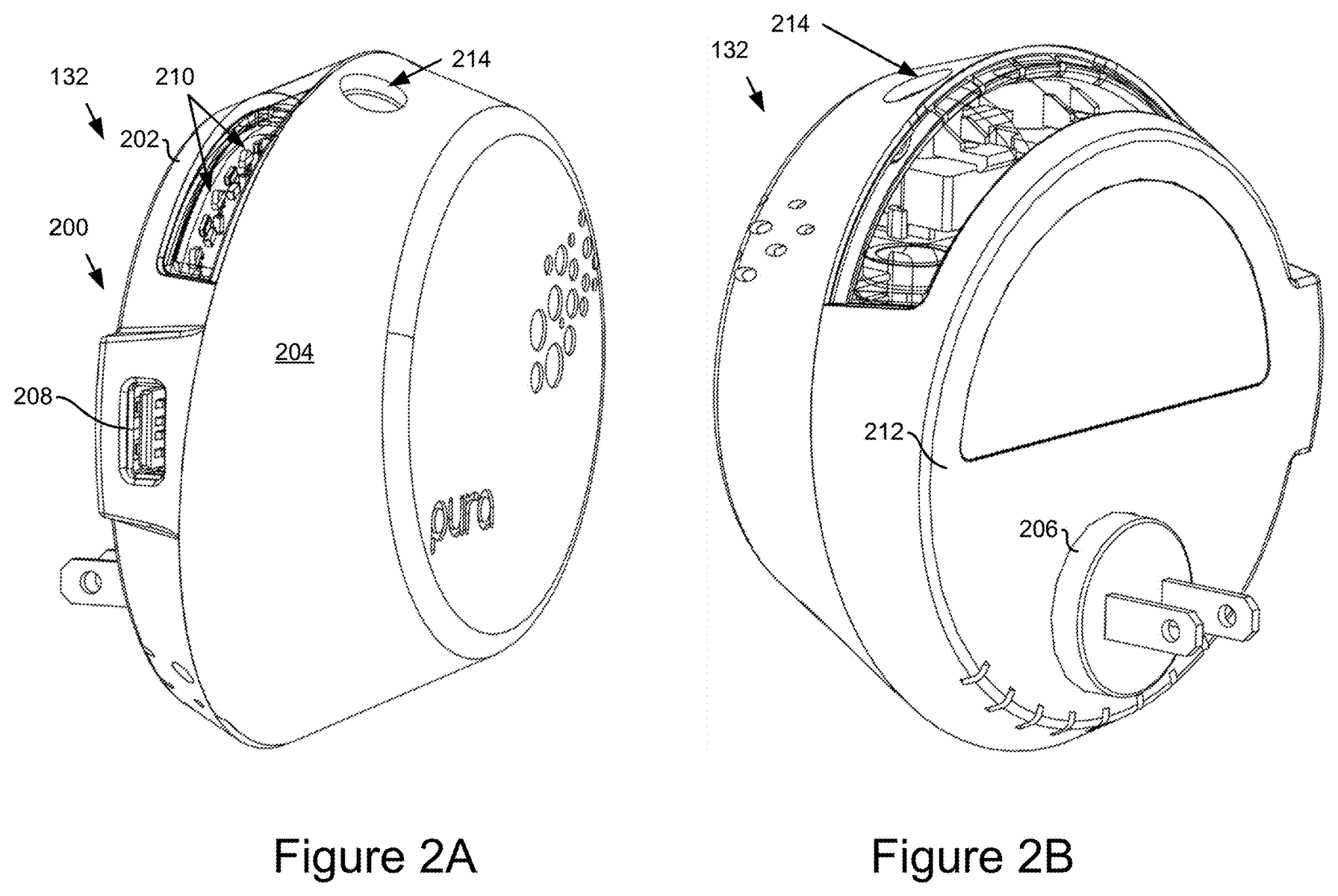
Figure 2C:
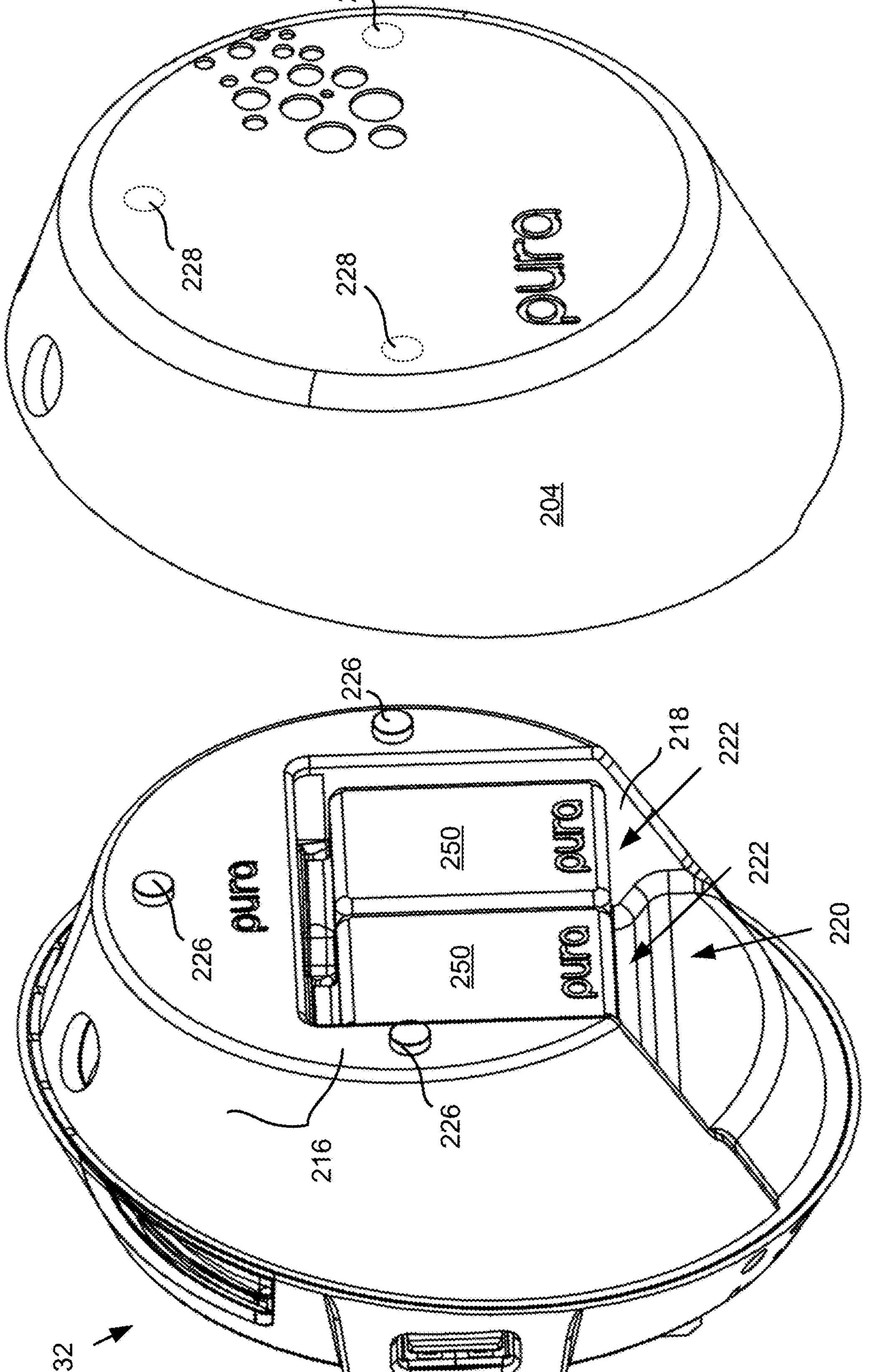
FIG. 2C is a front view of the example scent dispenser with a cover removed.

As shown in FIG. 2C, the lid 204 of the dispenser 132 is removable to provide access to one or more scent vials 250 (e.g. in this case two, although conceivably any number of scent vials can be included), which can be inserted into a cavity 220 exposed by the lid when removed. In particular, when the lid 204 is removed, it exposes an inner surface 216 including a concave surface 218 that forms the cavity 220. The lid/removable cover 204 can be (re)attached to the front side/inner surface 216 of the housing 200 to cover the opening/cavity 220 providing access to the vial(s) 250.

The cavity 220 includes two slots 222 (left and right from a front view) in the depicted embodiment, although it should be understood that any number of slots maybe included to accommodate any number of scent vials 250. Each slot 222 accommodates a corresponding vial 250, which contains particular scent solution (not depicted).

The front side/inner surface 216, which is exposed when the lid 204 is removed, includes a (e.g., second) set of magnetic fasteners 226 that are configured to magnetically detachably attached to a corresponding (e.g., first) set of magnetic fasteners 228 included in the removeable cover/lid 204. For instance, the lid 204 may include a set of magnetic fasteners 228 on an inside surface (not shown) of the lid that abuts the inner surface 216 that engage with the set of magnetic fasteners of the body when the lid is situated abuttingly with the front side/inner surface 216 of the housing 200 of the scent dispenser 132.

Figures 5A, 5B:
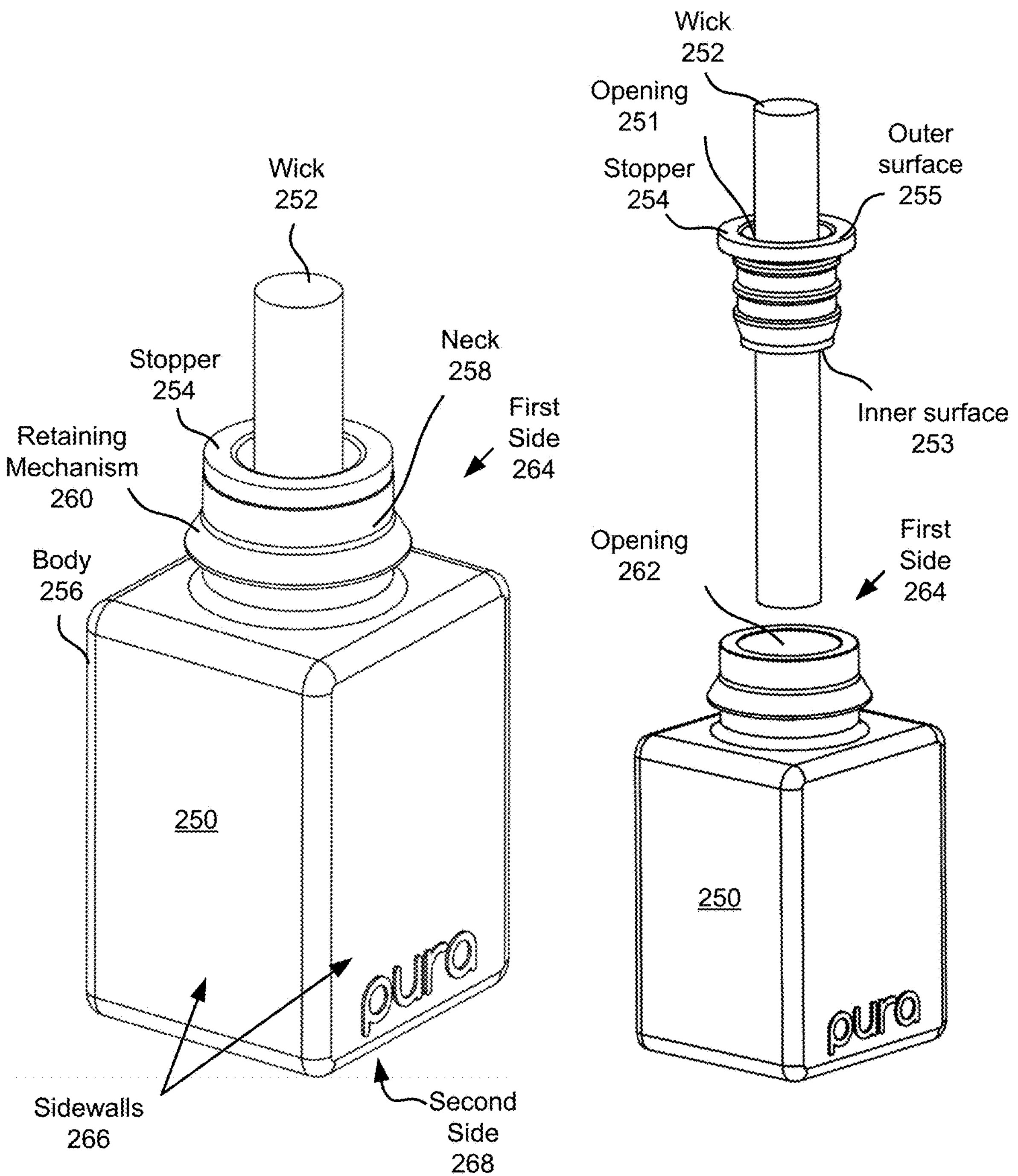
FIG. 5A is a front perspective view of an example vial with a wick inserted.
FIG. 5B is a front perspective view of the example vial with the wick removed.

FIGS. 5A and 5B are various views of an example vial 250, although it should be understood that the vial 250 may take other forms and have different dimensions. The solution may include chemical(s) that are processed by the scent diffuser 132 to diffuse or nebulize it within the room in which the scent dispenser 132 is placed. The solution in some embodiments may be a liquid perfume, an essential oil, or other suitable solutions. In some alternative, the perfume or essential oil may be caked and the caked substrate may be heated to diffuse the scent. A vial 250 may be made of any suitable material, such as plastic, metal, ceramic material, glass, etc.

In some embodiments, a vial 250 (e.g., a first vial, second vial, etc.) may include a first side 264, one or more sidewalls 266, and a second side 288. For example, a vial 250 having a tubular sidewall may be a continuous around a circumference. In another example, a vial 250 having a square, triangular, rectangular, etc., cross-section (e.g., halfway between the second side 268 and the first side 264) at a middle of the sidewall, may have a plurality of sidewalls that are joined along at the corners of the cross-section. It should be understood that the vial 250 may have any shape. The one or more sidewalls 266 connecting the first side 264 to the second side 268. The first side 264, the one or more sidewalls 266, and the second side 268 collectively form an inner cavity (e.g., see FIGS. 4A-4D). The first side 264 includes an opening 262 through which a solution containable in the inner cavity can be dispensed from the vial 250.

In some embodiments, the first side 264 includes a neck 258 forming the opening 262, and the sidewall(s) 266 and second side 268 form a hollow body 256. The hollow body forms a cavity containing the scented solution. A wick 252 may extend from the cavity through the opening 262 of the neck 258.

As shown in FIGS. 5A and 5B, in some embodiments, the vial 250 may include a stopper 254 and a wick 252. The stopper 254 inserts into an opening 262 of the vial 250 and forms a seal against an inner surface of the neck 258. The stopper 254 includes a through-hole 251 extending through a center portion of the stopper 254 from an outer surface 255 of the stopper to an inner surface 254 of the stopper 254. The through-hole/opening 251 is formed in the stopper to allow a wick inserted into the cavity of the vial 250 to extend outwardly from the through-hole 251, and thus the opening 262 of the first side 264.

Figure 2D:
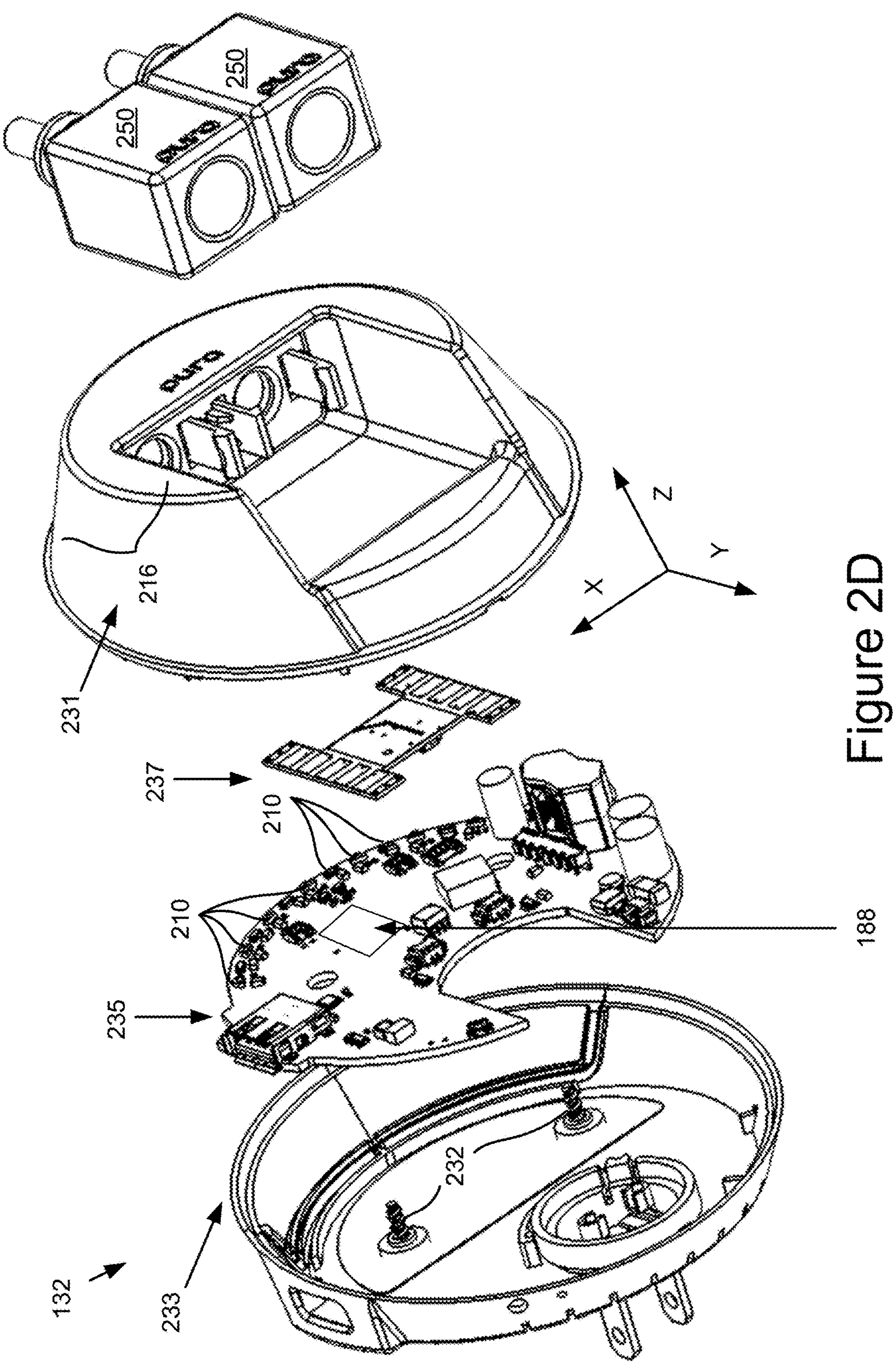
FIG. 2D is a front exploded view of the example scent dispenser.
Figure 21:
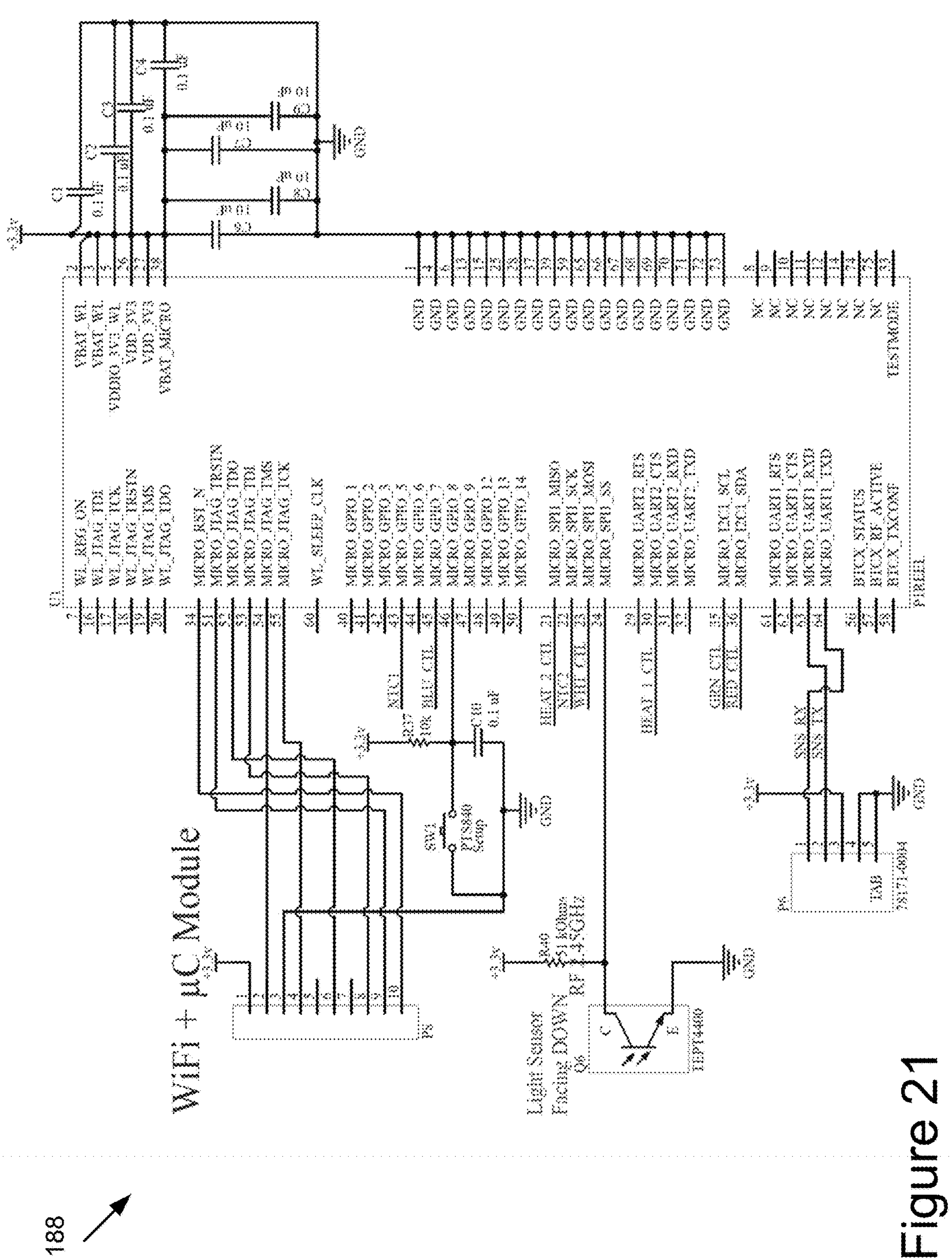
FIGS. 21-25 are schematic diagrams of various example components of a scent dispenser.
Figure 22:
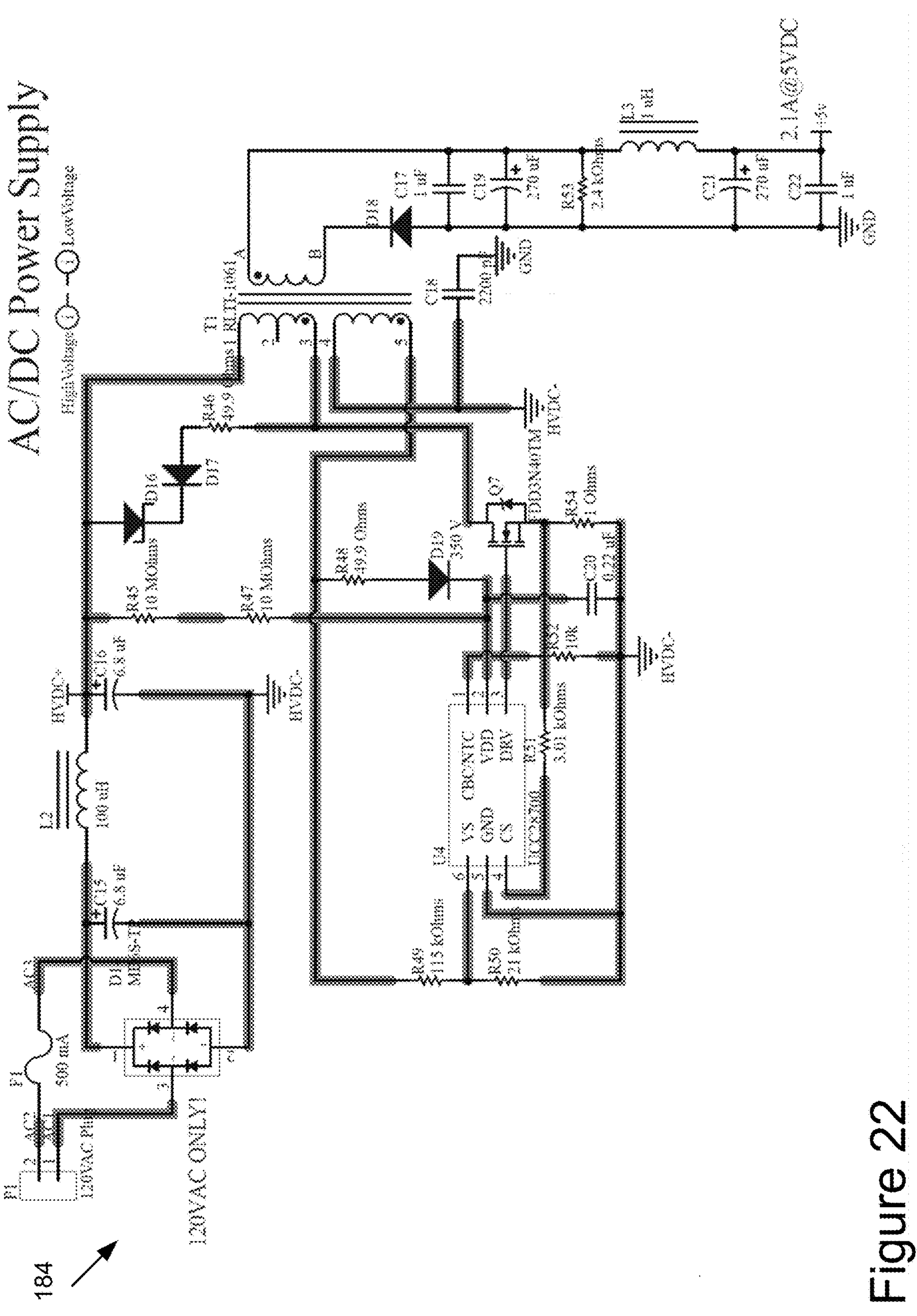
Figure 23:
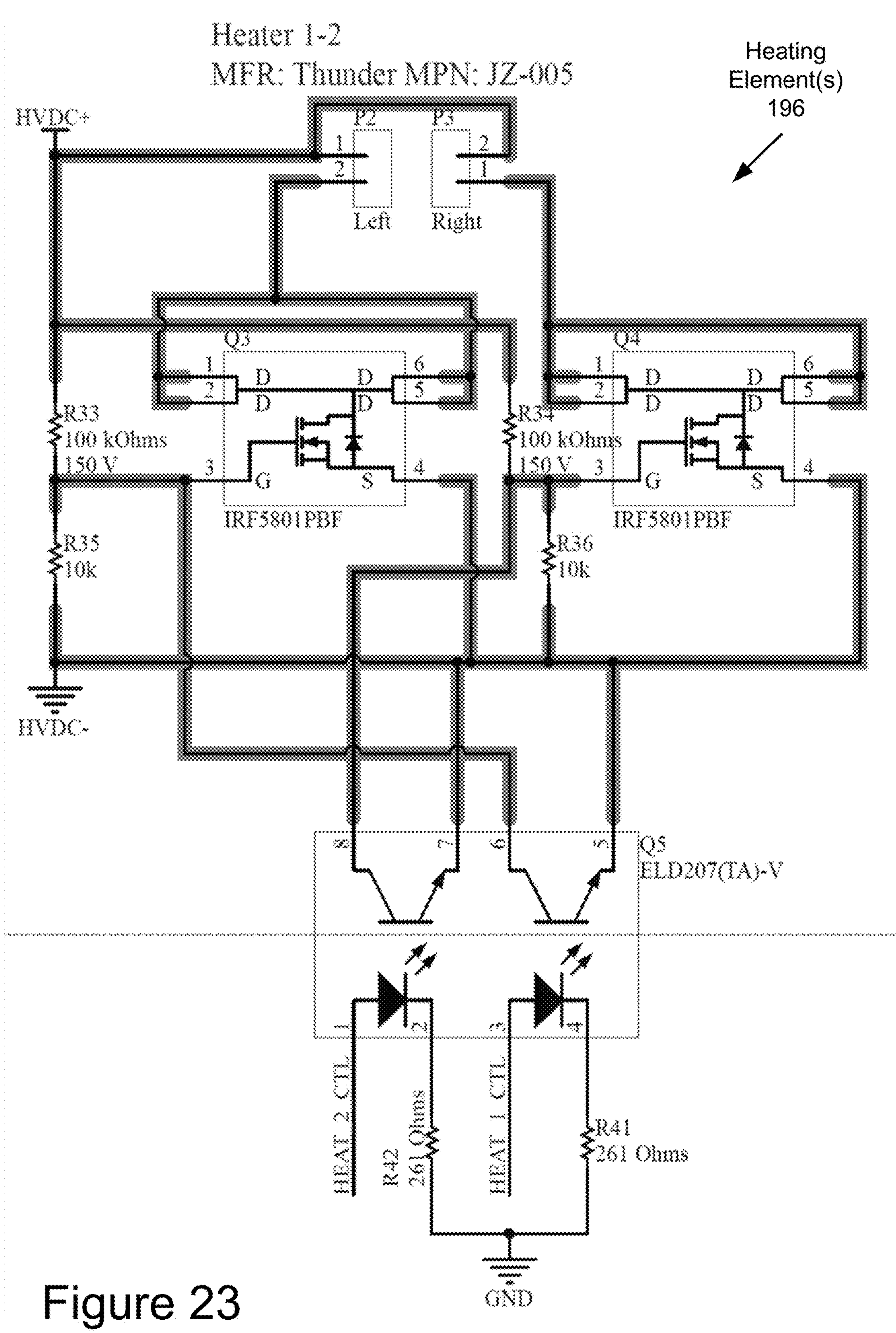
Figure 24:
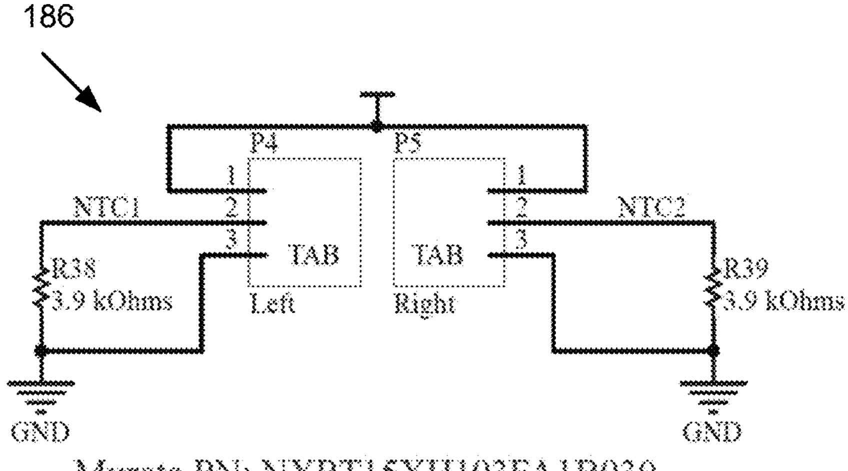
Figure 25:
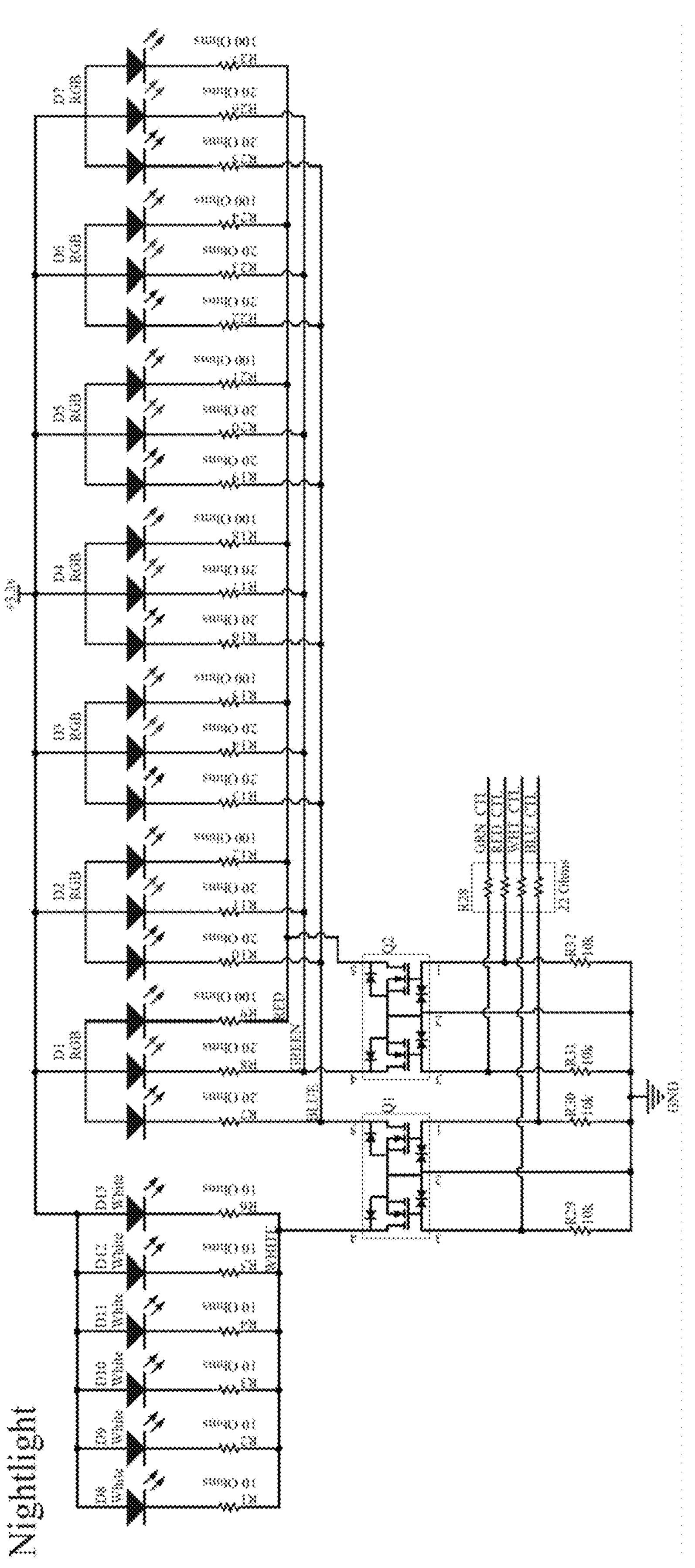

FIG. 2D is an exploded view of the scent dispenser 132 housing 220 with the lid 204 removed. As shown, the scent dispenser 132 includes a back housing portion 233 and a front housing portion 231 that are attachable using one or more fasteners 232 (e.g., screws, snaps, etc.). The back housing portion 233 and the front housing portion 231 collectively enclose and retain the electronics of the scent dispenser 132. In the depicted example, the dispenser's 132 electronics may a controller 188 that controls the components of the scent dispenser 132. In some embodiments, the scent dispenser 132 includes multiple circuit boards (e.g., a sensor board 237, a main board 235), although it should be understood that the boards could be combined or further split up, etc. In the depicted embodiment, the main board 235 includes the controller 188. FIGS. 21-25 are schematic diagrams of various example electronics of the scent dispenser 132 illustrating wiring and features of the electronics that would be readily interpretable and understandable by one having skill in the art. In particular, FIG. 21 is a schematic diagram of an example controller 188, which includes a wireless communications chip (e.g., the interface 190); FIG. 22 is a schematic diagram of an example PS 184; FIG. 23 is a schematic diagram of an example heating element circuit including the heating element(s) 196; FIG. 24 is a schematic diagram of an example sensor 186, such as a temperature sensor configured to sense the temperature of a heating element 196 and provide the temperature to the controller 188 for temperature feedback control; FIG. 25 is a schematic diagram of an example output device 192, such as an array of LEDs controllable by the controller 188 based on light settings set using the scent application 108.

Figure 2E:
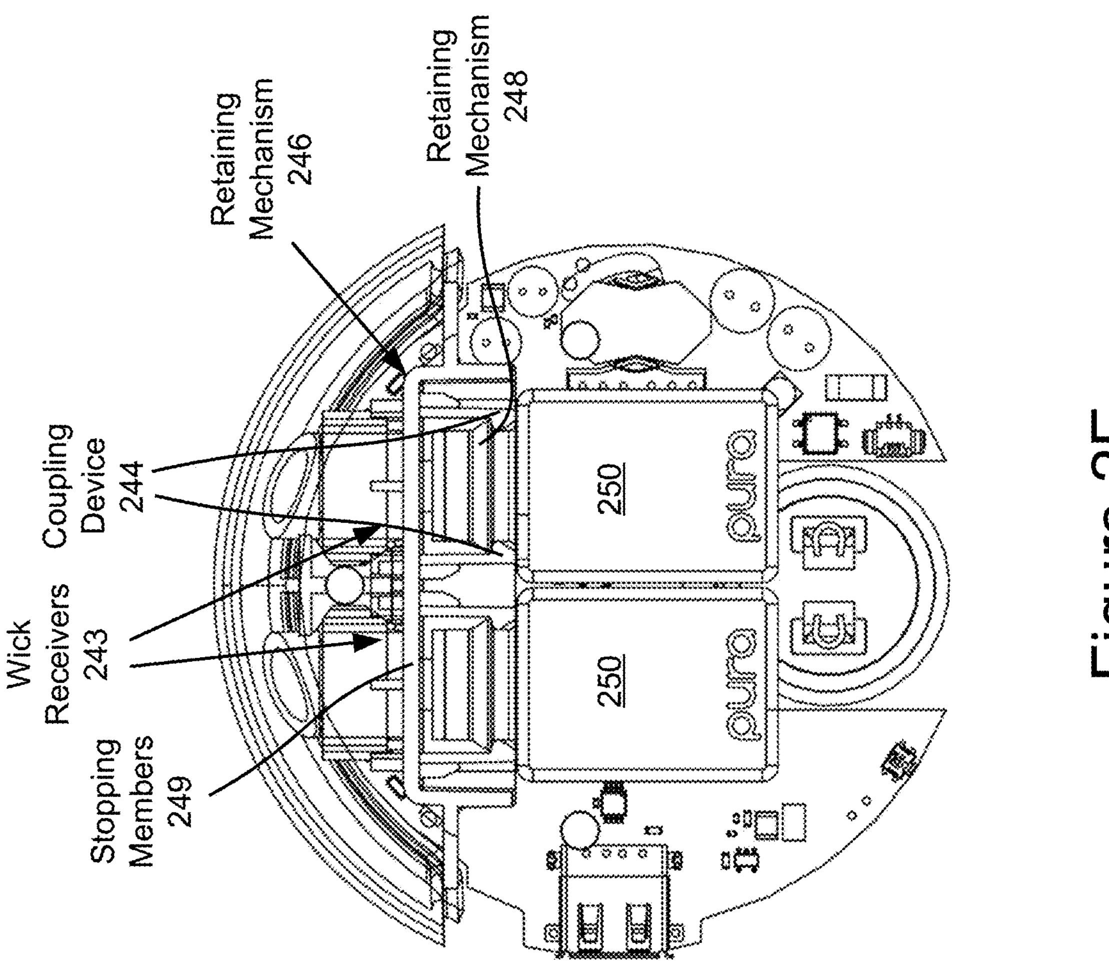
FIGS. 2E-2G are various further views of various components of the example scent dispenser.

In FIG. 2E, a retaining mechanism 248 of the vial 250 couples with a corresponding retaining mechanism 246 included in a slot of the scent dispenser 132. In some embodiments, the vial retaining mechanism 248 may include first and second vial couplings 244. The first and second vial couplings 244 receive and detachably retain the first side 264 of the first and second vials 250, respectively. In some instances, the first and second vial couplings 244 includes one more surfaces shaped to engage with and secure the neck 258 of the first side 264 of the first and second vials 250.

As shown, the retaining mechanism 248 may be a protrusion extending outwardly from a surface of the vial, such as the neck or the body of the vial. In the specific example depicted, the protrusion extends around the circumference of the neck 258 of the vial 250, and the retaining mechanism 246 includes one or more coupling devices 244 that engage with the retaining mechanism 248. In some embodiments, the coupling devices 244 may comprise one or more fasteners formed to detachably engage with the neck of the vial. For instance, the coupling devices 244 may include one or more clips protruding outwardly from a stopping member 249 along the neck 258 of the vial 250 toward the body 256 of the vial 250. The clips include protrusions protruding inwardly toward the neck such that they engage with and hold the protrusion 260 of the neck 258.

It should be understood that other variations for the retaining mechanism 248 and 246 are also possible and contemplated. For instance, the protrusion 260 may engage with corresponding channels formed in a surface of the retaining mechanism 246 into which protrusion 260 slides into an opposing side(s). In another example, the neck 258 includes a grove and the retaining mechanism 246 includes corresponding protrusions or rails that mate with the grove. Numerous other variations are also possible and contemplated.

Figure 2F:
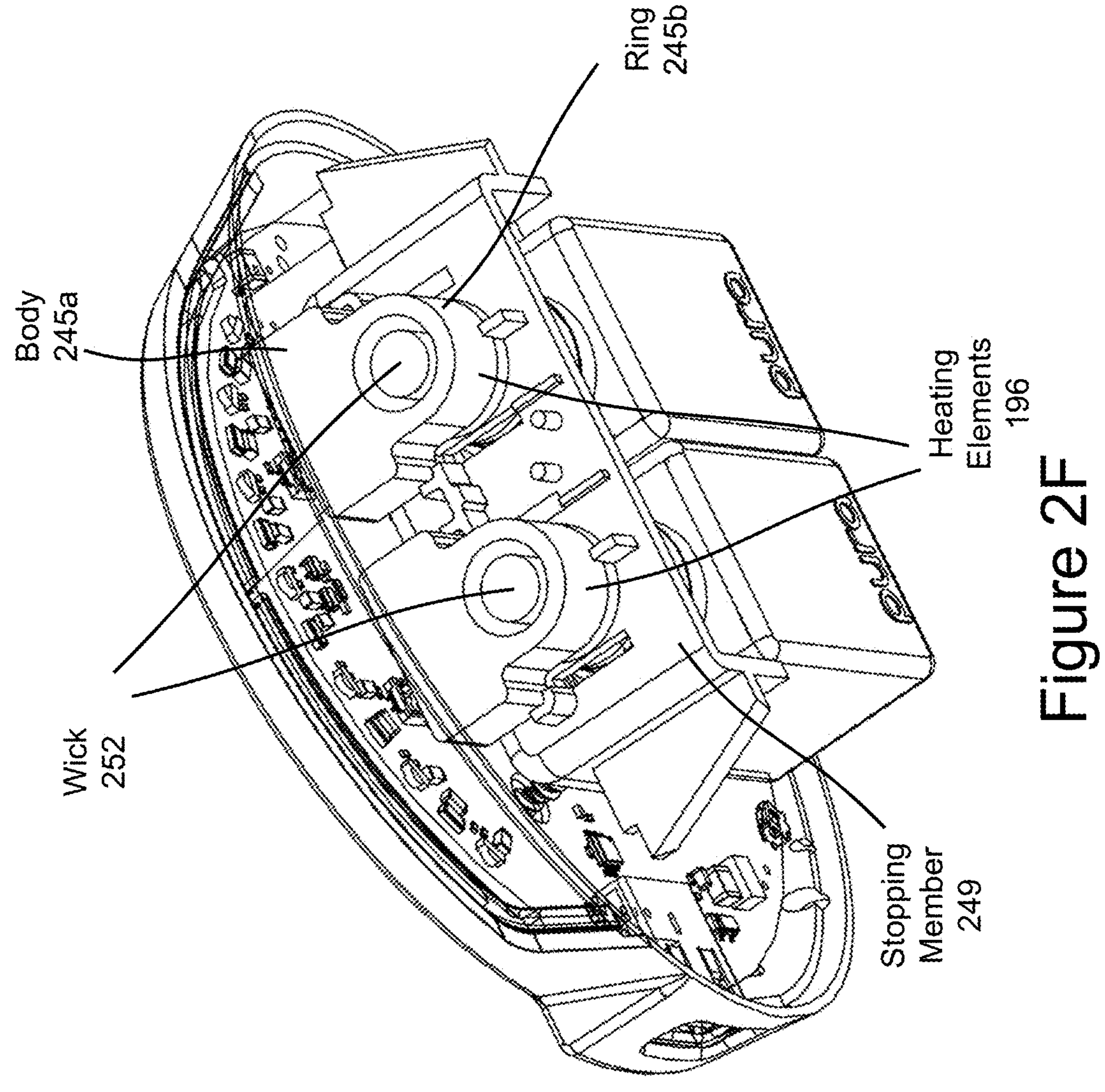
Figure 2G:
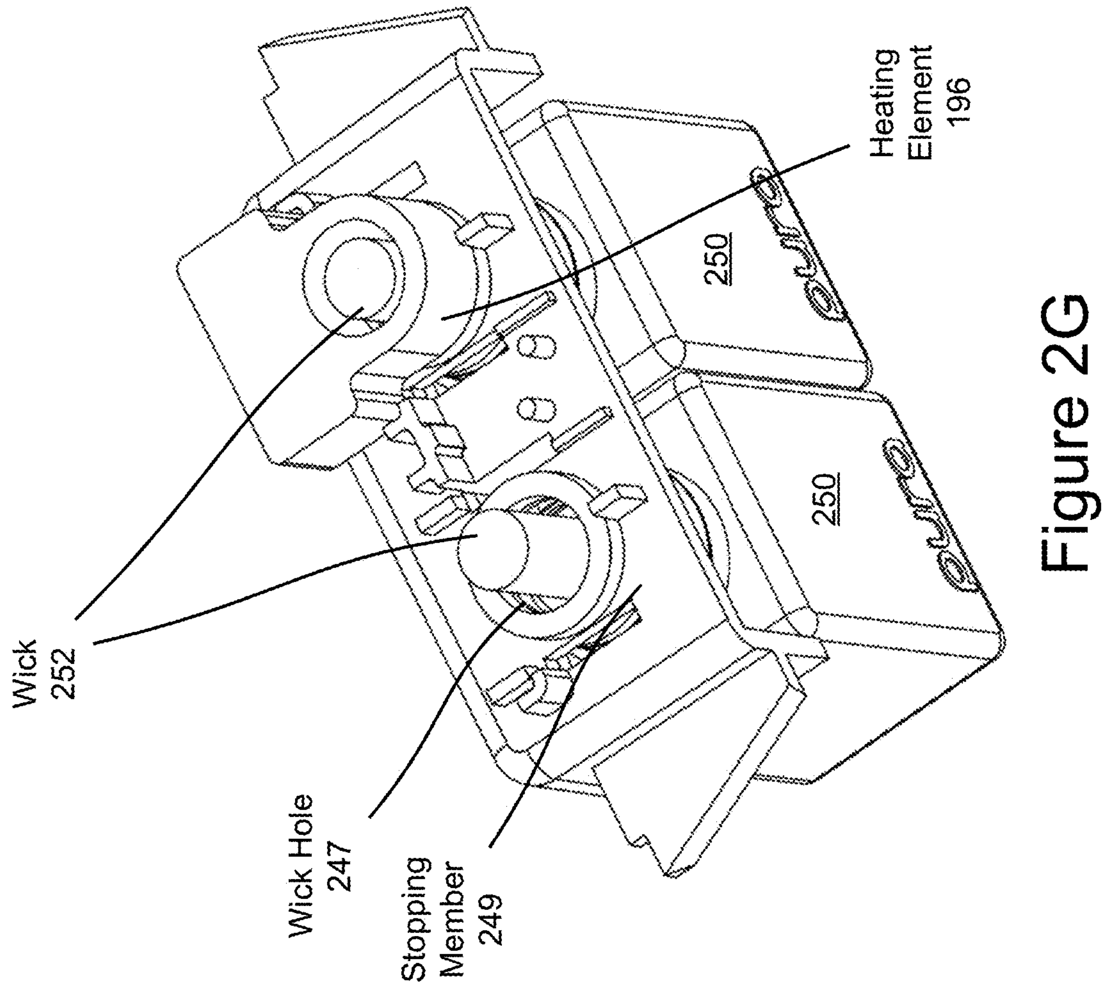

As illustrated in FIGS. 2F and 2G, the scent dispenser 132 may include a heating element(s) 196 to heat the solution from the vial(s) 250 installed in the scent dispenser 132. In some embodiments, the wick 252 passes a scented solution to the heating element 196. The heating element 196 diffuses the scented solution by heating the scented solution to the temperature level regulated by the controller 188.

An example heating element 196 may include a ceramic material (e.g., ceramic resistor, such as a wire wound ceramic heating element). Heating the solution received from the vial 250 accelerates diffusion of the solution into the surrounding air. The housing 200 may include one or more ports 214 in the lid 204 to allow the diffused air to pass into the surrounding environment, as shown in FIGS. 2A and 2B. The more heat applied by the diffusion device, the stronger the evaporative rate and thus the stronger the smell that may be produced.

In some embodiments, a scent solution of a vial 250 may require a certain heating range to be diffused effectively, and the controller 188 may receive specific state settings for that scent solution from the dispenser management application 160 and use those settings to control the temperature of the corresponding heating element 196.

In the depicted embodiment, the vial retaining mechanism 246 includes wick receiver(s) for receiving the end(s) of the wick(s) 252 of the installed vial(s) 250 and passing them to the heating element(s) 196. For instance, the scent dispenser 132 may include a first (e.g., left) heating element 196 situated on a side of the stopping member 249 opposing a first (e.g., left) vial 250, and a second (e.g., right) heating element 196 situated on the side of the stopping member 249 opposing the second (e.g., right) vial. The first heating element 196 heats an end of the wick 252 extending through the wick hole 247 of the first wick receiver 243, and the second heating element 196 heats an end of the wick 252 extending through the wick hole 247 of the second wick receiver 243.

A wick receiver 243 may include a stopping member having a wick hole 247 extending through the stopping member 249 of the wick receiver 243. The wick hole 247 of the wick receiver 243 receives a wick 252 extending outwardly from the opening of the first side 264 of the vial 250 (e.g., see FIGS. 5A and 5B). Multiple wick receivers 243 may be included to match the number of vials being heated.

In some embodiments, a heating element 196 is shaped to receive and heat a wick 252 of a vial 250. For example, the a heating element 196 (e.g., first, second, etc.) may include a ring **245*b* extending from a main body 245*a* that receives the end of the wick 252 extending through the wick hole 247 of the wick receiver 243. In some instances, a metallic heating wire may be wound in the main body 245*a* and the ring conducts the heat around the wick 252**, although other variations are also possible and contemplated.

The electronics (e.g., 235) of the scent dispenser 132 include an intensity control unit that controls the intensity of diffusion by the diffusion device. For example, the controller 188 may use pulse width modulation (PWM) to digitally control the (analog) power provided to a heating element 196 of the diffusion device. The controller 188 is coupled to one or more temperature sensors (not shown but installed proximate and/or on the heating element(s) 196) to measure the temperature of the element(s) 196 and send feedback to the controller 188, which determines whether to increase or decrease the temperature based on the desired intensity setting, which may be stored in state settings in a non-transitory memory device coupled to the controller 188. The intensity setting may be variable based on the time of day or other parameters, and/or user-defined using the scent application 108, as discussed elsewhere herein.

In some embodiments, the diffusion device uses the above described PWM output control and temperature input data in conjunction with a PID (proportional, integral, derivative) control loop firmware algorithm. This is beneficial as it can increase the reliability, robustness, and ruggedness of the diffusion device. With proper system tuning, the PID control can help to ensure that the temperature will more accurately track the desired set point, with less over/undershoot. For instance, the following example code could be used by the controller 188.

```
previous_error = 0
integral = 0
start:
  error = setpoint − measured_value
  integral = integral + error*dt
  derivative = (error − previous_error)/dt
  output = Kp*error + Ki*integral + Kd*derivative
  previous_error = error
  wait(dt)
  goto start
```

In further embodiments, in additional and/or alternative to a PID loop, the firmware may program the controller 188 to use a PI loop or other suitable feedback control loops to control the temperature.

As discussed herein regarding the inventive intensity control performed by the controller 188 in conjunction with the heating element(s) 196, the scent dispensation may be digitally controlled through pulse width modulation (PWM). In some embodiments, the heating element switching discussed herein may also utilize the same or similar hardware and/or software to carry out those operations.

In some embodiments, through algorithmic direction from the instance of the scent application 108 (e.g., smart phone app), via the cloud platform described herein, and thereafter the dispenser's firmware, the hardware may be instructed to set at least one vial diffuser (heating element) to a PWM of zero (thus turning it off) and at least one other to some PWM value above zero (thus turning it on). Similar logic may also perform switching between vials 250. In this example, the scent application 108 software logic, dispenser management application 160 software logic, and/or firmware 194 software logic may prevent and/or allow two or more vial diffusers (e.g., heating element circuitries) from being turned on simultaneously, although for other embodiments, they could be otherwise adapted if necessary.

In some embodiments, the firmware may program the controller to heat multiple elements 196. In some embodiments, the heating of multiple elements 196 may be utilized to mix different scent solutions contained in different vials 250 installed int eh scent diffuser 132. In some embodiments, the heating of multiple elements 196 may be utilized to further increase the scent intensity in a given room in which the scent dispenser 132 is installed. Each scent solution may have a temperature range in which it can be effectively diffused (e.g., without cause burning of the scent solution). As such, a given heating element 196 may have a maximum rate at which a particular scent solution can diffused (maximum temperature the scent solution can be diffused). Advantageously, to increase diffusion beyond the maximum rate for a given vial 250 and heating element 196, the controller 188 may actuate a plurality of heating elements (e.g., a first, a second, etc.) configured to dispense the same scent solution. Further, a scent solution may have a particular temperature at which it optimally diffuses (e.g., below a maximal rate). Using plural heating elements allows the scent to diffuse at this rate while meeting the volume and/or intensity requirements of a given room. The firmware may retrieve state settings (e.g., received from the dispenser management application 160) instructing the controller 198 to heat a plurality of wicks 252 at particular temperatures, and the controller 188 may control the heating of the heating elements 196 accordingly. In further embodiments, the settings for different scents may be preloaded on the dispenser and the dispenser may adjust the heating of different scent solutions based on the store settings. The state settings received from the dispenser management application 160 may include data specifying which vial(s) to diffuse, the temperature at which to diffuse the solution from the vial, how long to diffuse the solution for, etc.

The controller 188 may listen for updated scent settings (e.g., by sending iterative requests to the dispenser management application 160, running a local server configured to listen for update requests including state settings from the dispenser management application 160, etc.). Further, the controller may 188 send check-in requests to the dispenser management application 160 reporting the operational status of the dispenser 132.

In some embodiments, state settings for scent dispenser 132 operation are synchronized with the dispenser management application 160. The interface 190 may utilize any communication protocol that is suitable, such as 801.11 protocols (e.g., Bluetooth, Wi-Fi™, etc.).

The controller 188 may be programmed by the firmware to update the state settings when a user modifies the settings using an instance of the scent application 108 operating on his/her user device. The scent application 108 may transmit new and/or updated settings to the dispenser management application 160, which is programmed to then synchronize the settings with the scent dispenser 132 if applicable. In addition, if the scent dispenser 132 is ever turned off, and/or the state settings are lost somehow (e.g., due to malfunction or power disruption), the scent dispenser may be reinitialized (e.g., by the controller 188 downloading the state settings and configuring the hardware of the scent dispenser 132 based on the settings). The controller 188 may receive settings via the interface 190 and update the settings stored in the non-transitory memory of the scent dispenser 132. The non-transitory memory may be embedded in the controller 188 or may be a separate device that is coupled to the controller 188. In some embodiments, the microcontroller may include MOSFET circuitry, the interface 190, firmware, etc.

Any state information of the scent dispenser (e.g., the volume, available vials, vial in use, diffusion level, current LED color, etc.) can be communicated, via a wireless transceiver (e.g., the interface 190) electronically coupled to the controller 188 that controls the above-noted electrical components, via the network 102 (e.g., the Internet) to the server 150, which may relay the information via the network 102 to the scent application 108 operating on a computing device 106 of a user 112 (e.g., mobile device) that is associated with that scent dispenser 132. This advantageously allows the user to view and react to the information in real time.

In some embodiments, the controller 188 may be electronically coupled (e.g., wired, wirelessly) to a motion sensor 186 (e.g., a passive infrared sensor (PIR), photocell, other suitable motion sensor, etc.) reflecting the presence or absence of people within a room in which scent dispenser(s) 132 are installed. The motion sensor 186 in some cases may be a device embedded in the scent dispenser 132 and/or may be a separate device that is installed in the premises and electronically coupled to the scent dispenser 132. Other variations are also possible and contemplated.

Based on a predetermined duration of inactivity (e.g., no motion detection signals received from the motion sensor 186), the controller 132 may deactivate the heating elements 196 and suspend operation of the scent dispenser 132, or may reduce the diffusion intensity by a certain percentage or to a certain minimal threshold, to economize the scent solution. In the latter example, upon detecting motion within the room via the motion sensor 186 (e.g., based on a detection signal received from the motion sensor 186), the controller 188 may restore and/or increase diffusion. Data regarding presence in a given room through the day may be transmitted to the dispenser management application 160, stored as premises data 180 in the data store, and used to generate analytics about user preferences, such as whether users prefer to scent a room even though users aren't present, whether users prefer to scent a room only if users are present, whether users prefer to maintain a minimal scent in a room if users aren't present, etc. This may be determined using the usage data because the usage data may be time and/or date coded so that the rate of use, as well as the time of day, day of week, etc., usage occurred may be determined by the dispenser management application 160.

In some embodiments, the controller 188 may receive wireless signals broadcasted by other devices within transmission range, determine if the signals are broadcasted by other scent diffusers 132, process the strength of the signals belonging to the other scent diffusers 132, and adjust scent diffusion based on the signal strength of other scent diffusers 132 that satisfy a predetermined signal strength threshold, as discussed in further detail with reference to at least FIG. 8.

Figure 3A:
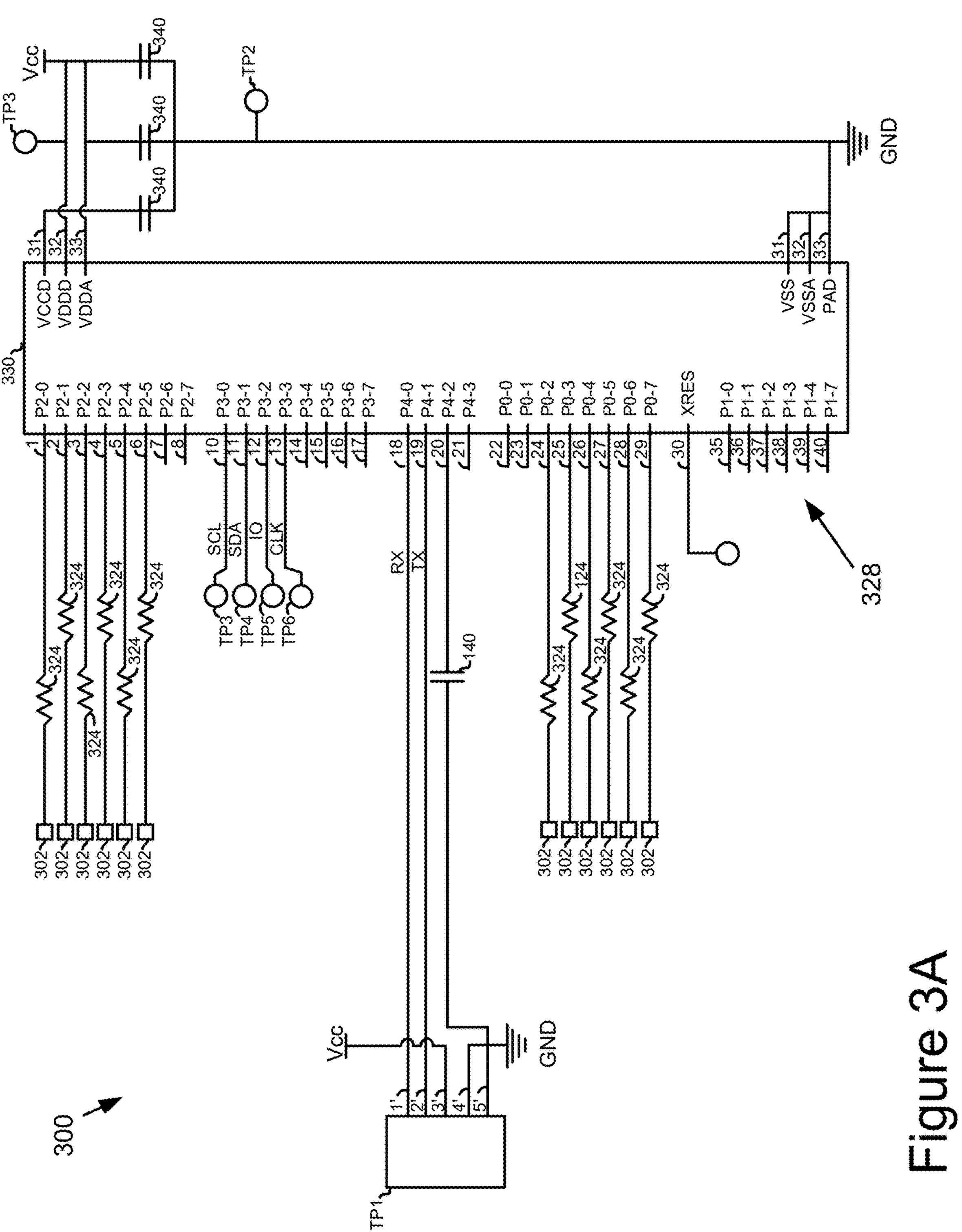
FIG. 3A is a schematic diagram of an example vial sensor.
Figure 3B:
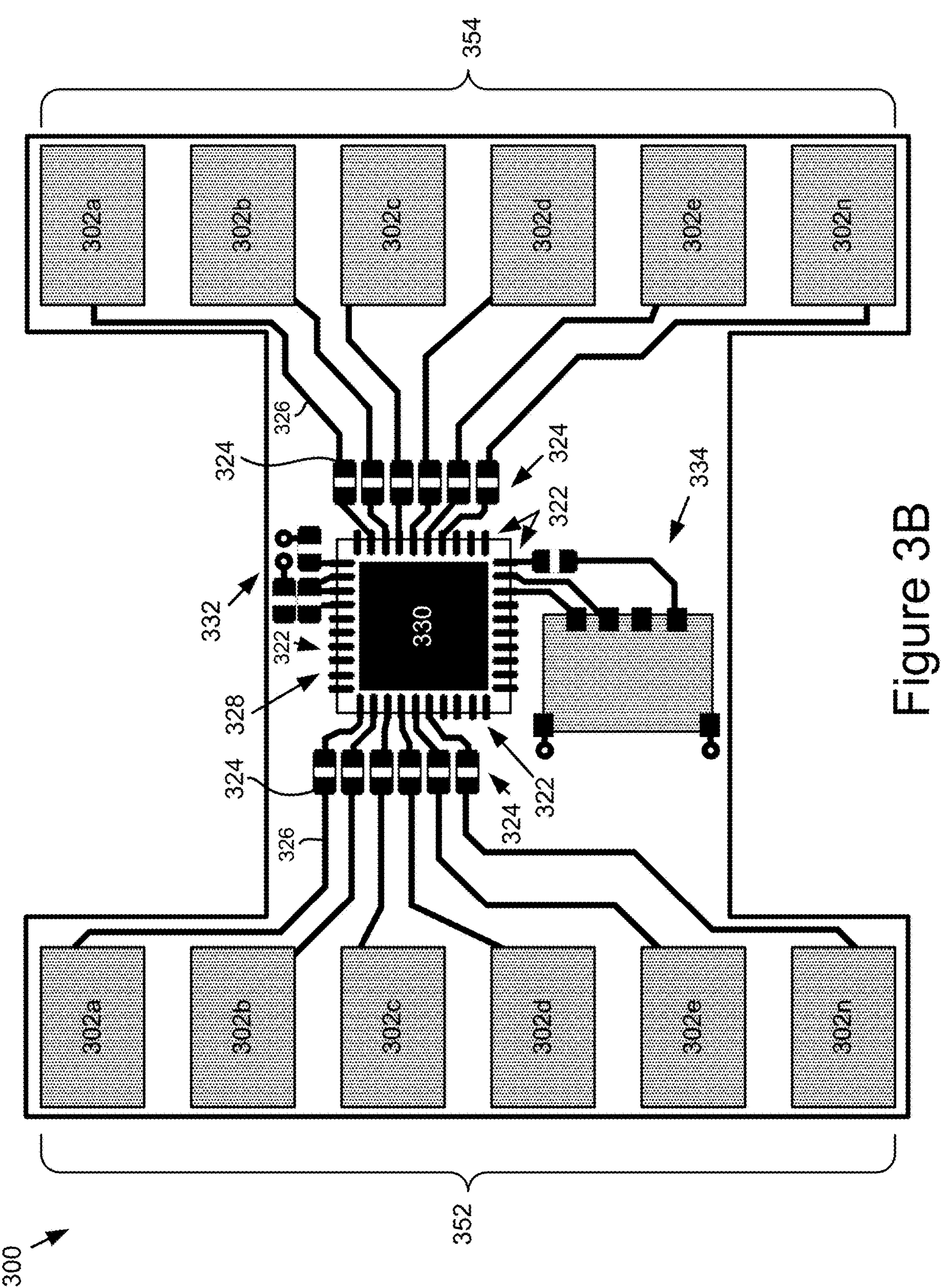
FIG. 3B is a block diagram of an example vial sensor.

FIGS. 3A and 3B depict various aspects of an example vial sensor 300.

In some embodiments, the vial (e.g., volume) sensor 300 may be a sensing device for determining the volume level of the vial. The vial volume sensor may include a sensor, which produces an electric field. As the liquid volume in the vial 250 changes, the sensor 300 detects a change in the electric field and correlates the change into a volume change. Predetermined coefficients may be used by the controller 188 and/or 328 to perform the correlation and determine the vial volume reliably. In some cases, the sensor 300 is a capacitive sensing device, which is advantageous because it is inexpensive, robust, and uses a noncontact approach which reduces the probability of failure of the component over time due to the buildup of dirt, chemicals, etc. However, it should be understood that other ways of sensing the vial volume are also applicable, such as resistive, transmission line techniques (e.g., a probe sensor, etc.), and are encompassed by this disclosure.

FIG. 3A is a schematic diagram of an example vial sensor 300 and FIG. 3B is a block diagram of the example vial sensor 300. As shown, the vial sensor 300 includes a plurality of pads 302 that are wired to a controller 328. The pads 302 may belong to one or more arrays. As shown, the vial sensor 300 includes two arrays of pads 302 (those wired to ports P2-0 through P2-5 and those wired to P0-2 through P0-7). The controller 328 electrically charges the sensor pads 302 of each array, and detects a change in the signals received from the array, and determines a corresponding change in the fluid level of the scented solution of the vial.

A non-limiting example of the controller 328 may include an ARM-based microcontroller, such as one manufactured by Cypress Semiconductor under PN CY8C4124LQI-443, although it should be understood that other chip architectures are also applicable, that the controller 328 may be combined with other processors, and/or that numerous other variations are possible, contemplated, and applicable.

Further, as shown in FIG. 3B, the vial sensor 300 may include the controller 328 including pins 322 and a chip 330, resistors 324 connecting various pins 322 of the controller 328 to first, second, etc., arrays 354 of pads 302*a*-302*n* (e.g., via wires 326), a set of capacitors 332 to regulate the voltage powering the controller 328, and a testing and/or firmware flashing module 334.

It should be understood that the shape and dimensions of the pads 302 may vary based on implementation. Thus, while a certain number of pads (e.g., 6) of an array 322 are used by example to describe the vial sensor 300, any suitable number of pads 302 may be used to provide the functionality and benefits described herein. For Instance, the sensor pads 302 may be nested, narrower, larger, horizontally or vertically disposed, place in a multidimensional array, etc.

In some embodiments, the wires 326, pads 302, and/or trace patterns 326 may comprise a conductive material, such as metal (e.g., PCB copper). The controller 328 may be programmed using firmware, which may be stored in an embedded or separate non-transitory memory device and loaded upon initialization of the scent dispenser 132. The firmware may program the controller 328 to sense the vials 250 as described herein, and provide sensory output to the controller 188 and/or other components.

In an example embodiment, the pads 302 of an array 322 may be spaced 1-2 mm apart and may include a plurality (e.g., 2, 3, 4, 5, 6, 7, 8, etc.) copper sensor pads, although other spacing dimensions, pad sizes, and number of pads may be used, as described elsewhere herein. In some instances, various pads 302 (e.g., top and bottom corner pads) may be connected through jumper options that allow for driven shield, ground, and normal sensor pad connection options. Further, sensor pad connections may be in series with in-line resistors to the chip pins 322 of the controller 328.

The circuitry/electronics of the vial sensor 300 may include resistors 324 between the pins of the microprocessor 328 and the sensor pads 302 to adjust the current being applied to the sensor pads 302 so they consistently charge to a level that allows for an electric field emitted by them to pass through the air between the sensor pads 302 and an adjacent vial sidewall 266 so the presence and/or absence of a solution contained in the vial 250 adjacent to the pad 302 may be detected. Further electronics of the vial sensor 300 may include resistors 324 located near the line of where a center line of an H-shaped vial sensor 300 meets a sensor region; I2C PSOC connections for tuner connectivity; digital ground pours on top/bottom of the PSOC mounting area, etc., although other variations are also possible and contemplated.

Figures 4A, 4B:
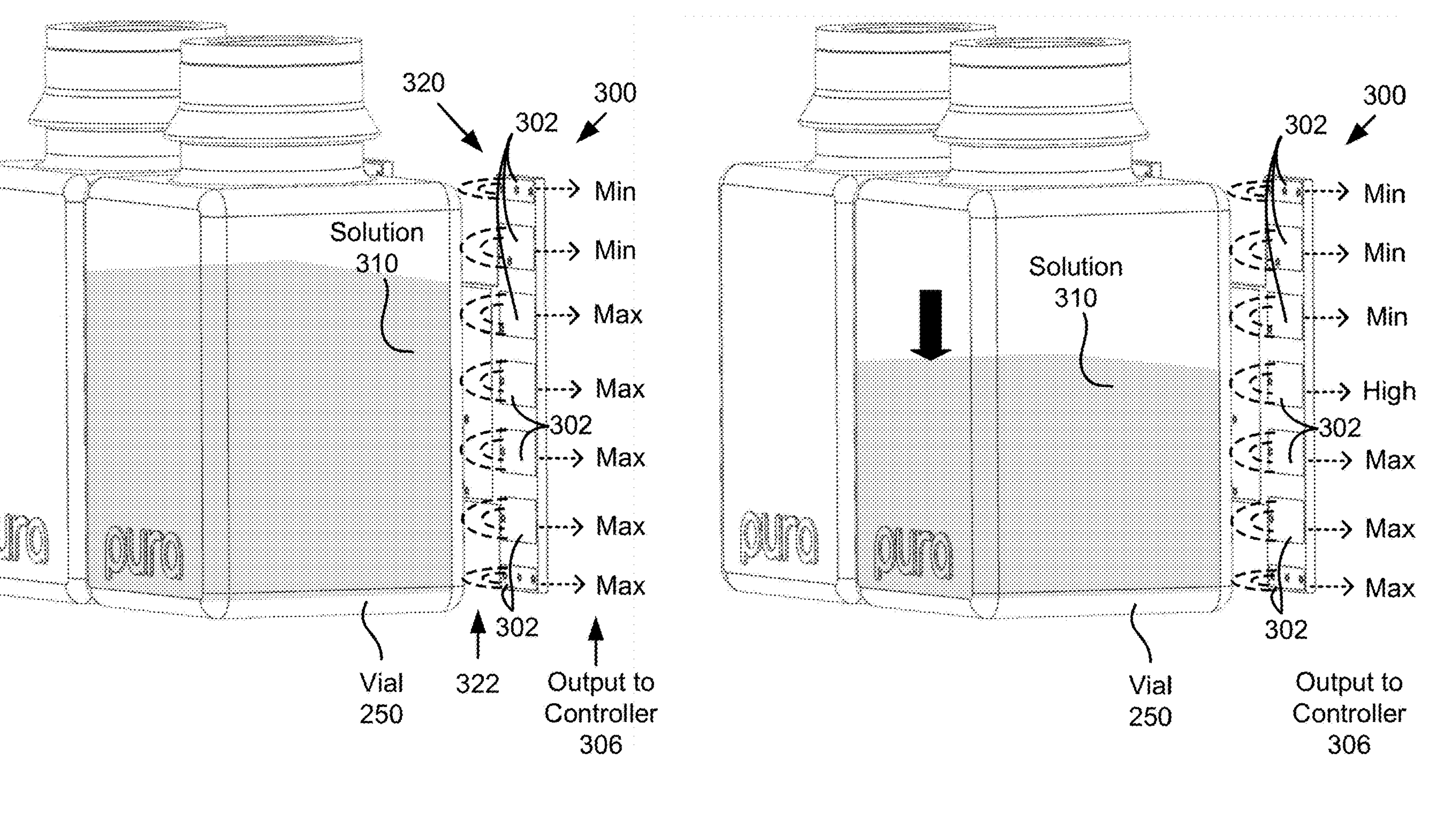
FIGS. 4A-4D are block diagrams depicting a progression for sensing a solution level of a vial using the vial sensor.
Figures 4C, 4D:
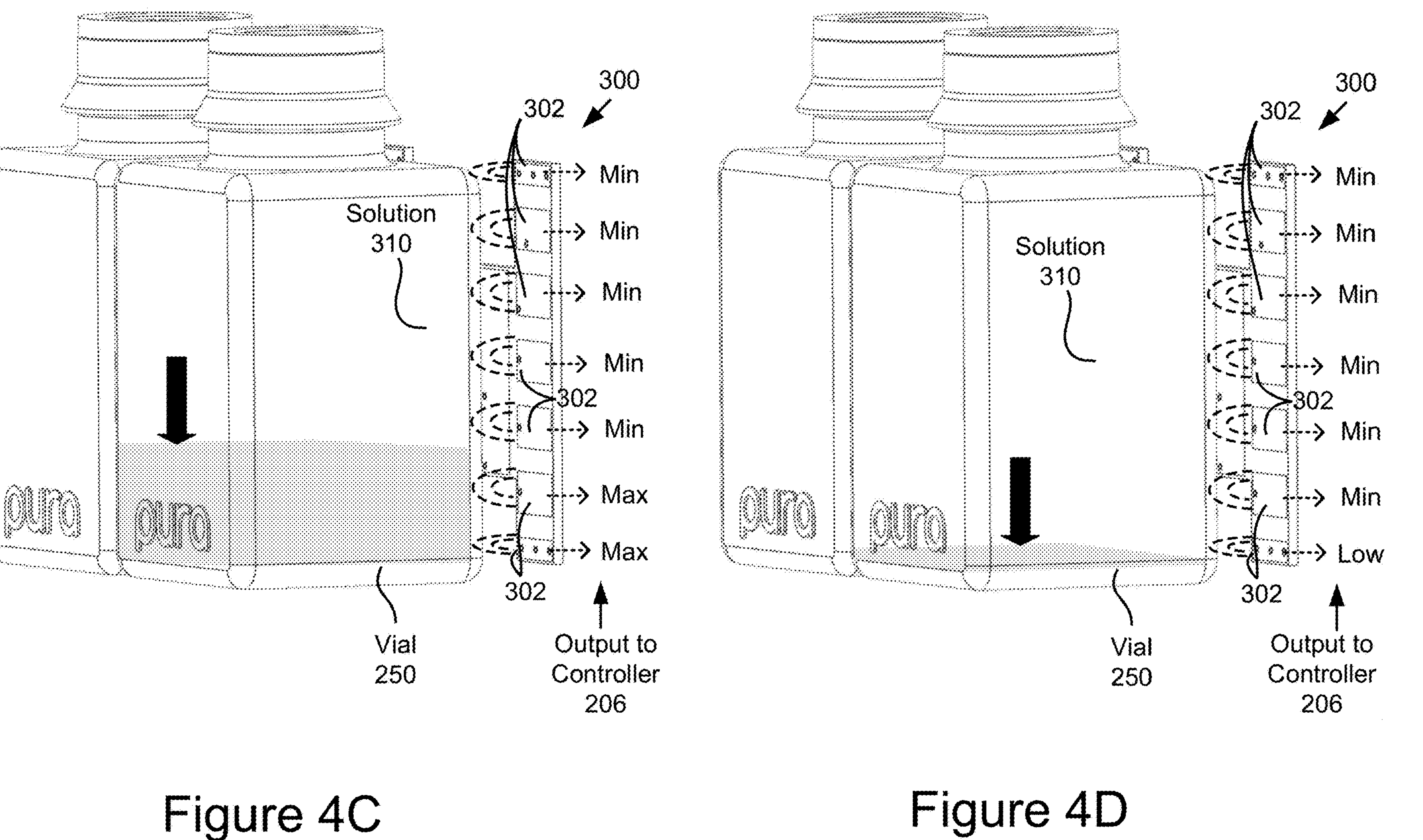

FIGS. 4A-4D are block diagrams depicting a progression for sensing a solution level of vial(s) 250 using a vial sensor 300. In FIG. 4A, the vial 250 is relatively full (e.g., 80%) of scent solution 250. The array of sensor pads 302 are electrically coupled to a controller and charged. A sidewall of each vial 250 is situated adjacent to a corresponding array 320 of sensor pads 302 (e.g., at a certain distance, which may predefined) within an array of electric fields 322. The array 320 of sensor pads 302 are electrically charged by the microcontroller 128 (responsive to an actuation signal from the controller 188 using power from the PS 184) to produce the array 322 of electric fields. The controller 328 detects changes in one or more of the electric fields 322 of the array as the solution 310 is dispensed from the corresponding vial 250 (responsive to heating by a corresponding heating element 196).

The vial sensor 300 may include any number of (e.g., two or more) arrays 322 of sensor pads 302 that are respectively arranged in alignment with the (e.g., two or more) vials 250 retained by the (e.g., two or more) vial couplings (e.g., coupling device(s) 244). For instance, arrays 320 of sensor pads 302 may be situated along various sides (e.g., first, second, left, right, middle, etc.) of the vial sensor 300. Each array 320 of sensor pads 302 may be arranged in alignment with a corresponding vial 250 retained by a corresponding vial coupling, such as a vial coupling of the retaining mechanism 246. In embodiments, with multiple vials 250, the controller 328 charges multiple arrays 322 to sense the fill level of those vials 250.

As the solution is used up 310, and the fill level (also called fluid level or solution level) goes down, the signals provided by the sensor pads 302 change. For example, the signals 306 that are output to the controller 328 and/or 188 in FIG. 4A reflect that the bottom four sensor pads 302 detect a maximum capacitance reflecting that the portions of the vial 250 corresponding in location to those sensor pads 302 are full. However, the top two sensor pads 302 detect a minimum capacitance reflecting that the portions of the vial 250 corresponding in location to those sensor pads 302 are empty. The controller 328 and/or 188 may aggregate the signals and determine an overall fill level (e.g., 80%, 50%, 20%, 1%, etc.). As the solution is dispensed during operation, the solution level 310 drops, and as a result, the output to the controller 306 changes (e.g., in FIG. 4B, three pads register a minimum capacitance, one registers an high capacitance (e.g., less than the maximum but closer to the maximum than the minimum), and three register a maximum capacitance; in FIG. 4C, five pads register a minimum capacitance and two pads register a maximum capacitance; and in FIG. 4D, six pads register a minimum capacitance and one pad registers a low capacitance due to a trace amount of solution being left in the vial 250). The controller 188 may transmit usage data, such as the rate at which the solution of each vial drops, as determined using data from the vial sensor 300, to the dispenser management application 160 for storage and/or use in generating analytics, as described in further detail herein. In some embodiments, the output 306 may be output on a cycle, such as the duty cycle of the controller 328 and/or 188, although other timing variations are also possible and contemplated.

The controller 328 may detect changes in the one or more of the electric fields 322 as the solution 310 is dispensed from the corresponding vial 250. For clarity, the term controller, as used herein, may refer to the controller 188, the controller 328, or both the controller 188 and the controller 328, unless specifically described otherwise.

In some embodiments, the controller 188 may be electrically coupled to heating element(s) 196 and electrically coupled to array(s) of sensor pads 302 via the controller 328. The controller 188 may regulate the temperature level of the heating element(s) 196, and the controller 328 may receive signals from the array(s) 322 of sensor pads 302, and provide the signals to the controller 188 for processing. The controller 188 may process the signals to determine a fluid level of the vial(s) 250 and/or may relay the signals to dispenser management application 160, which may store the signals as usage data 178 in association with the scent dispenser 132 and/or vial(s) 250 and/or scent being dispensed (using their corresponding IDs). In some cases, a change in a signal received from a pad 302 may reflect a change in capacitance due to a reduction in the solution near the pad 302.

The controller 188 may be programmed to switch between, and or include multiple, vials 250 in implementation where a plurality of heating elements 196 and vial slots 222 are included in a scent dispenser 132. The circuitry of the heating elements 196 may include a switch mechanism allowing for independent control and/or heating of the heating elements 196.

The heating element switching mechanism includes executable firmware logic and the switching circuitry of the heating elements 196. The heating element switching mechanism is configured to switch between the different solutions contained in the vials 250 so the scent dispenser 132 can diffuse different scents at different times. The controller 188 can control the operation of the heating element 196 based on a user-defined schedule or on-demand based on a user instruction submitted via the scent application 108 operating on the user's computer device 106. In addition, in some cases, the controller 108 can automatically instruct the heating element switching mechanism to switch from using one vial 250 to another vial 250 when the first vial 250 has run out of solution. Once switched, the previously active heating element 196 is switched off and another heating element 196 is turned on, which results in the scent heated by the other heating element 196 to begin diffusion and the former to cease diffusion. Further, the switching mechanism can allow for multiple heating elements 196 to be active at the same time at the same or different temperature levels, depending on the settings received from the dispenser management application 160.

Figure 13:
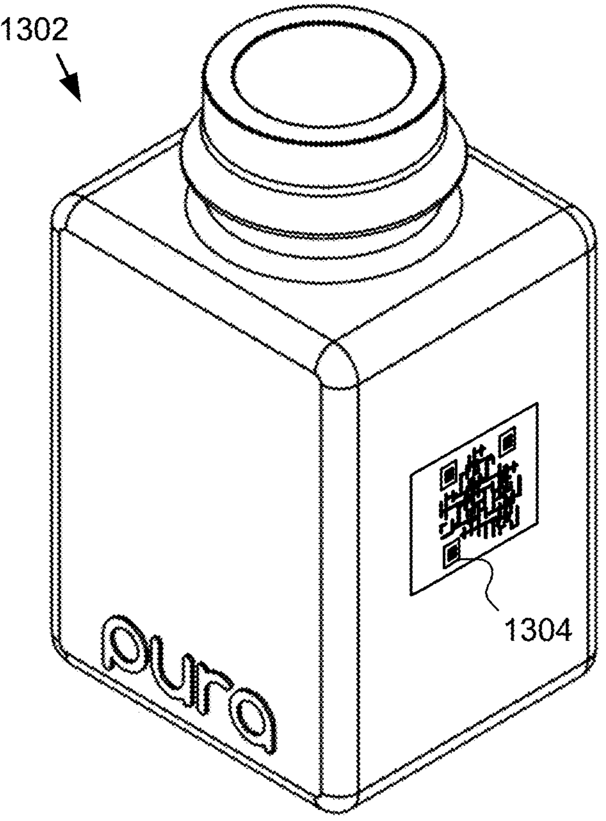
FIG. 13 is a front perspective view of an example vial with a scannable optical representation.

Additionally, the scent dispenser 132 described herein may further amplify the efficiency of switching between or to include multiple scents. In some embodiments, to do so, the scent dispenser 132 utilizes a combination of additional software logic and the inclusion of bar and/or detectable objects (e.g., QR codes) on the vials 250. FIG. 13 depicts an example vial 1300 that includes an example detectable object 1302. The scent dispenser 132 may include an optical sensor to capture the detectable object 1302 and determine the identity of the vial 1300 based thereon.

In an example, a camera, scanner, etc., included on the main board 235 may scan a vial 250 upon insertion into a slot of the scent dispenser 132. The controller 188 may receive the captured data and identify the vial 250, and/or send the captured data to the dispenser management application 160, which may in turn identify the vial 250 and indicate the slot in which the vial 250 is installed. Upon identification of the vial 250, the controller 188 may load the scent diffusion settings for that vial 250 and slot (e.g., heating element 196), such as the temperature, heating duration, whether to actuate other output devices 192 and the parameters for actuating those output devices 192 (e.g., LEDs, audio reproduction device(s), etc.).

In another example, upon the user receiving a new vial refill, the scent application 108 executing on the user's mobile device may prompt the user 112 to either manually select within the scent application 108 the correct scent of the their new refill, or alternatively, utilizing an image capture device of the user's mobile device (e.g., the user's phone's bar code scanner/camera) to scan the detectable object, such as unique graphical image included on the vial 250 (e.g., the bar code, QR code, etc., on the vial). The scent application 108 and/or the dispenser management application 160 may identify specifically which scent solution the vial 250 contains and then associates it with the correct vial slot/insert position 222 in the dispenser 132 (e.g., by querying a table that includes this information using the unique identifier associated with the unique graphical image). This scanning process adds simplicity for the user and also increases the integrity of the collected data analytics. It also verifies which vials 250 are being used and can prevent counterfeit vials 250 from being used. This is advantageous, as some solutions that are homemade or non-authentic could be flammable, toxic, cause respiratory distress, or other issues.

In some embodiments, room profiles stored in the data store 170 and/or in a local memory, and may be used to control the level of diffusion and which scents are diffused by the scent dispenser over time. In addition, the room profile may include color and intensity settings for the devices of the scent dispenser, such as one or more lights (e.g., LEDs) included in the scent dispenser. The LED(s) may be variable LEDs that can produce virtually any color. These colors may be correlated with the scent being diffused from the different vials included in the scent dispenser to produce a different mood (relaxing, energetic, etc.) for the room at different times of the day, times of year, etc. The controller 188 may reference the state settings (e.g., reflecting the room profile) to determine how to control the level of intensity of diffusion, which vial 250 should be active, the level of intensity of the output devices (e.g., LEDs), the characteristics of the output devices (e.g., color, sound, etc.). Additionally or alternatively, the user may set the parameters of the output devices (e.g., intensity and color of the LED(s)), remotely using the scent application 108, which the scent dispenser may receive and then implement responsive to receiving corresponding state settings from the dispenser management applicant 160.

Figure 6:
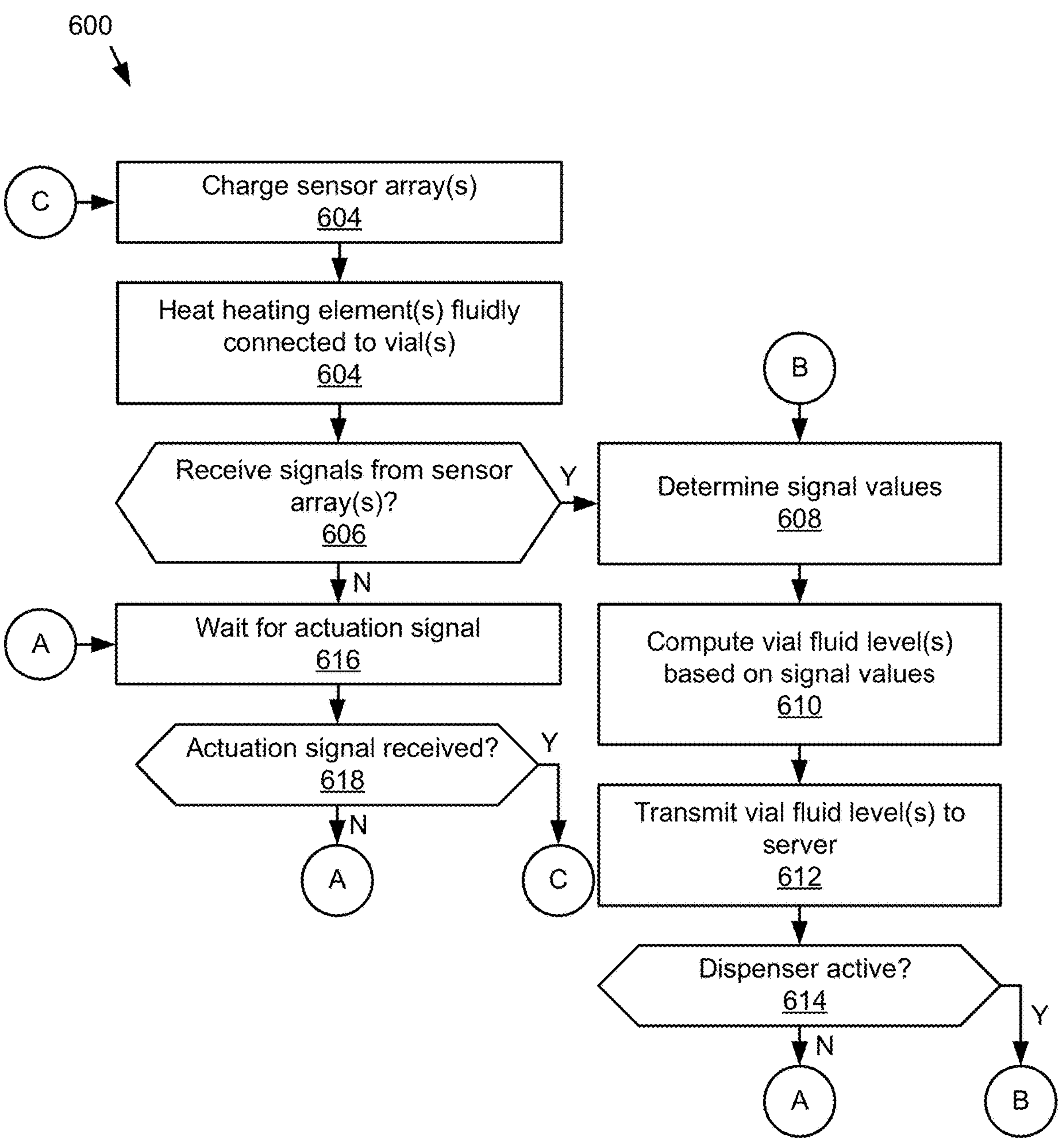
FIG. 6 is a flowchart of an example method for sensing vial volume.

FIG. 6 is a flowchart of an example method 600 for sensing vial volume. In block 602, the method charges the sensor array(s) 322, and in block 604, the method 600 heats heating element(s) 196 that are fluidly connected to the vial(s) 250. In some embodiments, wick(s) 252 may fluidly connect the heating element(s) 196 with the vial(s) 250. In further embodiments, the vial(s) 250 may be fluidly coupled to the heating element(s) 196 using other arrangements, such as heating the vial(s) 250 themselves, dripping scent solution into the vial(s) 250 (e.g., using a gravity fed configuration where the vial(s) 250 are still upside down), etc.

In block 606, if the method 600 receives signals from or more sensor arrays 322, the method 600 may proceed to determine the signal values in block 608, compute vial fill level(s) using the signal values in block 610, and transmit, in block 612, the vial fill level(s) to the dispenser management server 150 for processing and/or storage by the dispenser management application 160.

In block 614, the method 600 determines whether the dispenser 132 is still active, and if so, proceeds to block 606 for another iteration. If, in block 614, the dispenser 132 is no longer active (e.g. the scheduled scent diffusion presented, the scent dispenser 132 is inactivated (sometimes referred to as turned off), a loss of power occurred, etc.), the method 600 returns to block 616 and awaits actuation of the scent dispenser 132. Method 600 may check (e.g., routinely, etc.) to see whether an actuation signal has been received, and upon receiving an actuation signal (e.g., responsive to a timer triggering, responsive to receiving state settings from the dispenser management application 160, etc.), may return to block 602 and repeat the method 600. If in block 608, the signals of the received from the sensor array(s) 322, the method 600 may wait until the signals received before proceeding to block 608, and if too much time passes, may report an error and exit. If, in block 618, no actuation signal is been received, the method 600 may continue to stay active and wait for an actuation signal to proceed.

Figures 7A, 7B:
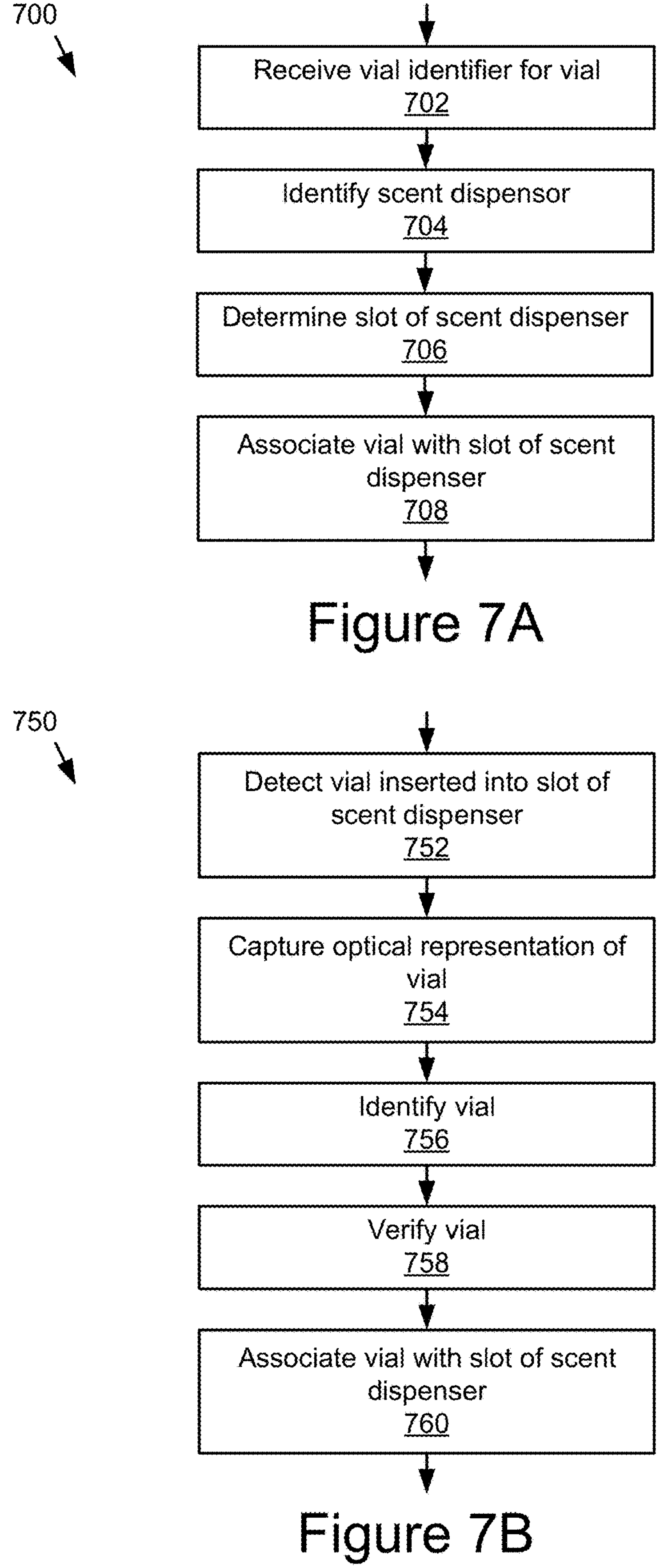
FIG. 7A is flowchart of an example method for activating a vial.
FIG. 7B is flowchart of a further example method for activating a vial.

FIG. 7A is flowchart of an example method 700 for activating a vial 250. In block 702, the scent application 108 may receive a vial identifier for the vial 250. For example, using the user interface, the user 112 may enter the vial identifier using an input device of a user device 106 that is executing the scent application 108. In a further example, the user may capture an image object include on the vial 250, and the scent application 108 may process the captured image object to determine the vial identifier. Other variations are also possible and contemplated.

In block 704, the scent application 108 may identify the scent dispenser 132. For example, the user may input an identification of the scent dispenser 132 into which the user intends to install/has installed the vial 250, or the scent application 108, using fill level data for the scent dispensers 132 registered to the user 112. Based on the data stored in the data store 170, the scent application 108 may provide a list of empty vials 250 that are installed in the scent dispensers 132, and/or suggest the user replaceable of those vials 250 with the vial 250 corresponding to the vial identifier specified in block 702.

Upon identifying the scent dispenser 132 into which the vial 250 is to be installed, the scent application 108 determines, in block 706, into which slot 222 of the scent dispenser 132 user intends to install/has installed the vial 250. This may be based on a user selection of the slot 222 using an input device of the user device 112 and a corresponding user interface presented by the scent application 108, and/or based on a recommendation to the user on which vial 250 to replace based on the fill levels of the determined scent dispenser 132.

In block 708, the scent application 108 and/or the dispenser management application 160 may associate the vial 250 with the determined slot 222 of the scent dispenser 132. For example, the dispenser management application 160 may store dispenser data reflecting the installation of scent in the slot 222 and/or associating a unique vial identifier with the slot 222. This information may be used to generate analytics, often in conjunction with a multiplicity of other users, to determine user scent preferences behavior and generate corresponding data visualizations and graphical user interfaces for navigating the analytics.

FIG. 7B is flowchart of a further example method 750 for activating a vial 250. In block 752, a sensor 186 of the dispenser 132 detects that the vial 250 is inserted into one of the slots of the scent dispenser 132. In some embodiments, the vial sensor 300 may detect the presence of the vial due to a large change in capacitance. In some embodiments, an optical sensor may detect the change in light, and RF reader may detect the presence of a corresponding RF tag included on the vial 250, or a touch sensor may detect the presence of the vial 250 by coming into contact with it. Other variations are also possible and contemplated.

In block 754, the sensor 186 may capture the unique identifier of the vial 250. In some embodiments, the unique identifier may be embodied by an optical representation included on the vial 250, such as one scannable using an optical sensor. In some embodiments, the unique identifier may be transmitted via radio frequency responsive to an RF tag being placed proximate to an RF reader. In some embodiments, the color of the vial 250, or some other visual representation, may be captured by sensor 186 of the scent dispenser 132 and used as and/or processed into a unique identifier. As shown in FIG. 13, and an embodiment may use a QR code 1302, and the sensor 26 may be a scanner configured to scan and interpret the QR code 1302.

In block 756, the sensor 186 and/or the controller 188 may process the captured data to identify the vial 250. Some embodiments, the controller 188 may cooperate with the dispenser management application 160 to decrypt the captured data and determine a unique identifier for the vial. In block 758, the controller 188 and/or the dispenser management application 160 may use the unique identifier for the vial 250 to verify the viability of the vial. For example, if the vial 250 is brand-new, the data store 170 may include data reflecting the existence of the vial 250 and that the vial 250 is never been used and are installed in a scent dispenser 132. In another example, the vial 250 has been partially used, the data store 170 will include usage data reflecting that usage and that the vial 250 has never been used to depletion, and as such, will allow for continued use of the vial 250 (e.g., provided in some cases that the scent solution included in the vial 250 is unexpired). In a further example, if the usage data stored in the data store 170 reflects that the vial 250 in use is used to completion, or in other words all of the scent solution have been used, then the dispenser management application 160 and/or the controller 188 may prevent the scent dispenser 132 from dispensing scent from the vial 250. Further, the dispenser management application 160 may detect when a vial 250 might somehow go from the 50% fill level to an 80% fill level based on sensor data received from a vial sensor 322, thus indicating that a user may have filled the vial 250 with additional solution. In this case, since heating the unknown solution could yield harmful effects, the dispenser management application 160 and/or the controller 180 may prevent usage of the vial 250 in the scent dispenser 132.

In block 760, the scent application 108 and/or the dispenser management application 160 may associate the vial 250 with the determined slot 222 of the scent dispenser 132. For example, the dispenser management application 160 may store dispenser data reflecting the installation of scent in the slot 322 and/or associating a unique vial identifier with the slot 222. This information may be used to generate analytics, often in conjunction with a multiplicity of other users, to determine user scent preferences behavior and generate corresponding data visualizations and graphical user interfaces for navigating the analytics.

Figure 8:
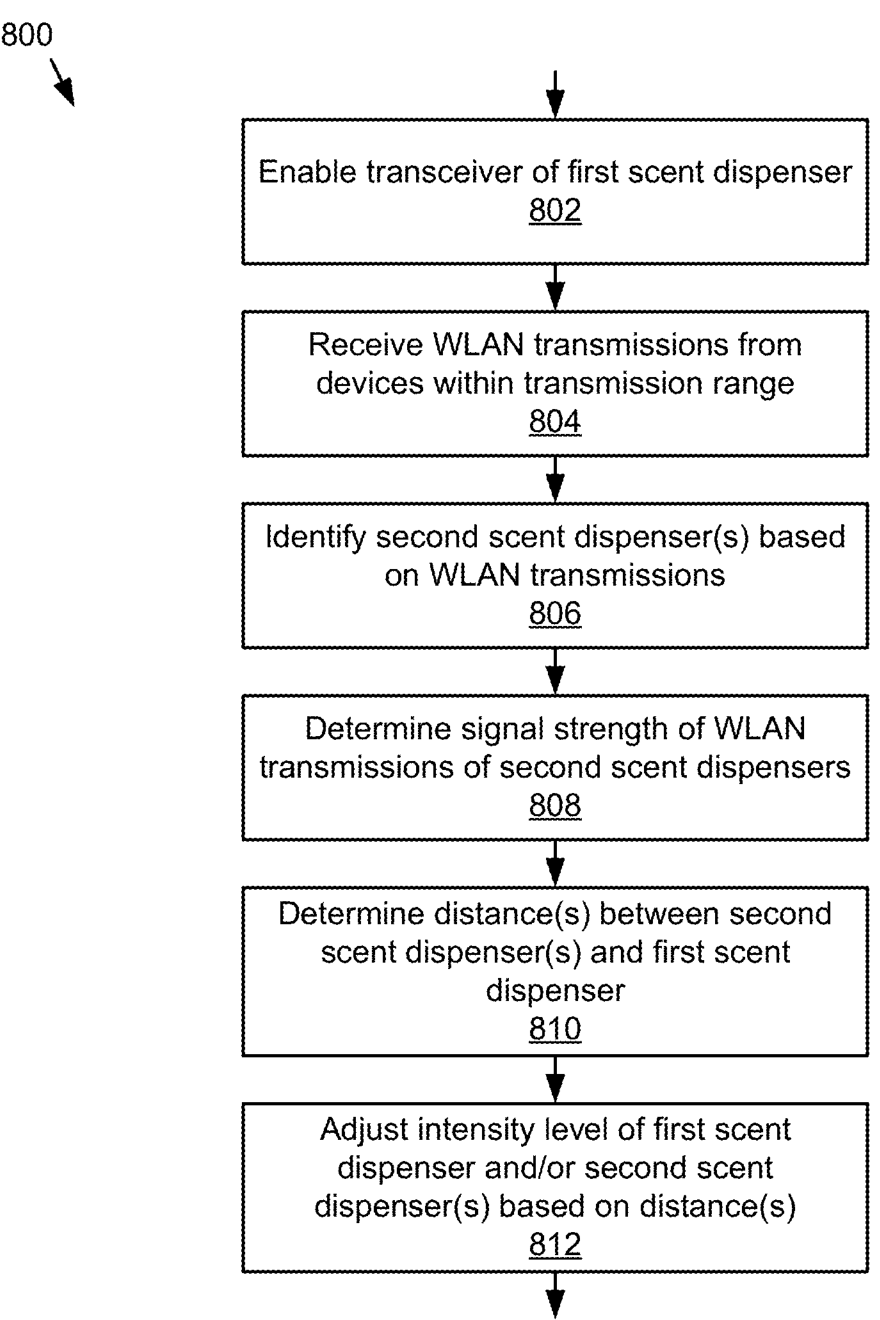
FIG. 8 is a flowchart of an example method for automatically adjusting the dispensation intensity of a scent dispenser based on the presence of nearby scent dispensers.

FIG. 8 is a flowchart of an example method 800 for automatically adjusting the dispensation intensity of a scent dispenser 132 based on the presence of nearby scent dispensers 132.

In block 802, the controller 188 of the first scent dispenser 132 enables an interface 190 of the first scent dispenser 132, and upon doing so, receives in block 804, wireless local area network (WLAN) transmissions from other devices within transmission rate. In block 806, the controller 188 identifies one or more second scent dispensers 132 based on the WLAN transmissions. In some embodiments, the transmission may include identifying data reflecting that the device is a scent dispenser 132 and/or the scent dispenser 132 is actively dispensing. Some embodiments, that identified data may be encrypted, and the controller 188 may decrypt the data for security reasons.

In block 808, the controller 188 of the first scent dispenser 132 may process the signals by broadcasted by the identified second scent dispenser(s) 132 to determine the strength of the signals, and based on the strength of the signals, may determine, in block 810, distance(s) between the second scent dispenser(s) 132 and the first scent dispenser 132.

Based on the distance(s), the controller 188 may, in block 812, adjust an intensity level at which or more scent is being dispensed by the first scent dispenser 132. For example, the controller 188 may have a predefined set of rules correlating scent intensity and a density of scent dispensers 132, and the controller 188 may utilize this data to adjust the intensity level. In a further example, the controller 188 may utilize thresholds reflecting intensity level relative to distance from other scent dispensers 132, and may use the thresholds to adapt scent intensity. In further embodiments, the first scent dispenser 132 may transmit data reflecting the environment including the neighboring second scent dispenser(s) 132 and their dispensing activity, and the dispenser management application 160 may send state settings to one or more of the second scent dispenser(s) 132 to adjust the scent dispensation levels of those dispenser(s) 132. In some instances, sending state settings may include calling functions surfaced by the scent dispenser 132 using various parameters, as discussed elsewhere herein.

Figure 9:
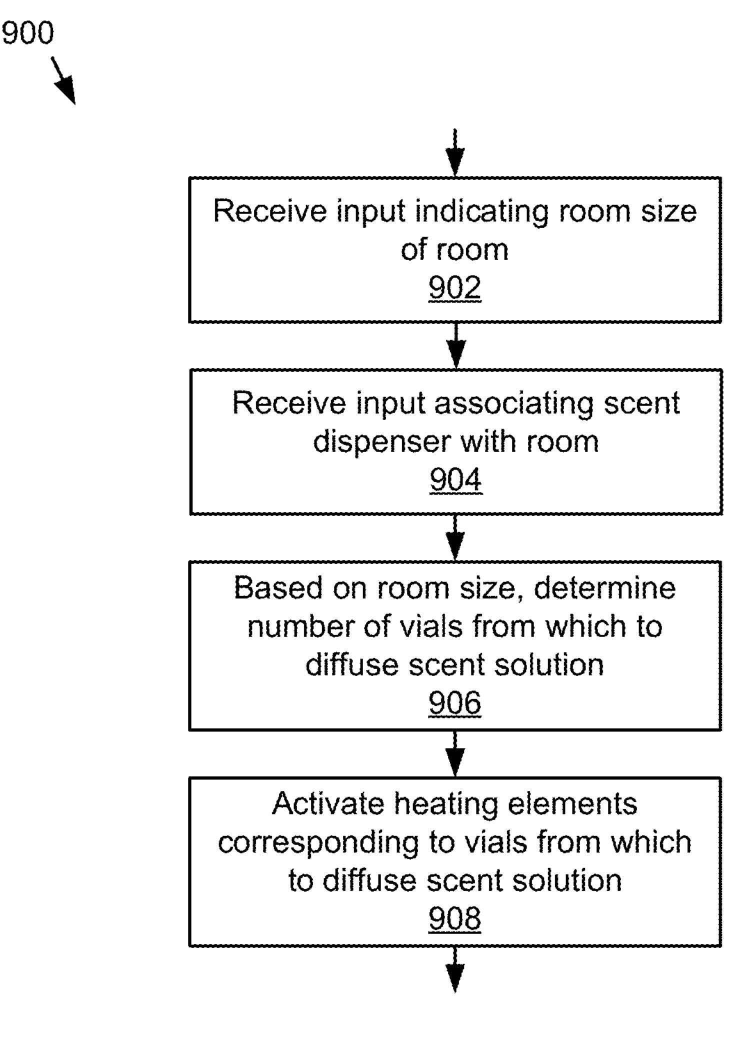
FIG. 9 is a flowchart of an example method for adjusting the dispensation intensity of a scent dispenser based on room size.

FIG. 9 is a flowchart of an example method 900 for adjusting the dispensation intensity of a scent dispenser 132 based on room size. In block 902, the scent application 108 may receive input from the user indicating a room size of a room. For example, the user may input the dimensions of a room using a corresponding interface of the scent application 108 and an input device of the user's computing device 106. In block 904, the scent application 108 may receive input associating the scent dispenser 132 with a particular room. For example, the user, using a corresponding interface of the scent application 108 and an input device of the user's computing device 106, may select a room type from a predefined list of from types and enter a custom name for the room, although other variations are also possible.

In block 906, based on the room size determined in block 902, the dispenser management application 160 may determine a number of vials to use for dispensing scent solution in that room, and may transmit corresponding state settings to the scent dispenser 132. The scent dispenser 132, upon receiving the state settings, may, in block 908, activate the heating elements 196 corresponding to the number of vials determined in block 906. This is advantageous for a larger room which require a scent dispenser 132 to diffuse scent from more than one vial 250 so that the scent level in the room is adequate. This is also advantageous for smaller rooms which may require less scent diffusion, and thus fewer heating elements to be activated.

Figure 10:
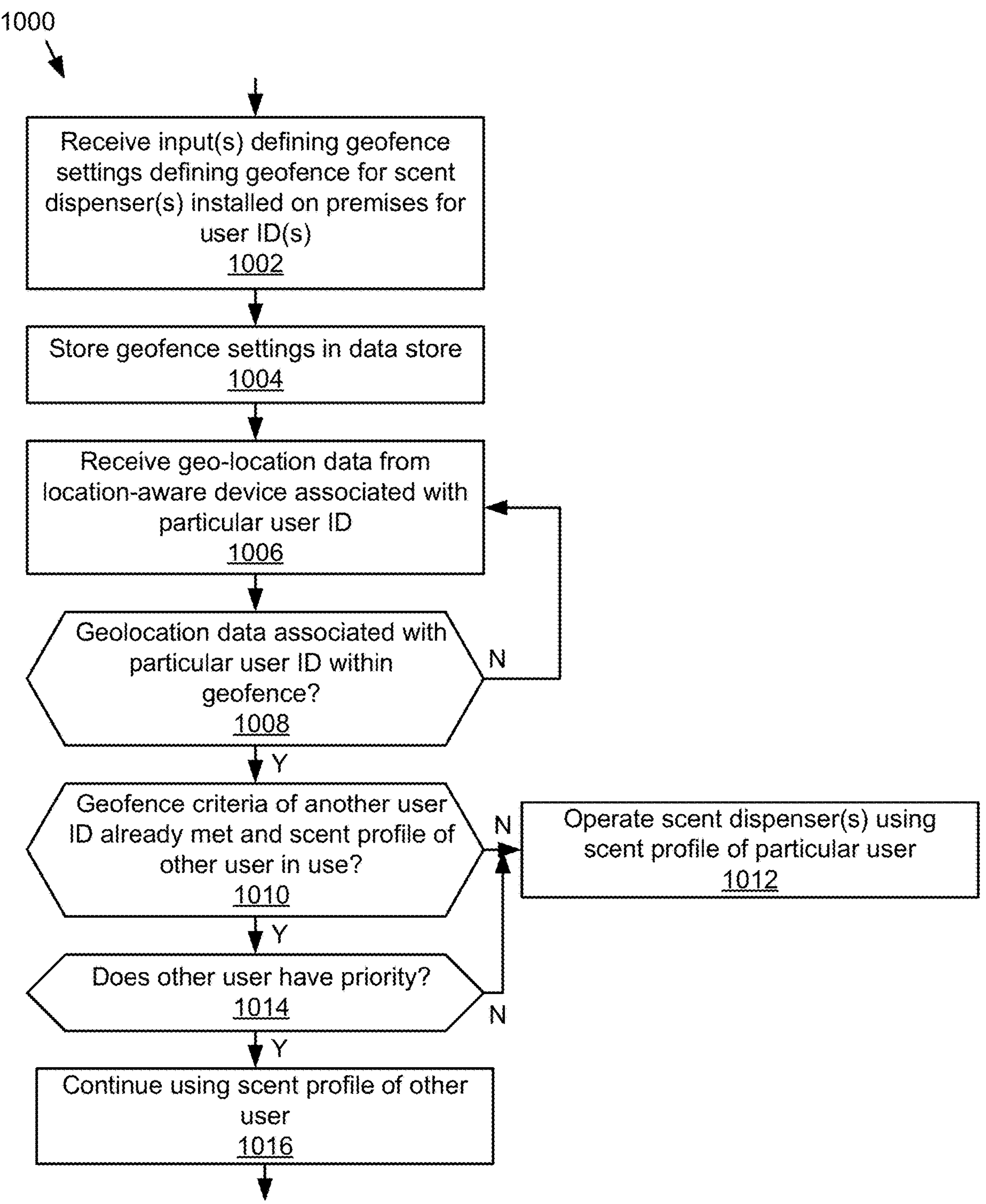
FIG. 10 is a flowchart of an example method for controlling operation of scent dispenser(s) based on geolocation data.

FIG. 10 is a flowchart of an example method 1000 for controlling operation of scent dispenser(s) based on geolocation data.

In block 1002, a scent application may receive input(s) defining geofence settings for scent dispensers 132 installed on particular premises for one or more users (e.g., as reflected by unique user IDs). For example, the user may input, using a graphical user interface displaying a map, the area of the geofence, which may be represented as an overlay in the graphical user interface.

In block 1004, the scent application 108 may transmit the geofence settings to the dispenser management application 160, which may store the settings as user data in the data store 170 in association with the user(s) (e.g., using the user IDs).

In block 1006, the dispenser management application 160 may receive geolocation data from a location-aware device associated with a particular user ID (e.g., the user's smartphone), such as one associated with the geofence data stored in block 1004. In block 1008, the dispenser management application 160 compares the geo-location data associated with the particular user ID with the geofence settings stored for that particular user ID in the data store 170, and based on the comparison determines whether a geolocation of the user is within the geofence. If the geolocation is not within the geofence, the method 1000 may return to block 1006 to receive updated geo-location data. If the geolocation is within the geofence, the dispenser management application 160 may determine whether the geofence criteria of another user ID is associated with a particular user ID in the data store for the same premises already satisfied that geofence criteria and that a scent profile of another user 112 in use (e.g., a first scent is being dispensed by a particular scent dispenser 132 in a particular room the premises according to the settings of that user).

If the determination in block 1010 is negative, the dispenser management application 160 and generate and send state settings based on the scent profile that particular user associated with particular user ID (e.g. as reflected by the user data associated with that particular user ID in the data store 170), and send the state settings to one or more scent dispensers 132 of the premises associated with a particular user ID so the scent dispensers 132 can be configured according to the settings of that particular user, as reflected by the scent profile that particular user.

If the determination in block 1010 is affirmative, the dispenser management application 160 determines which user has priority in block 1014, and if the other user (the scent profile is currently in use) has priority, continues to use a scent profile of the other user 1016 (e.g., does not affect the current operation of the scent dispenser(s) 132) of the premises. In some embodiments, the scent profiles of the particular user and the other user may not conflict for particular premises (e.g., users have selected devices in different rooms for use), in which case both scent profiles may be supported in the conflict resolution may be required. In other words, state settings reflecting the scent profile the particular user can be sent to certain scent dispensers 132 at the premises without affecting the scent dispensation currently occurring within the premises for the other user (e.g., by other scent dispensers 132).

In some embodiments, the dispenser management application 160 may use the geofence settings stored in block 1004 for automatically turning the scent dispensers 132 of a given premises on or off (active or inactive) based on whether or not a particular user this present at the premises are not. For example, as the user leaves the premises, and the mobile device 106 of the user 112 leaves the geofence, the dispenser management application 162 may transmit signals to the scent dispensers 132 in the premises that are on to become inactive. Conversely, as the user's mobile device reenters the geofence upon returning to the premises, the dispenser management application 162 may transmit signals to the scent dispensers 132 in the premises to reactivate/wake-up based on the schedule data stored for the scent dispensers 132 in the data store 170, although other variations are also possible.

In some embodiment, geo-location data associated with a given user, such as GPS data from a user's 112 portable electronic device 106, can be used to further enhance the fragrance disbursement intelligence of the dispenser. For example, through the use of a low-power GPS mode, the scent application 108 operating on the user's device can register an event with the operating system of that device (e.g., iOS™ or Android™) to be notified when the user leaves the approximate radius of their house and/or neighborhood. Upon receiving that event trigger, remote communication to the device may be established via the dispenser management application 160 and the dispenser 132 may be instructed to shut down all fragrance dispensing. The reverse process may occur when the user returns home.

The method 1000 and corresponding embodiments are advantageous as they can automatically prevent wasted scent usage when the user is away from home (or office), and can be particularly helpful for individuals who are frequently away from the premises or to balance scent dispensation in a premises in which multiple users reside. The scent application 108 may further include settings to over-ride operation of the recovery mechanism, and/or adjust the operation thereof, as discusses elsewhere herein.

Figure 11:
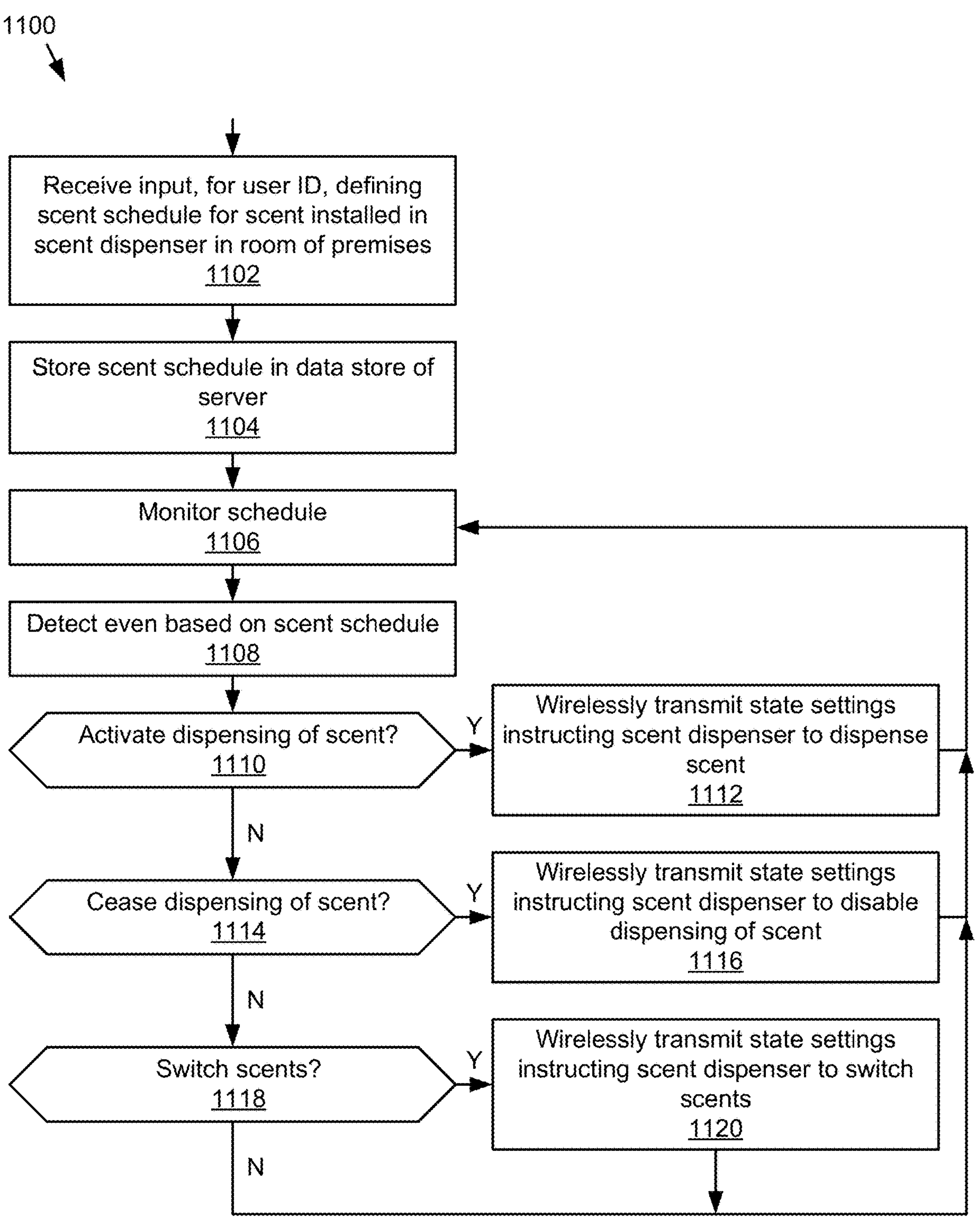
FIG. 11 is a flowchart of an example method for scheduling scent dispensation for room(s) of a premises.

FIG. 11 is a flowchart of an example method 1100 for scheduling scent dispensation for room(s) of a premises. In block limited 1102, the scent application 108 receives input, for a given user ID, defining a set schedule for a set installed in a scent dispenser 132 in a room of a premises.

In block 1104, the scent application 108 may transmit the schedule data to the dispenser management application 160, which in turn may store the scent schedule in the data store 170 of the server 150 in association with the scent dispenser 132 (and other entities, user, premises, etc.).

In block 1106, the dispenser management application 160 may utilize the schedule data to monitor operation of the scent dispenser(s) 132 of that premises, and in block 1108, may detect an event based on the scent schedule. The event may indicate a particular scent dispenser and an action for that scent dispenser.

In block 1110, if the event indicates to start active dispensation of a scent, dispenser management application 160, in block 1112, generates and wirelessly transmits state settings instructing the scent dispenser 132 to dispense the scent, and the controller 188 receives and implements the state settings.

If, in block 1110, the determination is negative, the method 1100 proceeds to block 1114, in which the dispenser management application 160 determines whether to cease dispensing of the scent based on the event. If the determination is affirmative, the dispenser management application 160, in block 1116, generates and wirelessly transmits state settings instructing the scent dispenser 132 to disable dispensing the scent, and the controller 188 receives and implements the state settings.

If, in block 1114, the determination is negative, the method 1100 proceeds to block 1118, in which the dispenser management application 160 determines whether to switch between vials/switch scents. If the determination is affirmative, the dispenser management application 160, in block 1120, generates and wirelessly transmits state settings instructing the scent dispenser 132 to switch scents, and the controller 188 receives and implements the state settings (e.g., by deactivating one heating element 196 and activating another heating element 196 for heating a different scent).

Upon completion of blocks 1112, 1116, 1118 (assuming a negative determination), and/or 1120, the method 1100 may return to block 1106 and repeat from there, and/or may exit.

Figures 12A, 12B:
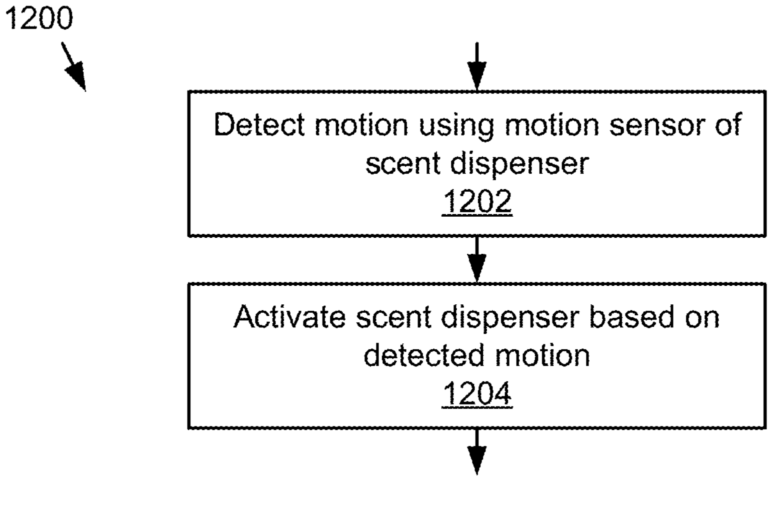
FIG. 12A is a flowchart of an example method for activating a scent dispenser based on detected motion.
FIG. 12B is a flowchart of an example method for using motion detection to control operation of a scent dispenser.

FIG. 12A is a flowchart of an example method 1200 for activating a scent dispenser 132 based on detected motion. In block 1202, a motion sensor of the scent dispenser 132 may detect motion in the environment (e.g., room) within range/surrounding the scent dispenser 132. Responsive to the detected motion, the controller 132 may activate the scent dispenser 132 (e.g. resume dispensing, query for current schedule and dispense according to schedule, await instructions, etc.).

FIG. 12B is a flowchart of an example method 1250 for using motion detection to control operation of a scent dispenser. In block 1206, a motion sensor of the scent dispenser 132 may monitor area. The controller 188 may be coupled to the motion sensor and receive motion data reflecting the presence or absence of motion within the area being monitored. In block 1208, the controller 188 may determine a room to be vacant based on the motion monitoring, which may reflect that there's been no activity in the room for particular period of time (e.g., for a time threshold, no motion has been detected by the motion sensor). In block 1210, the controller 188 may suspend dispensing a scent based on determining the room to be vacant.

The foregoing description, for purpose of explanation, has been described with reference to various embodiments and examples. However, the illustrative discussions above are not intended to be exhaustive or to limit the invention to the precise forms disclosed. Many modifications and variations are possible in view of the above teachings. The various embodiments and examples were chosen and described in order to best explain the principles of the invention and its practical applications, to thereby enable others skilled in the art to utilize the innovative technology with various modifications as may be suited to the particular use contemplated. For instance, it should be understood that the technology described herein can be practiced without these specific details in some cases. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms such as "processing," "computing," "calculating," "determining," "displaying," or the like, refer to the action and methods of a computer system that manipulates and transforms data represented as physical (electronic) quantities within the computer system's registers and memories into other data similarly represented as physical quantities within the computer system memories or registers or other such information storage, transmission or display devices.

A data processing system suitable for storing and/or executing program code, such as the computing system and/or devices discussed herein, may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices can be coupled to the system either directly or through intervening I/O controllers. The data processing system may include an apparatus may be specially constructed for the required purposes, or it may comprise a general-purpose computer selectively activated or reconfigured by a computer program stored in the computer.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies and other aspects may not be mandatory or significant, and the mechanisms that implement the specification or its features may have different names, divisions, and/or formats.

Furthermore, the modules, routines, features, attributes, methodologies and other aspects of the disclosure can be implemented as software, hardware, firmware, or any combination of the foregoing. The technology can also take the form of a computer program product accessible from a computer-usable or computer-readable medium providing program code for use by or in connection with a computer or any instruction execution system. Wherever a component, an example of which is a module or engine, of the specification is implemented as software, the component can be implemented as a standalone program, as part of a larger program, as a plurality of separate programs, as a statically or dynamically linked library, as a kernel loadable module, as firmware, as resident software, as microcode, as a device driver, and/or in every and any other way known now or in the future. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A scent dispensing device, comprising:

a body with a plurality of vial bays;

a cover configured to be positioned on the body to hide the plurality of vial bays;

a wireless interface configured to wirelessly communicate with a management server to receive control data stored on the management server, the control data including solutions settings based on an association of the scent dispensing device with a particular room; and a controller configured to receive the control data to dispense a scent and cause a scent to be dispensed from one or more of a first scent vial, a second scent vial, and a third scent vial positioned within the plurality of vial bays based on the solution settings and an attribute of the particular room.

2. The scent dispensing device of claim 1, wherein the cover is a removable cover.

3. The scent dispensing device of claim 1, wherein the plurality of bays includes a first bay and a second bay, the first bay and the second bay being adjacently situated.

4. The scent dispensing device of claim 3, further comprising:

a switching mechanism configured to switch between the first bay and the second bay based on the instructions provided from a dispenser management application.

5. The scent dispensing device of claim 1, further comprising:

a plurality of heating elements disposed in the body in association with the plurality of vial bays, wherein when the controller causes the scent to be dispensed from one or more of the first scent vial, the second scent vial, and the third scent vial positioned within the plurality of vial bays, the controller causes one or more of the plurality of heating elements to heat the one or more of the first scent vial, the second scent vial, and the third scent vial to cause the scent to be dispensed.

6. The scent dispensing device of claim 1, wherein the wireless interface is further configured to facilitate a wirelessly communication between the controller and the dispenser management application.

7. The scent dispensing device of claim 6, wherein the dispenser management application is configured to receive updated control data from a client device, the updated control data representing a request to change a scent setting and wherein the dispenser management application is configured to provide the updated control data using the wireless interface to the controller to cause the control data to change the scent setting.

8. A method comprising:

receiving via a computer network control data including a request to dispense one or more scents from a scent dispensing device based on an association of the scent dispensing device with a particular room, the scent dispensing device including a body with a plurality of vial bays including a first scent vial, a second scent vial, and a third scent vial positioned within the plurality of vial bays and a plurality of heating elements where each heating element is associated with a vial bay of the plurality of vial bays;

determining which heating elements of the plurality of heating elements are associated with the request to dispense the one or more scents; and causing the scent dispensing device to dispense the one or more scents by sending instructions to the determined heating elements of the plurality of heating elements to heat up one or more of the first scent vial, the second scent vial, and the third scent vial based on the request to dispense the one or more scents and an attribute of the particular room.

9. The method of claim 8, wherein the scent dispensing device includes a cover configured to be positioned over the plurality of vial bays.

10. The method of claim 8, wherein the plurality of vial bays includes a first by and a second bay, the first bay and the second bay being adjacently situated.

11. The method of claim 10, wherein sending instructions to the determined heating elements of the plurality of heating elements further comprises sending instructions to a switching mechanism of the scent dispensing device, the switching mechanism being configured to switch between the first vial bay and the second vial bay based on the instructions.

12. The method of claim 8, wherein the request to dispense one or more scents from the scent dispensing device further comprises a request to dispense a first scent from the first scent vial and a request to dispense a second scent from the second scent vial.

13. The method of claim 12, wherein the first scent is dispensed from the first scent vial and the second scent is dispensed from the second scent vial simultaneously.

14. The method of claim 13, wherein the first scent is dispensed simultaneously with the second scent by heating multiple heating elements.

15. A scent dispensing device, comprising:

a body with a first vial bay, a second vial bay, and a third vial bay, the first vial bay including a first scent in a first scent vial, the second vial bay including a second scent in a second scent vial, and the third vial bay including a third scent in a third scent vial;

a cover configured to be positioned on the body to hide the first vial bay, the second vial bay, and the third vial bay;

a wireless interface configured to wirelessly communicate with a management server to receive control data stored on the management server, the control data including solutions settings based on an association of the scent dispensing device with a particular room; and a controller configured to cause one or more of the first scent to be dispensed from the first scent vial, the second scent to be dispensed from the second scent vial, and the third scent to be dispensed from the third scent vial based on the solution settings and an attribute of the particular room.

16. The scent dispensing device of claim 15, wherein the cover is a removable cover.

17. The scent dispensing device of claim 15, wherein the controller is configured to mix scents by emitting the one or more of the first cent first scent to be dispensed from the first scent vial, the second scent to be dispensed from the second scent vial, and the third scent to be dispensed from the third scent vial simultaneously.

18. The scent dispensing device of claim 15, wherein the controller causes the one or more of the first scent to be dispensed from the first scent vial, the second scent to be dispensed from the second scent vial, and the third scent to be dispensed from the third scent vial based on control data.

19. The scent dispensing device of claim 18, wherein the control data includes one or more of scent diffusion schedules, scent diffusion intensities, and user preferences.

20. The scent dispensing device of claim 19, wherein the scent dispensing device includes one or more heating elements that causes the first scent to be dispensed from the first scent vial, the second scent to be dispensed from the second scent vial, and the third scent to be dispensed from the third scent vial based on control data indicating how the controller should cause the heating elements to operate.

* * * * *